(12) United States Patent
Prat et al.

(10) Patent No.: US 12,223,435 B2
(45) Date of Patent: Feb. 11, 2025

(54) SYSTEM AND METHOD FOR MOLECULAR RECONSTRUCTION FROM MOLECULAR PROBABILITY DISTRIBUTIONS

(71) Applicant: Ro5 Inc., Dallas, TX (US)

(72) Inventors: Alvaro Prat, Barcelona (ES); Alwin Bucher, Cambridge (GB); Zygimantas Jocys, Hove (GB); Roy Tal, Dallas, TX (US)

(73) Assignee: RO5 INC., Dallas, TX (US)

( * ) Notice: Subject to any disclaimer, the term of this patent is extended or adjusted under 35 U.S.C. 154(b) by 688 days.

(21) Appl. No.: 17/540,153

(22) Filed: Dec. 1, 2021

(65) Prior Publication Data

US 2022/0198286 A1  Jun. 23, 2022

Related U.S. Application Data

(63) Continuation-in-part of application No. 17/399,931, filed on Aug. 11, 2021, now Pat. No. 11,263,534, (Continued)

(51) Int. Cl.
*G06N 5/022* (2023.01)
*G06F 16/951* (2019.01)
(Continued)

(52) U.S. Cl.
CPC ........... *G06N 5/022* (2013.01); *G06F 16/951* (2019.01); *G06F 18/22* (2023.01); *G06N 3/08* (2013.01);
(Continued)

(58) Field of Classification Search
CPC .......... G06N 5/022; G06N 3/08; G06N 3/045; G06N 3/044; G06N 3/048; G06N 3/047;
(Continued)

(56) References Cited

U.S. PATENT DOCUMENTS

2019/0304568 A1   10/2019   Wei et al.
2020/0279151 A1    9/2020   Li et al.

FOREIGN PATENT DOCUMENTS

CA            3141526 A1 * 12/2020  .............. G06F 17/11
WO    WO-2022259185 A1 * 12/2022  .............. G06N 3/045

* cited by examiner

*Primary Examiner* — Charlotte M Baker
(74) *Attorney, Agent, or Firm* — Galvin Patent Law LLC; Brian R. Galvin

(57) ABSTRACT

A system and method comprising a transmoler that identifies common substructures of a given 3D conformer and predicts its structural information. First, based on contrastive learning, substructure embeddings are learned in an unsupervised manner. Secondly, a novel oriented 3D object regressor predicts the dimensions and directions of each substructure in a conformer as well as its fingerprint embedding which are used to create differentiable junction tree molecular graphs. Lastly, using the junction tree graphs, molecular representations such as DeepSMILES are generated which represent new and novel molecules. The system may also generate conformers directly from a pocket. A pocket may be input to the model and the model learns to generate structures which can fit that pocket by conditioning the generative system. Furthermore, structure-based contrastive embeddings generated for transmoler can be recycled in structure-based generative modelling.

20 Claims, 51 Drawing Sheets

Related U.S. Application Data which is a continuation-in-part of application No. 17/202,722, filed on Mar. 16, 2021, now Pat. No. 11,256,994, which is a continuation-in-part of application No. 17/174,677, filed on Feb. 12, 2021, now Pat. No. 11,615,324, which is a continuation of application No. 17/171,494, filed on Feb. 9, 2021, now Pat. No. 11,176,462, which is a continuation of application No. 17/166,435, filed on Feb. 3, 2021, now Pat. No. 11,080,607.

(60) Provisional application No. 63/126,388, filed on Dec. 16, 2020, provisional application No. 63/126,372, filed on Dec. 16, 2020, provisional application No. 63/126,349, filed on Dec. 16, 2020.

(51) Int. Cl.
*G06F 18/22* (2023.01)
*G06N 3/08* (2023.01)
*G16B 15/00* (2019.01)
*G16B 40/00* (2019.01)
*G16B 45/00* (2019.01)
*G16B 50/10* (2019.01)
*G16C 20/70* (2019.01)

(52) U.S. Cl.
CPC .............. *G16B 15/00* (2019.02); *G16B 40/00* (2019.02); *G16B 45/00* (2019.02); *G16B 50/10* (2019.02); *G16C 20/70* (2019.02)

(58) Field of Classification Search
CPC ....... G06N 3/088; G06N 3/084; G06F 16/951; G06F 18/22; G16B 15/00; G16B 40/00; G16B 45/00; G16B 50/10; G16C 20/70; G16C 20/30; G16C 20/90; G16C 20/50; G06V 10/751; G06V 10/82
USPC .......................................................... 702/19
See application file for complete search history.

```
self.model = nn.Sequential(
    # Expand Channels
    l.SpecConvBlock3d(self.nc, self.ngf, self.activations['spec'], self.
dropouts['low'], **self.large_conv_kwargs),
    l.SpecConvBlock3d(self.ngf, self.ngf, self.activations['spec'],
self.dropouts['low'], **self.large_conv_kwargs), l.SpecConvBlock3d(self.ngf, 2*self.ngf, self.activations['spec'],
self.dropouts['low'], **self.base_conv_kwargs),
    l.SpecConvBlock3d(2*self.ngf, 2*self.ngf, self.activations['spec'],
self.dropouts['low'], **self.base_conv_kwargs), l.SpecConvBlock3d(2*self.ngf, 4*self.ngf, self.activations['spec'],
self.dropouts['low'], **self.base_conv_kwargs),
    # Contract Channels
    l.SpecConvBlock3d(4*self.ngf, 2*self.ngf, self.activations['spec'],
self.dropouts['low'], **self.base_conv_kwargs),
    l.SpecConvBlock3d(2*self.ngf, self.ngf, self.activations['spec'],
self.dropouts['low'], **self.base_conv_kwargs),
    l.OutConvBlock3d(self.ngf, self.nc, self.activations['output'],
**self.large_conv_kwargs),
)
```

Fig. 32

```
self.model = nn.Sequential(
    l.NoBatchUpsampledTrilinearBlock3d(self.nc, 2*self.nc, (49*2, 37*2,
25*2), self.activations['spec'], dropout=self.dropouts['med'], **self.
up_conv_kwargs), l.NoBatchSpecConvBlock3d(2*self.nc, self.ngf, self.activations
['spec'], dropout=self.dropouts['low'], **self.large_conv_kwargs), l.NoBatchSpecConvBlock3d(self.ngf, 2*self.ngf, self.activations
['spec'], dropout=self.dropouts['low'], **self.large_conv_kwargs),
    l.NoBatchResNetBasicBlock(2*self.ngf, 2*self.ngf), l.NoBatchSpecConvBlock3d(2*self.ngf, 4*self.ngf, self.activations
['spec'], dropout=self.dropouts['low'], **self.base_conv_kwargs),
    l.NoBatchResNetBasicBlock(4*self.ngf, 4*self.ngf), l.NoBatchSpecConvBlock3d(4*self.ngf, 3*self.ngf, self.activations
['spec'], dropout=self.dropouts['low'], **self.drop_conv_kwargs),
    l.NoBatchResNetBasicBlock(8*self.ngf, 2*self.ngf), l.NoBatchSpecConvBlock3d(2*self.ngf, 8*self.ngf, self.activations
['spec'], dropout=self.dropouts['low'], **self.linear_conv_kwargs), l.NoBatchSpecConvBlock3d(8*self.ngf, 2*self.ngf, self.activations
['spec'], dropout=self.dropouts['low'], **self.depthwise_conv_kwargs),

# Use logits instead (NO SIGMOID) because we are using nn.
BCELossWithLogits instead due to autocast reasons & improved stability.
    l.OutConvBlock3d(2*self.ngf, 1, activation=None, **self.
depthwise_conv_kwargs),
    l.Flatten()
)
```

Fig. 33

SYSTEM AND METHOD FOR MOLECULAR RECONSTRUCTION FROM MOLECULAR PROBABILITY DISTRIBUTIONS

CROSS-REFERENCE TO RELATED APPLICATIONS

Priority is claimed in the application data sheet to the following patents or patent applications, the entire written description of each of which is expressly incorporated herein by reference in its entirety:
Ser. No. 17/399,931
Ser. No. 17/202,722
Ser. No. 17/174,677
Ser. No. 17/171,494
Ser. No. 17/166,435
63/126,349
63/126,372
63/126,388

BACKGROUND

Field of the Art

The disclosure relates to the field of medical research, and more particularly to the field of prediction generating valid molecules using 3D-based representation and analysis.

Discussion of the State of the Art

Pharmaceutical research is hindered by the complexity of protein-ligand interactions. Proteins are macromolecules that are involved in a large array of biological functions. Proteins are macromolecules, comprising long chains of amino acids, each of which is itself an organic molecule. The shape of proteins determines their bioactivity, and the shape of a protein is determined by the way the protein folds based on its molecular structure. The complexity of proteins and their folding patterns makes their final shapes computationally intractable.

Ligands further complicate the issue as each ligand further changes the shape of the protein, which changes its bioactivity. Inferring the interaction between a protein and a ligand alone is a computationally challenging task because proteins are two or three orders of magnitude larger than a typical ligand and the number of possible interaction sites is very large. Further, each ligand further changes the shape of the protein, which changes its bioactivity, and the possible spatial conformations of a protein is several orders of magnitude larger than a ligand. Lastly, identifying substructures from 3D conformations is a seemingly tedious process. There are thousands of substructures and infinitely many conformers which cover the chemical space.

What is needed is a system and method for computationally tractable prediction of valid molecules using a substructure-level preceptor.

SUMMARY

Accordingly, the inventor has conceived and reduced to practice, a system and method comprising a transmoler that identities common substructures of a given 3D conformer and predicts its structural information. First, based on contrastive learning, substructure embeddings are learned in an unsupervised manner. Secondly, a novel oriented 3D object regressor predicts the dimensions and directions of each substructure in a conformer as well as its fingerprint embedding which are used to create differentiable junction tree molecular graphs. Lastly, using the junction tree graphs, molecular representations such as SMILES are generated which represent new and novel molecules. The system may also generate conformers directly from a pocket. A pocket may be input to the model and the model learns to generate structures which can fit that pocket by conditioning the generative system. Furthermore, structure-based contrastive embeddings generated for transmoler can be recycled in structure-based generative modelling.

According to a first preferred embodiment, a system for the reconstruction of molecular representations from molecular probability distributions is disclosed, comprising: a computer system comprising a memory and a processor; an embeddings module, comprising a first plurality of programming instructions stored in the memory and operating on the processor, wherein the first plurality of programming instructions, when operating on the processor, causes the computer system to: receive a dataset of molecules comprising ground-truth information relating to the molecules; use the dataset with an encoder-decoder to train a model of each molecule in the dataset, wherein the molecule model comprises every substructure in each molecule, and wherein each substructure is represented as an embedding; use contrastive optimization across all the molecule models to form clusters of similar substructures; and assign signatures to each embedding, wherein similar substructure embeddings have matching signatures; a substructure processing module, comprising a second plurality of programming instructions stored in the memory and operating on the processor, wherein the second plurality of programming instructions, when operating on the processor, causes the computer system to; receive a probability distribution of a molecule; predict a set of molecular descriptors from the probability distribution, wherein the set of molecular descriptors comprises at least one of the following: substructure centroids, substructure dimensions, substructure directions, substructure embeddings, or some combination thereof; wherein the substructure embeddings are determined by comparative signature analysis with the substructure embeddings generated by the embeddings module; and encode the set of molecular descriptors into a tensor, wherein the tensor fully describes the molecule; and a junction tree connector module, comprising a third plurality of programming instructions stored in the memory and operating on the processor, wherein the third plurality of programming instructions, when operating on the processor, causes the computer system to: receive the tensor of molecular predictions; use the tensor to predict the junction tree node structure; use the tensor to predict the atomic assignment of each atom in each substructure; connect the substructures together to form a valid molecule using the predicted junction tree node structure and atomic assignments; and produce a molecular string which is fully representative of the molecule from the molecular probability distribution.

According to a second preferred embodiment, a method for the reconstruction of molecular represent ions from molecular probability distributions is disclosed, comprising the steps of: training an encoder-decoder to model each molecule in a dataset, wherein the molecule model comprises every substructure in each molecule of the dataset, and wherein each substructure is represented as an embedding; using contrastive optimization across all the molecule models to form clusters of similar substructures; assigning signatures to each embedding, wherein similar substructure embeddings have similar signatures and less-similar substructure embeddings have less-similar signatures; predicting a set of molecular descriptors from a molecular probability distribution, wherein the set of molecular descriptors comprises at least one of the following: substructure centroids, substructure dimensions, substructure directions, substructure embeddings, or some combination thereof; determining the molecular descriptor substructure embedding by comparative signature analysis with the generated substructure embeddings; encoding the set of molecular descriptors into a tensor, wherein the tensor fully describes the molecule; using the tensor to predict the junction tree node structure of the molecular probability distribution and to predict the atomic assignment of each atom in each substructure; connecting the substructures together to form a valid molecule using the predicted junction tree node structure and predicted atomic assignments; and producing a molecular string which is fully representative of the molecule from the molecular probability distribution According to various aspects; wherein an object-detection algorithm is used for the prediction of a set of molecular properties; wherein the object-detection algorithm uses a template matching task rather than a classification task; wherein a deep learning transformer is used to connect the substructures together; wherein the molecular string is a SMILES string; wherein the molecular string is a Deep-SMILES string, preferable to deep learning applications; wherein the probability distribution of a molecule is generated by a variational autoencoder; wherein the embeddings generated can be recycled in structure-based generative modelling; wherein a Hungarian-matching algorithm is used to determine the ground-truth set of molecular properties; and wherein the prediction of the junction tree node structure is determined using a Hungarian-matching algorithm by pruning incorrect nodes.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

FIG. 32 is exemplary programming code for a pretrained generator used in a molecular reconstruction module.

FIG. 33 is exemplary programming code for a pretrained discriminator used in a molecular reconstruction module.

DETAILED DESCRIPTION

Figure 1:
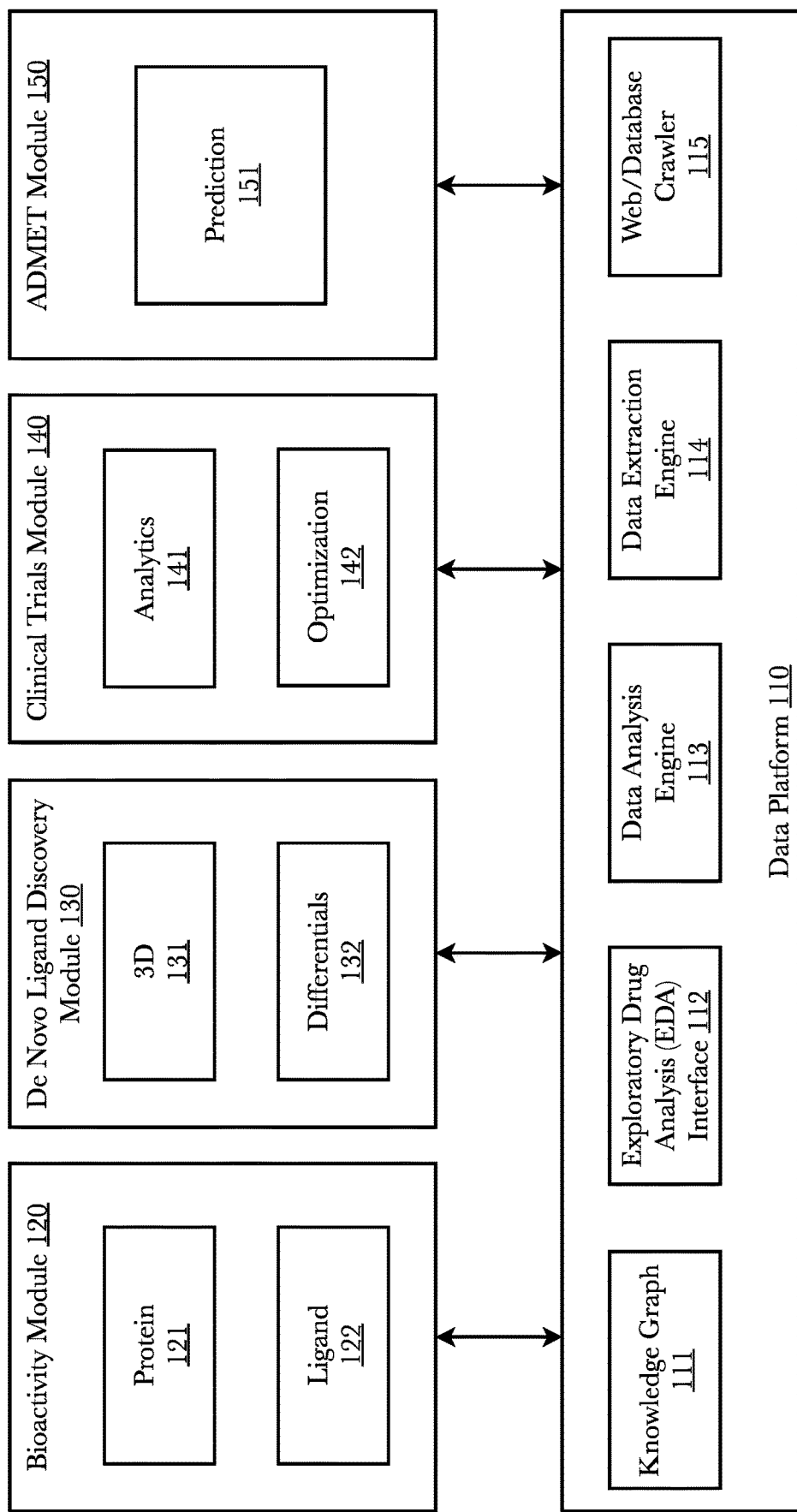
FIG. 1 is a block diagram illustrating an exemplary overall system architecture for a pharmaceutical research system.

Accordingly, the inventor has conceived and reduced to practice, a system and method comprising a transmoler that identifies common substructures of a given 3D conformer and predicts its structural information. First, based on contrastive learning, substructure embeddings are learned in an unsupervised manner. Secondly, a novel oriented 3D object regressor predicts the dimensions and directions of each substructure in a conformer as well as its fingerprint embedding which are used to create differentiable junction tree molecular graphs. Lastly, using the junction tree graphs, molecular representations—such as DeepSMILES, as one example—are generated which represent new and novel molecules. The system may also generate conformers directly from a pocket. A pocket may be input to the model and the model learns to generate structures which can fit that pocket by conditioning the generative system. Furthermore, structure-based contrastive embeddings generated for transmoler can be recycled in structure-based generative modelling.

The motivation of a transmoler is to identify substructures from 3D conformations, which is a seemingly tedious process. There are thousands of substructures and infinitely many conformers which cover the chemical space. Generating a substructure-level perceptor can bring great value to cheminformatics industry in many ways. Specifically, transmoler can be used to detect substructures from generated density clouds directly from the 3D de novo & bioactivity modules and pipelines described in at least FIG. 1, FIG. 39, and other embodiments contained herein and parent applications. This is a crucial task in completing an end-to-end differentiable system and parsing of the generated molecules (in order to automatically generate canonical molecular representations). Such system may be used to generate conformers directly from a pocket. A pocket may be input into the platform and the model learns to generate structures which can fit that pocket by conditioning the generative system with an exploration prior. This may also be exploited to find the right PDBs in ChemBL, expanding proprietary bioactivity datasets further. Transmoler can scan a set of pockets belonging to a protein target and generate conformers for each unique PDB (one for each binding site). For every active site it may be evaluated if the query ligand is structurally similar to the generated conformers or not. Subsequently, the active site is selected which produces conformers with the highest structural similarity to the query ligand, and reject others which do not meet this criterion. The system can be easily verified by generating a decoy dataset from PDBBind2020. The same distribution can be used for binding site similarity.

Additionally, structure-based contrastive embeddings generated for transmoler can be recycled in structure-based generative modelling. A JTVAE (junction tree variational autoencoder) has a noticeable flaw from class imbalance and the fact that all substructures are equidistant (one-hot vectors), making multi-class classification (+800 classes) an extremely complex task (low information entropy). In contrast, embeddings created by the transmoler are much more informative and generalizable since imbalanced classes (substructures) will produce similar embeddings to neighboring substructures (those with similar structures). And also since these are continuous and are trained to lie in the shell of a hypersphere, interpolation between embeddings is very smooth, in contrast to class-based learning, where argmax functions are used to select the most likely embedding. Moreover because these are conformer-agnostic (in a substructure level) which reduces the complexity of 3D-based modelling.

Lastly, substructure detection for 3D scaffolding can be used to condition generative models to have certain substructures. Given a model which readily identifies substructures, said model may be exploited to constrain optimization & generation of certain compounds to consist of several "seed" or "anchor" substructures. For instance, one might want to generate molecules which contain sulfonyl fluorides.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"Bioactivity" as used herein means the physiological effects of a molecule on an organism (i.e., living organism, biological matter).

"Docking" as used herein means a method which predicts the orientation of one molecule to a second when bound to each other to form a stable complex. Knowledge of the preferred orientation in turn may be used to predict the strength of association or binding affinity between two molecules.

"Edges" as used herein means connections between nodes or vertices in a data structure. In graphs, an arbitrary number of edges may be assigned to any node or vertex, each edge representing a relationship to itself or any other node or vertex. Edges may also comprise value, conditions, or other information, such as edge weights or probabilities.

"FASTA" as used herein means any version of the FASTA family (e.g., FASTA, FASTP, FASTQ, etc.) of chemical notations for describing nucleotide sequences or amino acid (protein) sequences using text (e.g., ASCII) strings.

"Force field" as used herein means a collection of equations and associated constants designed to reproduce molecular geometry and selected properties of tested structures. In molecular dynamics a molecule is described as a series of charged points (atoms) linked by springs (bonds).

"Ligand" as used herein means a substance that forms a complex with a biomolecule to serve a biological purpose. In protein-ligand binding, the ligand is usually a molecule which produces a signal by binding to a site on a target protein. Ligand binding to a receptor protein alters the conformation by affecting the three-dimensional shape orientation. The conformation of a receptor protein composes the functional state. Ligands comprise substrates, inhibitors, activators, signaling lipids, and neurotransmitters.

"Nodes" and "Vertices" are used herein interchangeably to mean a unit of a data structure comprising a value, condition, or other information. Nodes and vertices may be arranged in lists, trees, graphs, and other forms of data structures. In graphs, nodes and vertices may be connected to an arbitrary number of edges, which represent relationships between the nodes or vertices. As the context requires, the term "node" may also refer to a node of a neural network (also referred to as a neuron) which is analogous to a graph node in that it is a point of information connected to other points of information through edges.

"Pocket" or "Protein binding pocket" as used herein leans a cavity (i.e., receptor, binding site) on the surface or in the interior of a protein that possesses suitable properties for binding a ligand. The set of amino acid residues around a binding pocket determines its physicochemical characteristics and, together with its shape and location in a protein, defines its functionality.

"Pose" as used herein means a molecule within a protein binding site arranged in a certain conformation.

"Proteins" as used herein means large biomolecules, or macromolecules, consisting of one or more long chains of amino acid residues. Proteins perform a vast array of functions within organisms, including catalyzing metabolic reactions, DNA replication, responding to stimuli, providing structure to cells and organisms, and transporting molecules from one location to another. Proteins differ from one another primarily in their sequence of amino acids, which is dictated by the nucleotide sequence of their genes, and which usually results in protein folding into a specific 3D structure that determines its activity.

"SMILES" as used herein means any version of the "simplified molecular-input line-entry system," which is form of chemical notation for describing the structure of molecules using short text (e.g., ASCII) strings.

Conceptual Architecture

FIG. 1 is a block diagram illustrating an exemplary overall system architecture for a pharmaceutical research system. The exemplary architecture comprises a data platform 110 which provides the core functionality of the system, plus one or more modules that utilize the data platform 110 to provide functionality in specific areas of research, in this case a bioactivity module 120, a de novo ligand discovery module 130, a clinical trials module 140, and an absorption, distribution, metabolism, excretion, and toxicity (ADMET) module 150.

The data platform 110 in this embodiment comprises a knowledge graph 111, an exploratory drug analysis (EDA) interface 112, a data analysis engine 113, a data extraction engine 114, and web crawler/database crawler 115. The crawler 115 searches for and retrieves medical information such as published medical literature, clinical trials, dissertations, conference papers, and databases of known pharmaceuticals and their effects. The crawler 115 feeds the medical information to a data extraction engine 114, which uses natural language processing techniques to extract and classify information contained in the medical literature such as indications of which molecules interact with which proteins and what physiological effects have been observed. Using the data extracted by the data extraction engine 114, a knowledge graph 111 is constructed comprising vertices (also called nodes) representing pieces of knowledge gleaned from the data and edges representing relationships between those pieces of knowledge. As a very brief example, it may be that one journal article suggests that a particular molecule is useful in treating a given disease, and another journal article suggests that a different molecule is useful for treating the same disease. The two molecules and the disease may be represented as vertices in the graph, and the relationships among them may be represented as edges between the vertices. The EDA interface 112 is a user interface through which pharmaceutical research may be performed by making queries and receiving responses. The queries are sent to a data analysis engine 113 which uses the knowledge graph 111 to determine a response, which is then provided to the user through the EDA interface 112. In some embodiments, the data analysis engine 113 comprises one or more graph-based neural networks (graph neural networks, or GNNs) to process the information contained in the knowledge graph 111 to determine a response to the user's query. As an example, the user may submit a query for identification of molecules likely to have similar bioactivity to a molecule with known bioactivity. The data analysis engine 113 may process the knowledge graph 111 through a GNN to identify such molecules based on the information and relationships in the knowledge graph 111.

The bioactivity module 120 utilizes the data platform 110 to analyze and predict the bioactivity of molecules based on protein 121 and ligand 122 similarities and known or suspected protein 121 and ligand 122 compatibilities. The module utilizes the knowledge graph 111 and data analysis engine 113 capabilities of the data platform 110, and in one embodiment is configured to predict the bioactivity of a molecule based on and their known or suspected compatibilities with certain combinations of proteins 121 and ligands 122. Thus, using the bioactivity module 120, users can research molecules by entering queries through the EDA interface 112, and obtaining using predictions of bioactivity based on known or suspected bioactivity of similar molecules and their compatibilities with certain protein 121 and ligand 122 combinations.

The de novo ligand discovery module 130 utilizes the data platform 110 to identify ligands and their properties through data enrichment and interpolation/perturbation. The module utilizes the knowledge graph 111 and data analysis engine 113 capabilities of the data platform 110, and in one embodiment is configured to identify ligands with certain properties based on three dimensional (3D) models 131 of known ligands and differentials of atom positions 132 in the latent space of the models after encoding by a 3D convolutional neural network (3D CNN), which is part of the data analysis engine 113. In one embodiment, the 3D model comprises a voxel image (volumetric, three dimensional pixel image) of the ligand. In cases where enrichment data is available, ligands may be identified by enriching the SMILES string for a ligand with information about possible atom configurations of the ligand and converting the enriched information into a plurality of 3D models of the atom. In cases where insufficient enrichment information is available, one possible configuration of the atoms of the ligand may be selected, and other configurations may be generated by interpolation or perturbation of the original configuration in the latent space after processing the 3D model through the CNN. In either case, the 3D models of the ligands are processed through a CNN, and a gradient descent is applied to changes in atom configuration in the latent space to identify new ligands with properties similar to the modeled ligands. Thus, using the de novo ligand discovery module 130, users can identify new ligands with properties similar to those of modeled ligands by entering queries through the EDA interface 112.

The clinical trials module 140 utilizes the data platform 110 to analyze 141 and optimize 142 the knowledge contained in or derived from clinical trials. The module utilizes the knowledge graph 111 and data analysis engine 113 capabilities of the data platform 110, and in one embodiment is configured to return clinical trials similar to a specified clinical trial in one or more aspects (e.g., proteins and ligands studied, methodology, results, etc.) based on semantic clustering within the knowledge graph 111. Thus, using the clinical trials module 140, users can research a large database of clinical trials based on aspects of interest by entering queries through the EDA interface 112.

The ADMET module 150 utilizes the data platform 110 to predict 151 absorption, distribution, metabolism, excretion, and toxicity characteristics of ligands based on ADMET databases. The module utilizes the knowledge graph 111 and data analysis engine 113 capabilities of the data platform 110, and in one embodiment is configured to return ligands with characteristics similar to, or dissimilar to, a specified ligand in one or more respects (e.g., a ligand with similar absorption and metabolism characteristics, but dissimilar toxicity characteristics) based on semantic clustering within the knowledge graph 111. Thus, using the ADMET module 150, users can research a large ADMET database based on aspects of interest by entering queries through the EDA interface 112.

Figure 2:
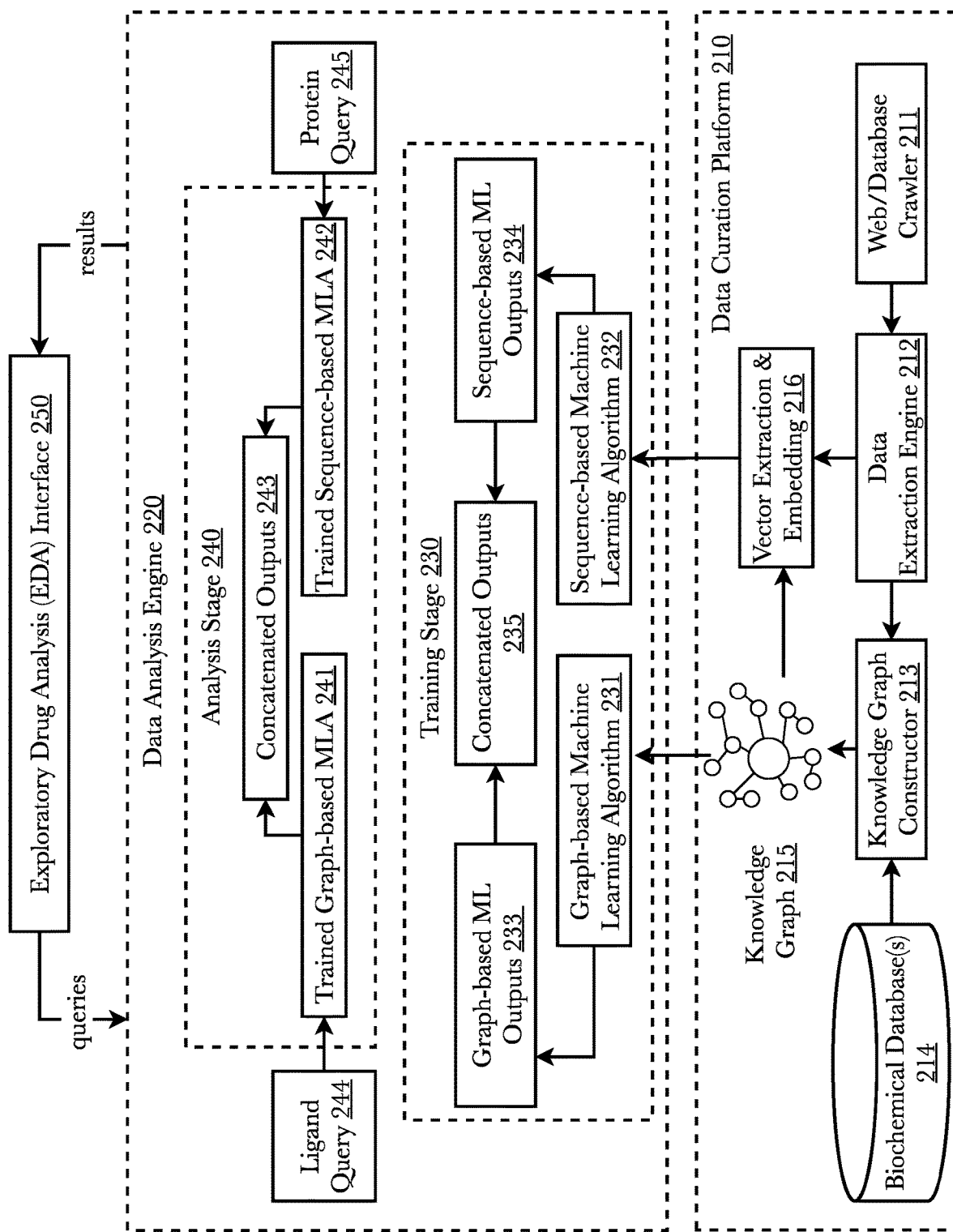
FIG. 2 is a block diagram illustrating an exemplary system architecture for an embodiment of a pharmaceutical research system utilizing combined graph-based and sequence-based prediction of molecule bioactivity.

FIG. 2 is a block diagram illustrating an exemplary system architecture for an embodiment of a pharmaceutical research system utilizing combined graph-based and sequence-based prediction of molecule bioactivity. In this embodiment, the system comprises a data curation platform 210, a data analysis engine 220 comprising a training stage 230 and an analysis stage 240, and an exploratory drug analysis interface 250. The knowledge graph 215 does not refer to a graph representation of the inputs to the model, but to a relational structure of the data in the database itself. The knowledge graph 215 itself is not used as input.

In the data curation platform 210, a web crawler/database crawler 211 is configured to search for and download medical information materials including, but not limited to, archives of published medical literature such as MEDLINE and PubMed, archives of clinical trial databases such as the U.S. National Library of Medicine's ClinicalTrials.gov database and the World Health Organization International Clinical Trials Registry Platform (ICTRP), archives of published dissertations and theses such as the Networked Digital Library of These and Dissertations (NDLTD), archives of grey literature such as the Grey Literature Report, and news reports, conference papers, and individual journals. As the medical information is downloaded, it is fed to a data extraction engine 212 which may perform a series of operations to extract data from the medical information materials. For example, the data extraction engine 212 may first determine a format of each of the materials received (e.g., text, PDFs, images), and perform conversions of materials not in a machine-readable or extractable format (e.g., performing optical character recognition (OCR) on PDFs and images to extract any text contained therein). Once the text has been extracted from the materials, natural language processing (NLP) techniques may be used to extract useful information from the materials for use in analysis by machine learning algorithms. For example, semantic analysis may be performed on the text to determine a context of each piece of medical information material such as the field of research, the particular pharmaceuticals studied, results of the study, etc. Of particular importance is recognition of standardized biochemistry naming conventions including, but not limited to, stock nomenclature, International Union of Pure and Applied Chemistry (IUPAC) conventions, and simplified molecular-input line-entry system (SMILES) and FASTA text-based molecule representations. The data extraction engine 212 feeds the extracted data to a knowledge graph constructor 213, which constructs a knowledge graph 215 based on the information in the data, representing informational entities (e.g., proteins, molecules, diseases, study results, people) as vertices of a graph and relationships between the entities as edges of the graph. Biochemical databases 214 or similar sources of information may be used to supplement the graph with known properties of proteins, molecules, physiological effects, etc. Separately from the knowledge graph 215, vector representations of proteins, molecules, interactions, and other information may be represented as vectors 216, which may either be extracted from the knowledge graph 215 or may be created directly from data received from the data extraction engine 212. The link between the knowledge graph 215 and the data analysis engine 220 is merely an exemplary abstraction. The knowledge graph 215 does not feed into the models directly but rather the data contained in a knowledge graph structured database is used to train the models. The same exemplary abstraction applies between the vector extraction and embedding 216 and the data analysis engine 220.

The data analysis engine 220 utilizes the information gathered, organized, and stored in the data curation platform 210 to train machine learning algorithms at a training stage 230 and conduct analyses in response to queries and return results based on the analyses at an analysis stage 240. The training stage 230 and analysis stage 240 are identical, whereas the analysis stage 240 has already completed training. In this embodiment, the data analysis engine 220 comprises a dual analysis system which combines the outputs of a trained graph-based machine learning algorithm 241 with the outputs of a trained sequence-based machine learning algorithm 242. The trained graph-based machine learning algorithm 241 may be any type of algorithm configured to analyze graph-based data, such as graph traversal algorithms, clustering algorithms, or graph neural networks.

At the training stage 230, information from the knowledge graph 215 is extracted to provide training data in the form of graph-based representations of molecules and the known or suspected bioactivity of those molecules with certain proteins. The graph-based representations, or 3D representations in the 3D case, of the molecules and proteins and their associated bioactivities are used as training input data to a graph-based machine learning algorithm 231, resulting in a graph-based machine learning output 233 comprising vector representations of the characteristics of molecules and their bioactivities with certain proteins. Simultaneously, a sequence-based machine learning algorithm is likewise trained, but using information extracted 216 from the knowledge graph 215 in the form of vector representations of protein segments and the known or suspected bioactivity of those protein segments with certain molecules. The vector representations of the protein segments and their associated bioactivities are used to train the concatenated outputs 235, as well as the machine learning algorithms 231, 232, 233, 234. In this embodiment, the graph-based machine learning outputs 233 and the sequence-based machine learning outputs 234 are concatenated to produce a concatenated output 235, which serves to strengthen the learning information from each of the separate machine learning algorithms. In this and other embodiments, the concatenated output may be used to re-train both machine learning algorithms 233, 234 to further refine the predictive abilities of the algorithms.

At the analysis stage, a query in the form of a target ligand 244 and a target protein 245 are entered using an exploratory drug analysis (EDA) interface 250. The target ligand 244 is processed through the trained graph-based machine learning algorithm 241 which, based on its training, produces an output comprising a vector representation of the likelihood of interaction of the target ligand 244 with certain proteins and the likelihood of the bioactivity resulting from the interactions. Similarly, the target protein 245 is processed through the trained sequence-based machine learning algorithm 242 which, based on its training, produces an output comprising a vector representation of the likelihood of interaction of the target protein 245 with certain ligands and the likelihood of the bioactivity resulting from the interactions. The results may be concatenated 243 to strengthen the likelihood information from each of the separate trained machine learning algorithms 241, 242.

Figure 3:
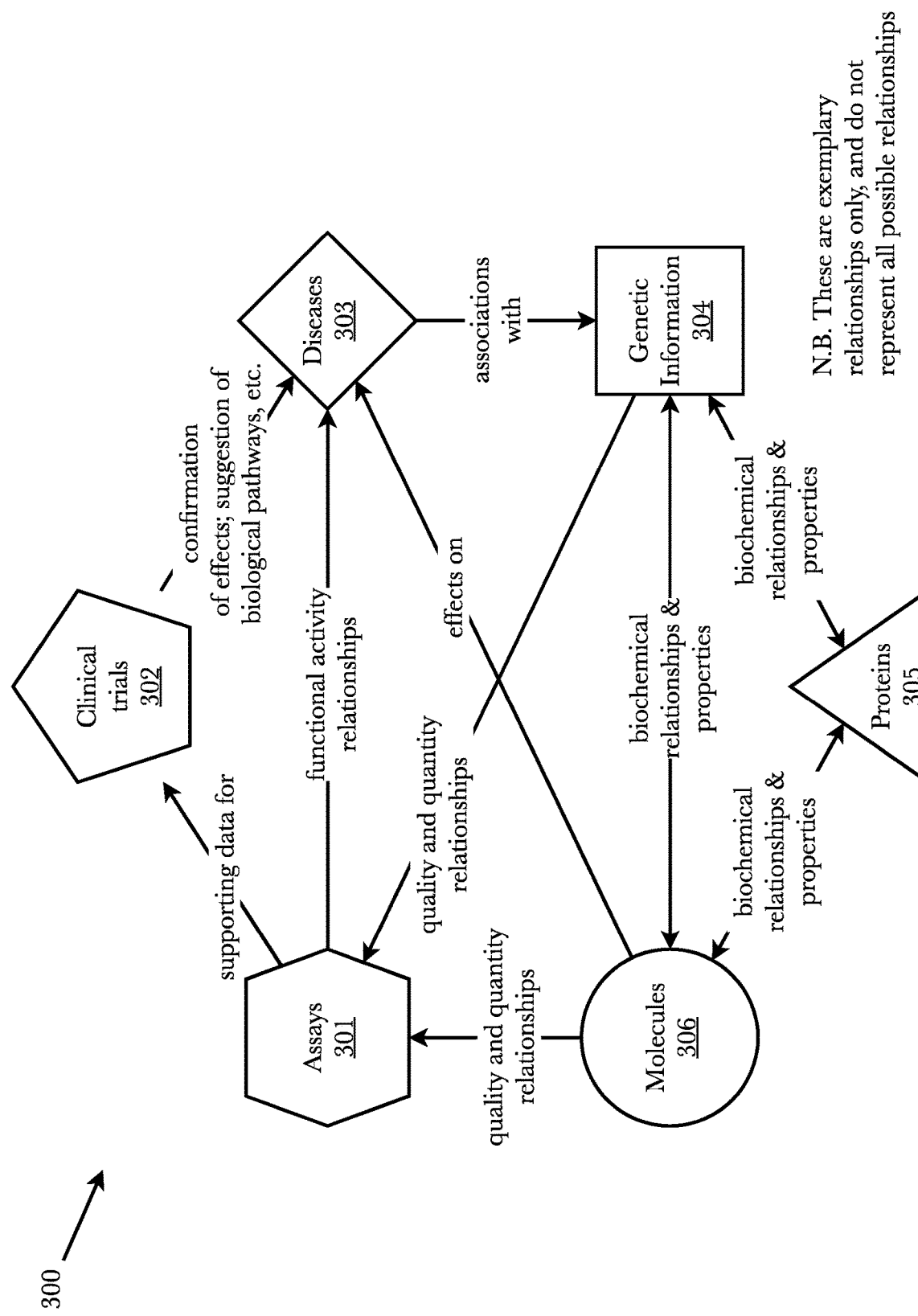
FIG. 3 is a relational diagram illustrating several types of information that may be included in a knowledge graph for a pharmaceutical research system and exemplary relations between those types of information.

FIG. 3 is a relational diagram 300 illustrating several types of information that may be included in a knowledge graph for a pharmaceutical research system and exemplary relations between those types of information. In this example, six types of information are shown with indications of certain relevant relationships and interactions that may be represented in a knowledge graph containing these types of information. The six types of information in this example are chosen to be of particular relevance to pharmaceutical research, and in particular to the analysis of, and prediction of, biochemical properties of proteins and ligands as they relate to disease. Proteins 305 and molecules (ligands) 306 are the primary types of information, as their biochemical relationships and properties determine effects on diseases 303. Genetic information 304 will have an influence on the production of specific proteins 305 and the association with certain diseases 303. Assays 301 will provide information about the quality and quantity relationships of proteins 350 and molecules 306, which provides supporting data for clinical trials 302 and for functional activity relationships with certain diseases 303. Clinical trials 302 provide confirmation of physiological effects and suggestion of biological pathways related to diseases. While this simplified diagram does not purport to show all types of data, that may be included or all relationships that may be relevant, it does show certain important types of data and major relevancies that may be included in a knowledge graph to be used for a pharmaceutical research system.

Figure 4:
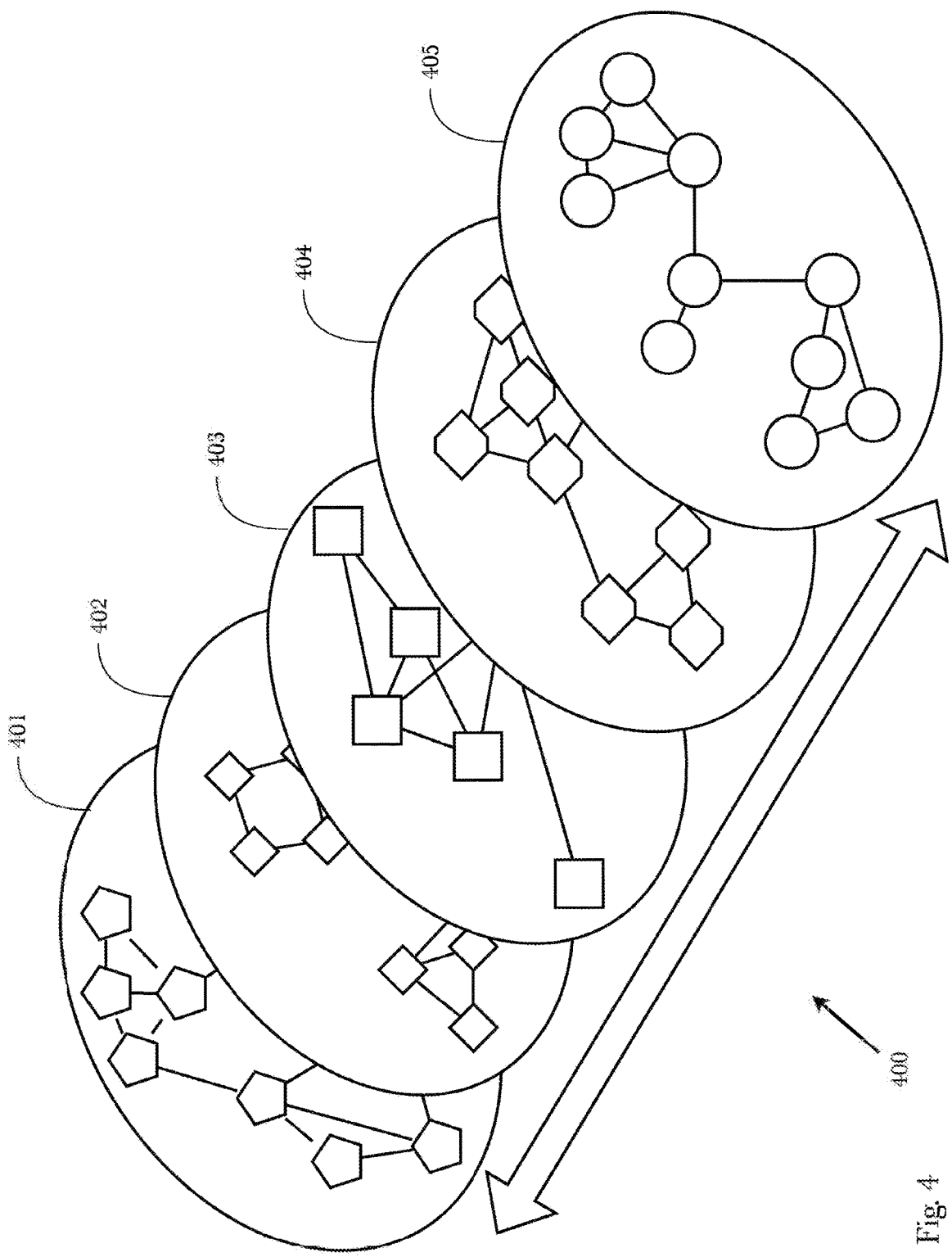
FIG. 4 is a diagram illustrating the conceptual layering of different types of information in a knowledge graph.

FIG. 4 is a diagram illustrating the conceptual layering 400 of different types of information in a knowledge graph. While knowledge graphs are not necessarily constructed in layers, each type of information included in a knowledge graph may be conceived as a layer of information in the knowledge graph and each layer may be analyzed to determine clustering and other relationships within the layer. For example, proceeding with the types of information shown in FIG. 3, the knowledge graph can be conceived of as having layers for clinical trials 401, diseases 402, genetic information 403, assays 404, molecules 405, etc. Relationships such as clustering can be seen at each layer, and can be analyzed separately, if necessary. However, in a knowledge graph, connections between the information at each layer are made and relationships between the information at each layer can be analyzed.

Figure 5:
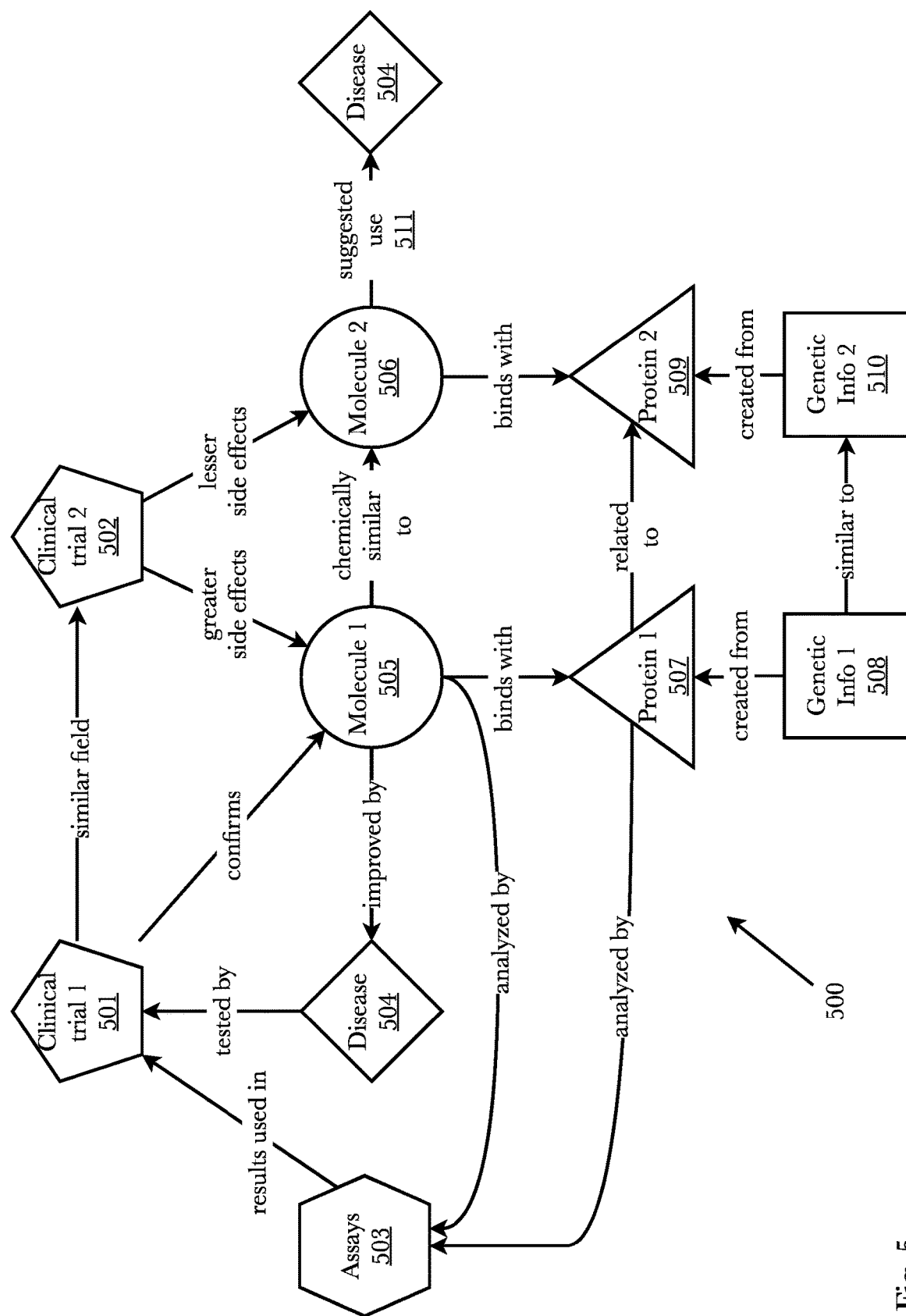
FIG. 5 is a relational diagram illustrating the use of a knowledge graph to predict usefulness of a molecule in treating a disease.

FIG. 5 is a relational diagram illustrating the use of a knowledge graph to predict usefulness of a molecule in treating a disease 500. In this example, a first molecule 505 is known to bind with a first protein 507 which is produced from a first, set of genetic information 508. A clinical trial 501 confirmed that the first molecule 505 is effective in treating a disease 504. The clinical trial 501 used information from assays 503 that were performed on the first molecule 505 and the first protein 507. A query has been submitted to the system to identify a second molecule 506 that may also be effective in treating 511 the same disease 504, but with fewer side effects. Using a knowledge graph containing the types of information shown in FIG. 3, and a graph-based machine learning algorithm, the system identifies a second molecule 506 that binds with a second protein 509 which is produced from a second set of genetic information 510. The system determines a number of similarities and relationships between the first molecule 505 and the second molecule 506, including that the first molecule 505 is chemically similar to the second molecule 506, the protein 507 with which the first molecule 505 binds is related to the second protein 509 with which the second molecule 506 binds, and the genetic information (DNA strands) 508 that produces the first protein 507 are similar to the genetic information 510 that produces the second protein 509. Thus, the system determines that the second molecule 506 is likely to have a similar effect on the disease 504 as the first molecule 505. Further, the system identifies a second clinical trial 502 that suggests that the second molecule 506 has lesser side effects than the first molecule 505. As the second molecule 506 meets the query criteria, it is returned as a response to the query.

Figure 6:
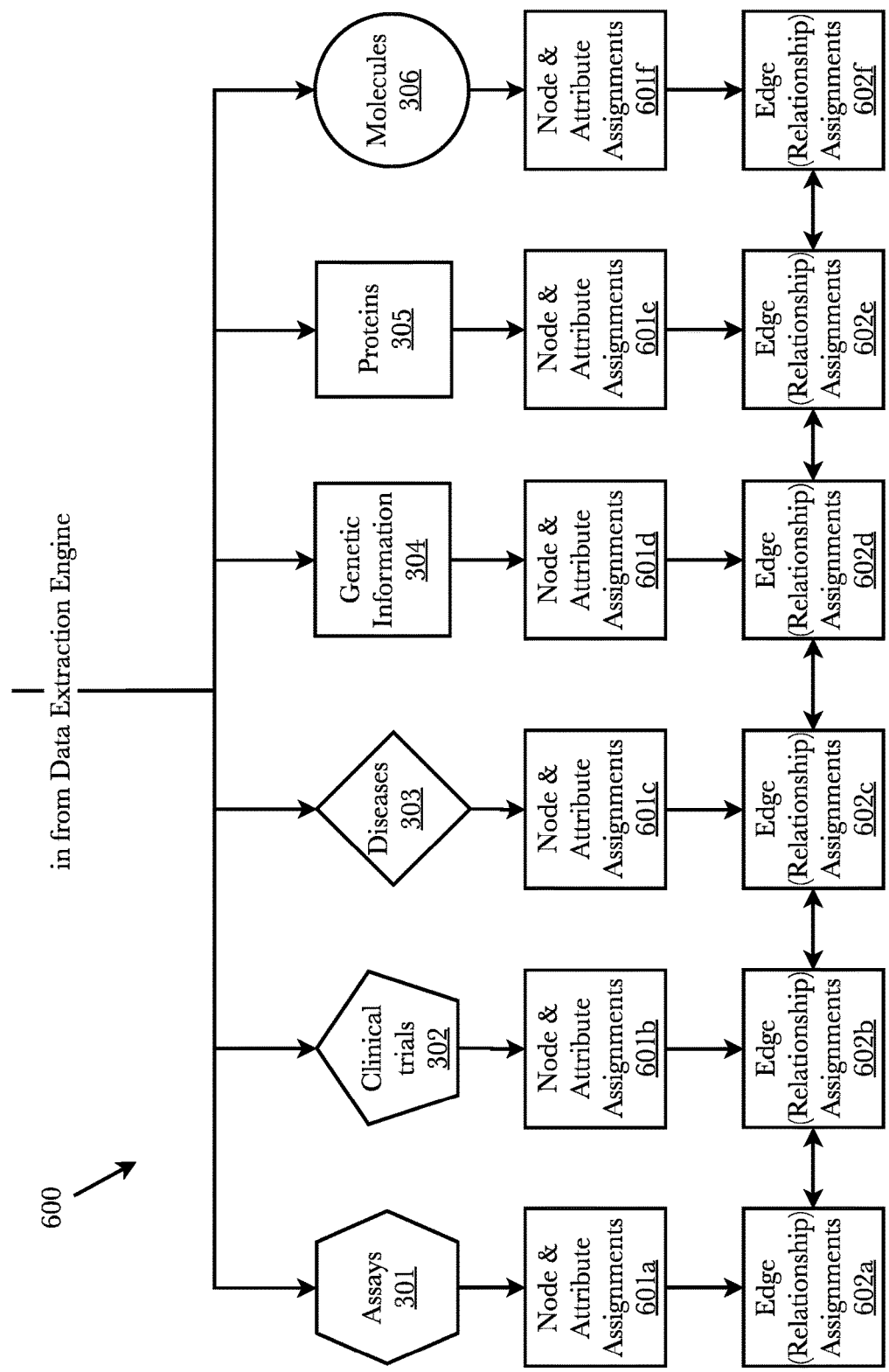
FIG. 6 is a diagram illustrating an exemplary process for combining various types of information into a knowledge graph suitable for a pharmaceutical research system.

FIG. 6 is a diagram illustrating an exemplary process 600 for combining various types of information into a knowledge graph suitable for a pharmaceutical research system. As data is received from a data extraction engine in each of several categories of data (in this example, six categories: assays 301, clinical trials 302, diseases 303, genetic information 304, proteins 305, and molecules 306) nodes are assigned to each entity identified in each category and attributes of the entity are assigned to the node 601a-f. Attributes of the nodes entity are information describing the characteristics of the nodes/entity. For example, in some embodiments, attributes of nodes related to molecules are in the form of an adjacency matrix which represents the molecule as relationships between the atoms of the molecule. After nodes have been assigned to all identified entities 601a-f, the relationships between entities are assigned, both within the category of knowledge and between all other categories of knowledge 602a-f. As a simple example of the process, assume that a certain molecule 306 is identified during data extraction. A nod created for the molecule and attributes are assigned to the molecule/ node in the form of an adjacency matrix representing the molecule as a series of relationships between the atoms of the molecule. Through a series of assays 301 and clinical studies 302, it is known that the molecule binds with a particular protein 305, and is effective in treating a certain disease 303, to which individuals with certain genetic information 304 are susceptible. Nodes are assigned to each of the assays 301, clinical trials 302, diseases 303, proteins 305, and genetic information 304 identified as being associated with the molecule, and edges are established between the nodes reflecting the relevant relationships such as: the molecule binds with the protein, the genetic information is associated with the disease, the clinical trials indicate that the disease is treatable by the molecule, and so on.

Figure 7:
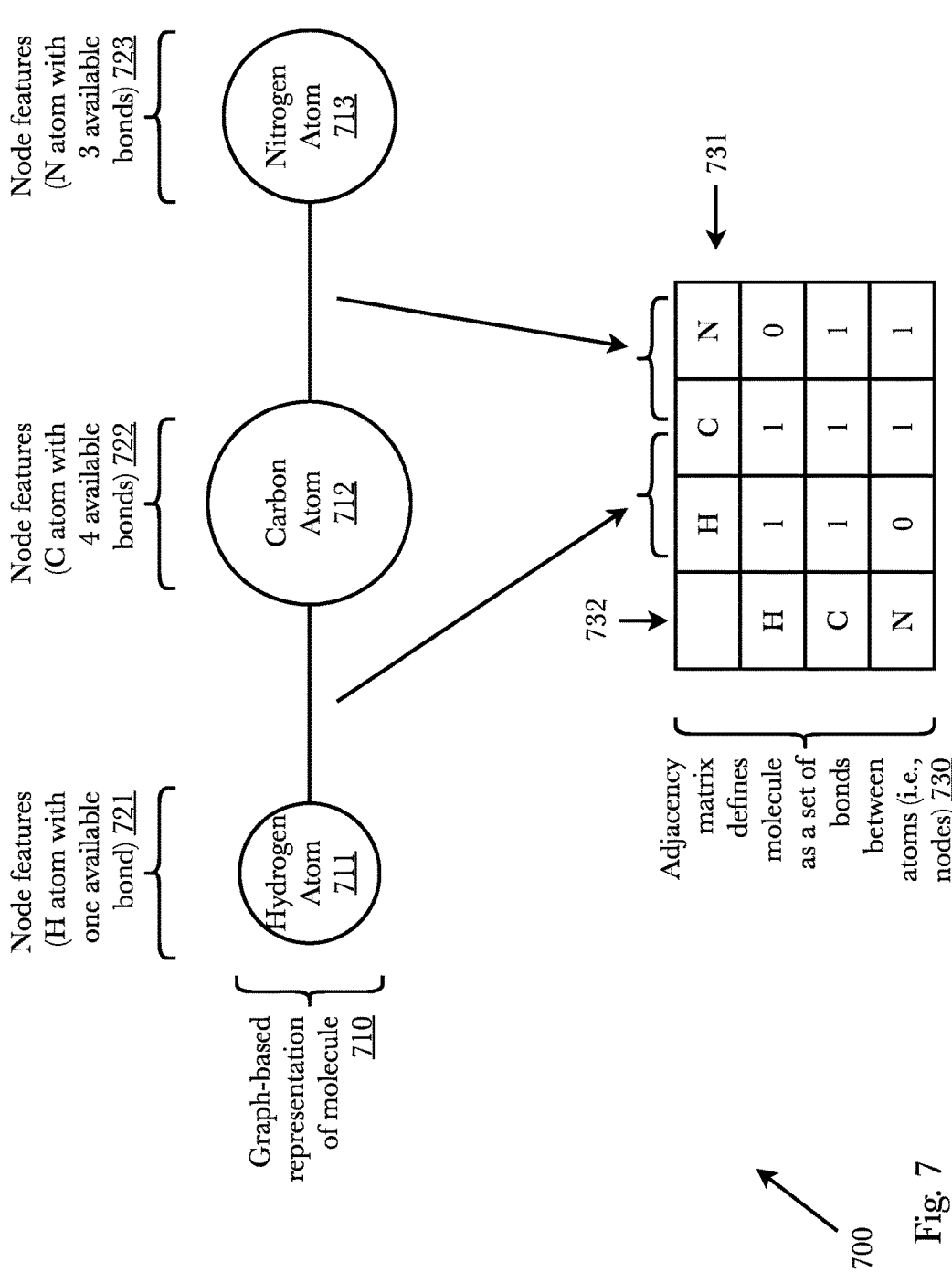
FIG. 7 is a diagram illustrating an exemplary graph-based representation of molecules as simple relationships between atoms using a matrix of adjacencies.

FIG. 7 is a diagram illustrating an exemplary graph-based representation of molecules as simple relationships between atoms using a matrix of adjacencies 700, wherein atoms are represented as nodes and bonds between the atoms are represented as edges. Representation of molecules as a graph is useful because it provides a molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule. Each molecule represented in the matrix comprises a dimensionality and features that describe the type of bond between the atoms. According to one embodiment, all bonds within the graph hold the same value, e.g., 1. However, in other embodiments, bonds may be differentiated such as hydrogen bonds having a value of 3, or by having the bond feature dimension exist in each cell.

In this example, a simple hydrogen cyanide molecule is shown as a graph-based representation 710. A hydrogen cyanide molecule consists of three atoms, a hydrogen atom 711, a carbon atom 712, and a nitrogen atom 713. Its standard chemical formula is HCN. Each atom in the molecule is shown as a node of a graph. The hydrogen atom 711 is represented as a node with node features 721 comprising the atom type (hydrogen) and the number of bonds available (one). The carbon atom 712 is represented as a node with node features 722 comprising the atom type (carbon) and the number of bonds available (four). The nitrogen atom 713 is represented as a node with node features 723 comprising the atom type (nitrogen) and the number of bonds available (three). The node features 721, 722, 723 may each be stated in the form of a matrix.

The relationships between the atoms in the molecule are defined by the adjacency matrix 730. The top row of the adjacency matrix 731 shows all of the atoms in the molecule, and the left column of the matrix 732 shows a list of all possible atoms that can be represented by the matrix for a given set of molecules. In this example, the top row 731 and left column 732 contain the same list of atoms, but in cases where multiple molecules are being represented in the system, the left column may contain other atoms not contained in the particular molecule being represented. The matrix shows, for example, that the hydrogen atom 711 is connected to the carbon atom 712 (a "1" at the intersection of the rows and columns for H and C) and that the carbon atom 712 is connected to the nitrogen atom 713 (a "1" at the intersection of the rows and columns for C and N). In this example, each atom is also self-referenced (a "1" at the intersection of the rows and columns for H and H, C and C, and N and N), but in some embodiments, the self-referencing may be eliminated. In some embodiments, the rows and columns may be transposed (not relevant where the matrix is symmetrical, but relevant where it is not).

Figure 8:
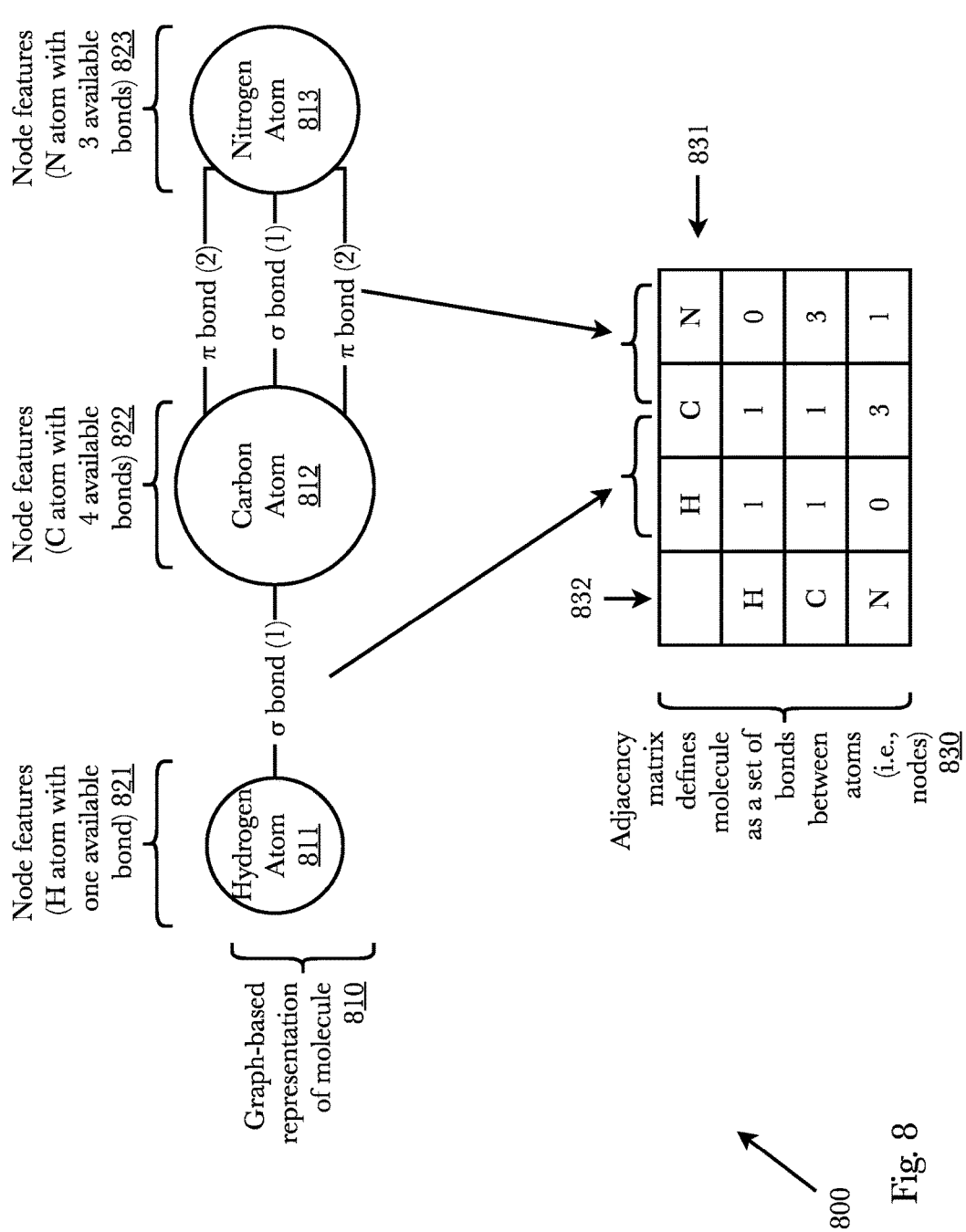
FIG. 8 is a diagram illustrating an exemplary graph-based representation of molecules as relationships between atoms using a matrix of adjacencies wherein the type bonds are distinguished.

FIG. 8 is a diagram illustrating an exemplary graph-based representation of molecules as relationships between atoms using a matrix of adjacencies 800, wherein atoms are represented as nodes and bonds between the atoms are represented as edges, and wherein the type and number of bonds are distinguished. Representation of molecules as a graph is useful because it provides a molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 810. A hydrogen cyanide molecule consists of three atoms, a hydrogen atom 811, a carbon atom 812, and a nitrogen atom 813. Its standard chemical formula is HCN. Each atom in the molecule is shown as a node of a graph. The hydrogen atom 811 is represented as a node with node features 821 comprising the atom type (hydrogen) and the number of bonds available (one). The carbon atom 812 is represented as a node with node features 822 comprising the atom type (carbon) and the number of bonds available (four). The nitrogen atom 813 is represented as a node with node features 823 comprising the atom type (nitrogen) and the number of bonds available (three). The node features 821, 822, 823 may each be stated in the form of a matrix.

The relationships between the atoms in the molecule are defined by the adjacency matrix 830. The top row of the adjacency matrix 831 shows all of the atoms in the molecule, and the left column of the matrix 832 shows a list of all possible atoms that can be represented by the matrix for a given set of molecules. In this example, the top row 831 and left column 832 contain the same list of atoms, but in cases where multiple molecules are being represented in the system, the left column may contain other atoms not contained in the particular molecule being represented. The matrix shows, for example, that the hydrogen atom 811 is connected to the carbon atom 812 (a "1" at the intersection of the rows and columns for H and C) and that the carbon atom 812 is connected to the nitrogen atom 813 (a "3" at the intersection of the rows and columns for C and N). In this example, the number of bonds between atoms is represented by the digit in the cell of the matrix. For example, a 1 represents a single bond, whereas a 3 represents a triple bond. In this example, each atom is also self-referenced (a "1" at the intersection of the rows and columns for H and H, C and C, and N and N), but in some embodiments, the self-referencing may be eliminated. In some embodiments, the rows and columns may be transposed (not relevant where the matrix is symmetrical, but relevant where it is not).

Figure 9:
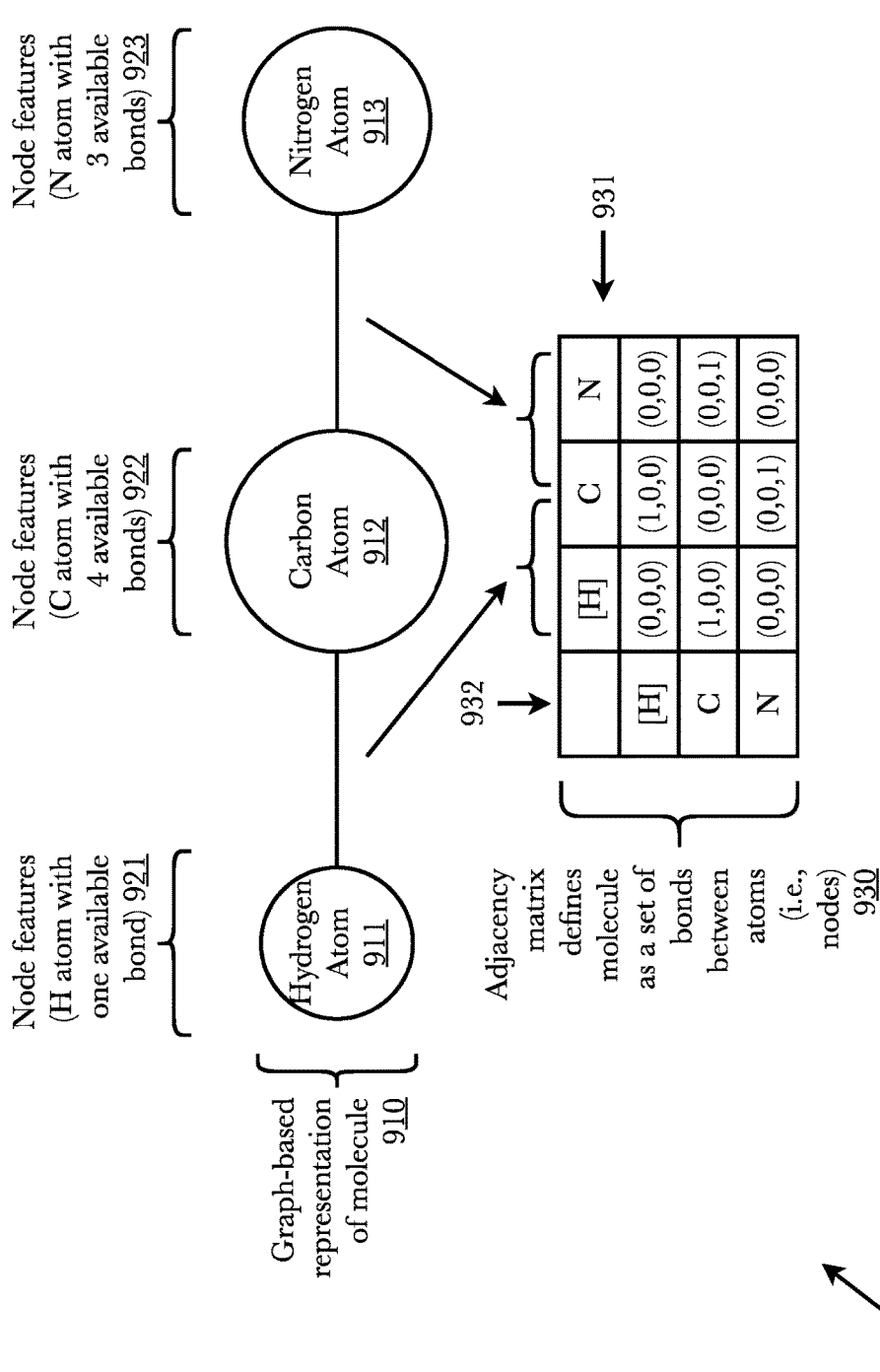
FIG. 9 is a diagram illustrating an exemplary graph-based representation of molecules as relationships between atoms using a matrix of adjacencies using SMILES string encoding and one-hot vectors indicating the types of bonds between atoms.

FIG. 9 is a diagram illustrating an exemplary graph-based representation of molecules as relationships between atoms using a matrix of adjacencies 900, wherein atop is are represented as nodes and bonds between the atoms are represented as edges, and wherein the matrix of adjacencies uses a SMILES string encoding of the molecule and one-hot vector representations of the type of bonds between atoms in the molecule. Representation of molecules as a graph is useful because it provides a molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 910. A hydrogen cyanide molecule consists of three atoms, a hydrogen atom 911, a carbon atom 912, and a nitrogen atom 913. Its SMILES representation text string is [H]C#N, with the brackets around the H indicating an element other than an organic element, and the representing a triple bond between the C and N. Each atom in the molecule is shown as a node of a graph. The hydrogen atom 911 is represented as a node with node features 921 comprising the atom type (hydrogen) and the number of bonds available (one). The carbon atom 912 is represented as a node with node features 922 comprising the atom type (carbon) and the number of bonds available (four). The nitrogen atom 913 is represented as a node with node features 923 comprising the atom type (nitrogen) and the number of bonds available (three). The node features 921, 922, 923 may each be stated in the form of a matrix 930.

In this example, the top row 931 and left column 932 contain the same list of atoms, but in cases where multiple molecules are being represented in the system, the left column may contain other atoms not contained in the particular molecule being represented. The matrix shows, for example, that the hydrogen atom 811 is connected to the carbon atom 812 with a single bond (the one-hot vector "(1,0,0)" at the intersection of the rows and columns for H and C) and that the carbon atom 812 is connected to the nitrogen atom 813 with a triple bond (the one-hot vector "(0,0,1)" at the intersection of the rows and columns for C and N). In this example, the number of bonds between atoms is represented by a one-hot vector in the cell of the matrix. For example, a 1 in the first dimension of the vector (1,0,0) represents a single bond, whereas a 1 in the third dimension of the vector (0,0,1) represents a triple bond. In this example, self-referencing of atoms is eliminated, but self-referencing may be implemented in other embodiments, or may be handled by assigning self-referencing at the attention assignment stage. In some embodiments, the rows and columns may be transposed (not relevant where the matrix is symmetrical, but relevant where it is not).

Figure 14:
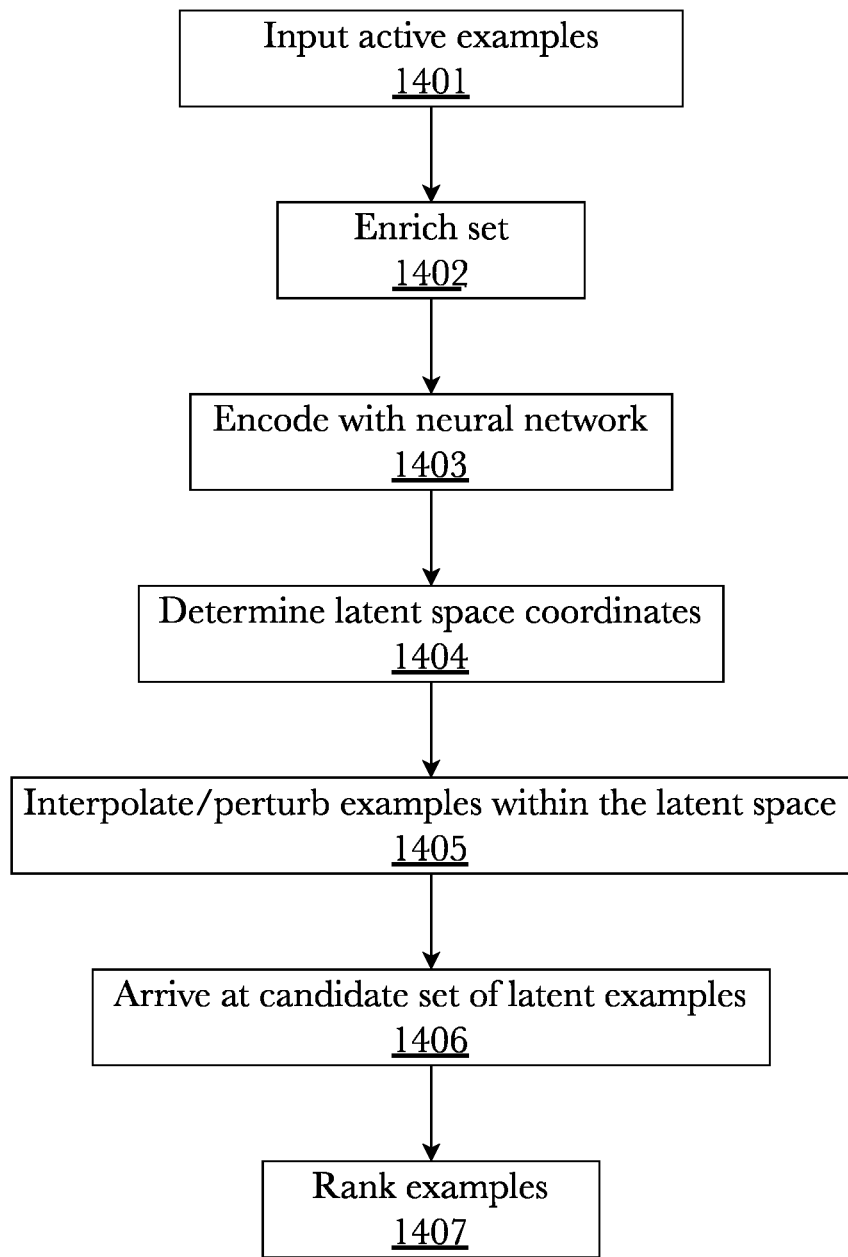
FIG. 14 is a flow diagram illustrating an exemplary method for active example generation.

FIG. 14 is a flow diagram illustrating an exemplary method for active example generation. According to a general methodology description, generating active examples (i.e., chemically valid ligand-receptor pairs) is performed by the first step of gathering known active examples from databases, web-crawlers, and other sources previously described in past figures 1401. Active examples may then be enriched to fill in missing data, supplement, append or otherwise enhance the training data 1402. A specific example of enrichment may be finding similar compounds with the same properties as a target molecule or that responds to known ligands in the same fashion. With the enhanced training data (i.e., enriched active examples) gathered, it is fed into a neural network (NN) 1403. A consideration must be noted that many machine learning algorithms exist, and that this method may work with many NN models or other machine learning algorithms and is not limited to the ones disclosed herein.

The neural networks build a model from e training data the case of using an autoencoder (or a variational autoencoder), the encoder portion of the neural network reduces the dimensionality of the input molecules, learning a model from which the decoder portion recreates the input molecule. The significance of outputting e same molecule as the input is that the decoder may then be used as a generative function for new molecules. One aspect of a generative decoder module is that the learned model (i.e., protein-ligand atom-features according to one embodiment) lies in a latent space 1404. Sampled areas of the latent space are then interpolated and perturbed 1405 to alter the model such that new and unique latent examples 1406 may be discovered. Other ways to navigate the latent space exist, Gaussian randomization as one example, that may be used in other embodiments of the invention. Furthermore, libraries, other trained models, and processes exist that may assist in the validation of chemically viable latent examples within the whole of the latent space; processing the candidate set of latent examples through a bioactivity model, as one example 1407.

Regarding retrosynthesis for de novo drug design, two approaches are described below. A first approach begins with preprocessing all the SMILES representations for reactants and products to convert to canonical form (SMILES to Mol & Mol to SMILES through a cheminformatics toolkit), remove duplicates & clean the data, augmenting SMILE equivalents via enumeration. Then, transformer models are used with multiple attention heads and a k-beam search is set up. Further, the models are conformed by optimizing on producing long-term reactants, ensuring the models are robust to different representations of a molecule, providing intrinsic recursion (using performers), and including further reagents such as catalysts and solvents.

A second approach begins with augmenting the transformer model with a hyper-graph approach. Starting with an initial node of the graph as the query molecule and recursively: the molecule with highest upper-bound confidence (UCB) score is selected (specifically, the UCB is adapted to trees generation UCT), the node is expanded (if this node is not terminal), and expansions from that node are simulated to recover a reward. Rewards are backpropagated along the deque of selected nodes, and the process is repeated until convergence. Here UCB is used as a form of balancing exploration-exploitation, where X is the reward, n is the number of times the parent node has been visited, j denotes the child node index, and $C_p$ (>0) is an exploration constant. In one embodiment, the model may be constrained to a rewarding a node when its children are accessible, wherein other embodiments may use rewards such as molecular synthesis score, Log P, synthesis cost, or others known in the art.

$$UCT = \overline{X}_j + 2C_p\sqrt{\frac{2\ln n}{n_j}}$$

According to one aspect of the second approach, transformer models are optimized so that they produce a molecule that can be formed with another molecule. However, these models should be optimized with the aim of producing reactants which are going to recursively deconstruct into accessible molecules. Hence, adding reinforcement learning finetuning to force the transformer model to not only produce reactants which are plausible but to produce reactants which lead to favorable retrosynthetic routes.

Figure 15:
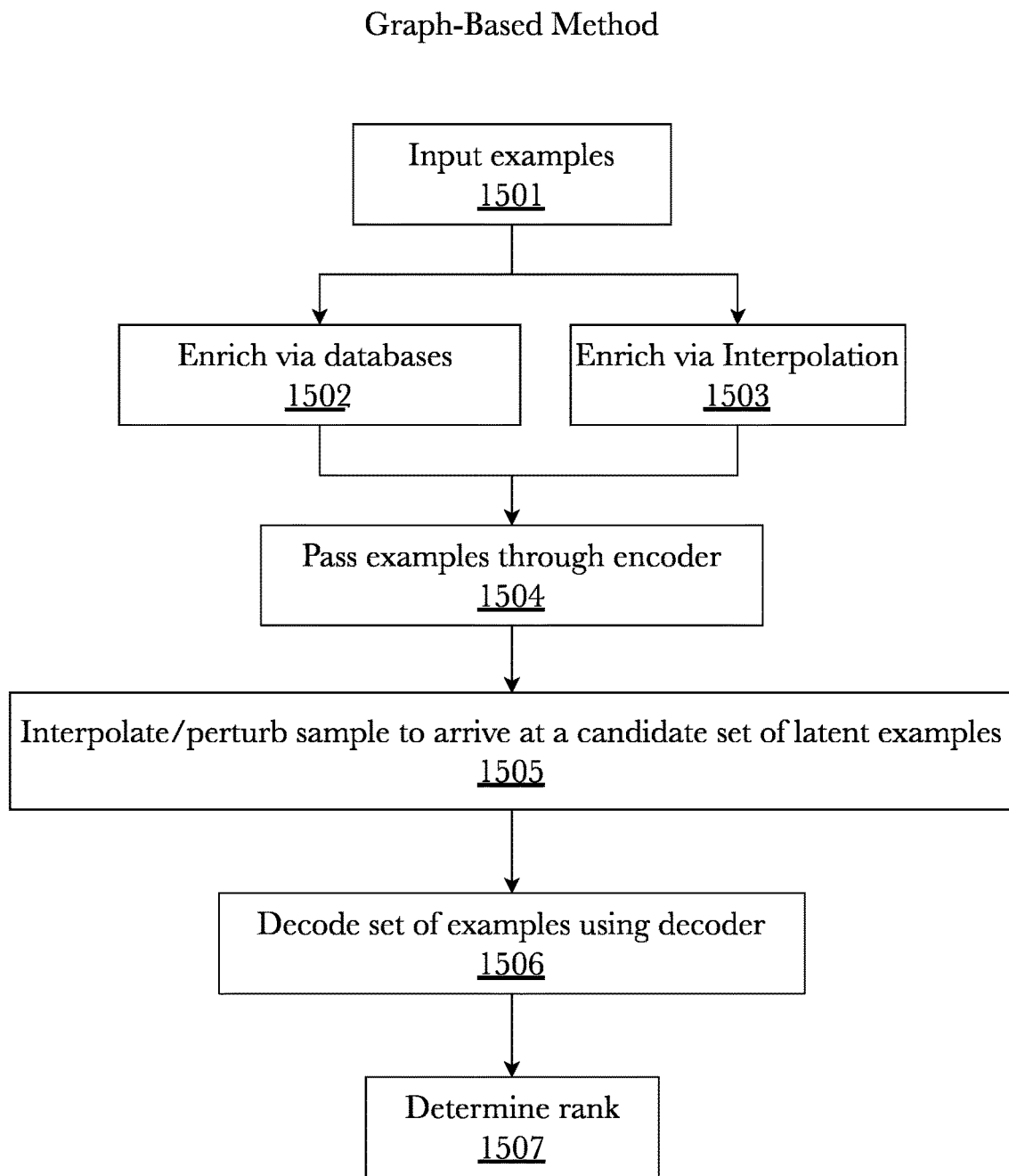
FIG. 15 is a flow diagram illustrating an exemplary method for active example generation using a graph-based approach.

FIG. 15 is a flow diagram illustrating an exemplary method for active example generation using a graph-based approach. According to a first preferred embodiment of active example generation, where a graph-based method is used, active molecules are input (via a WebApp according to one aspect) as SMILES representations 1501. This involves training an autoencoder to obtain a fixed-dimensional representation of SMILES and may further be reused for the bioactivity model. Additionally, standard SMILES encoding fails to capture all pertinent information relating to the atoms (e.g., bond length). Consequently, enumeration may be used to improve the standard SMILES model where enumeration is an equivalent to data augmentation via rotation, therefore by having different SMILES representations of the same molecule from different orientations the missing information is captured. Other enumeration methods may be used where data is necessary but missing. The enumerated SMILES encoding used may comprise one-hot encodings of atom type, atom degree, valence, hybridization, and chirality as well as formal charge and number of radical electrons. Bond types (single, double, triple, and aromatic), bond length, and bond conjugation with ring and stereo features are also captured.

Enrichment of the input data may be performed by searching through data sets for compounds through specific tags (e.g., anti-viral) 1502. Additionally, the enrichment process may be used if the training data lacks any descriptive parameters, whereby databases, web-crawlers, and such may fill in the missing parameters 1502. Enrichment may also occur where data is sparse by interpolating between known molecules 1503. This enriched training data is then captured in node and edge feature matrices. Some embodiments may use matrices comprising a node feature matrix, N, of shape (No_Atoms, No_Features_Atom) and edge feature (adjacency) tensor, A, of shape (No_Atoms, No_Atoms, No_Features_Bond). A reminder to the reader that a tensor's rank is its matrix dimensionality.

Figure 20:
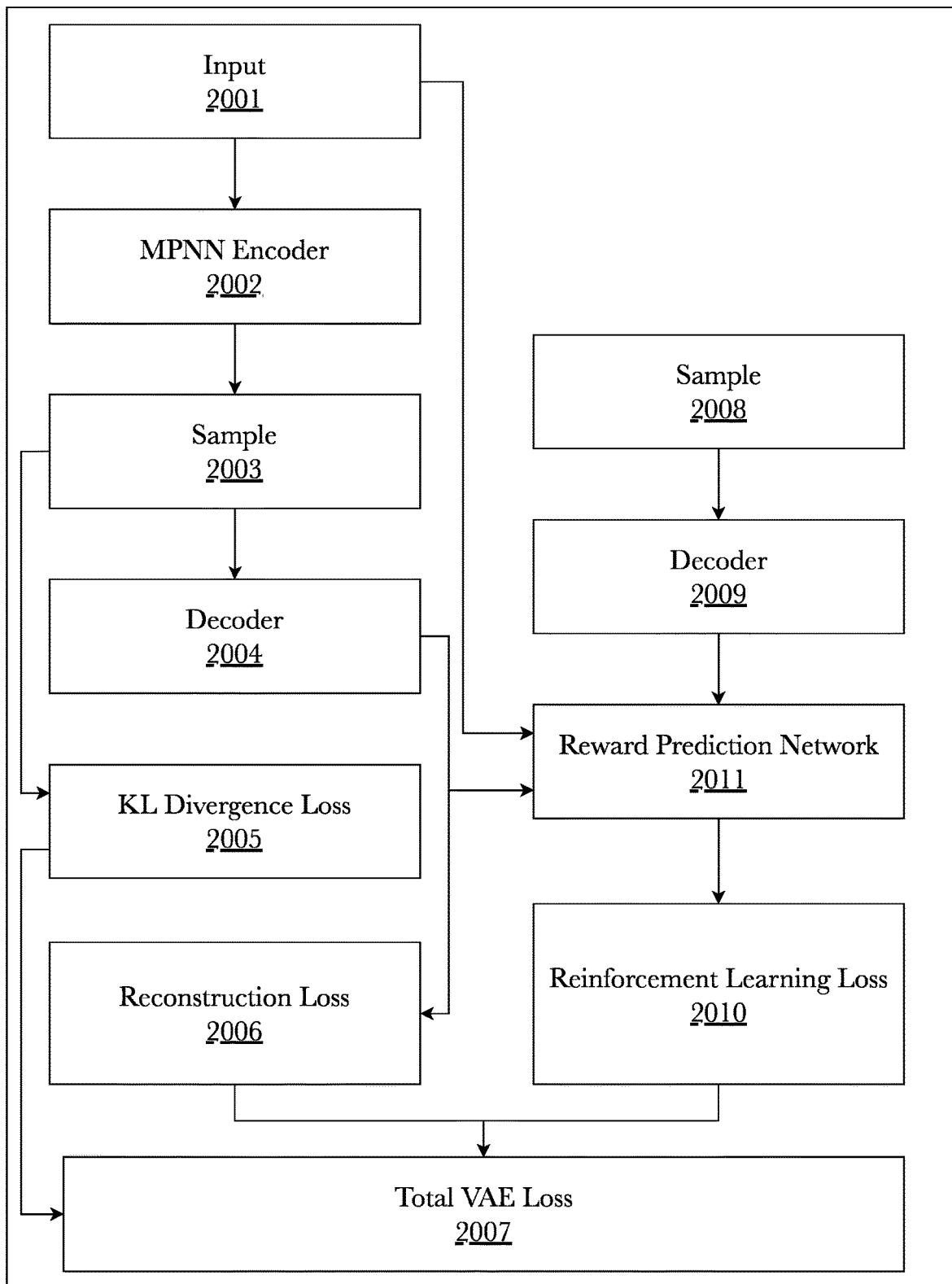
FIG. 20 is a block diagram of an overall model architecture of a system for de novo drug discovery according to one embodiment.

The next step is to pass examples through a variational autoencoder (VAE) together with a reinforcement learning component to build the bill model 1504 (See FIG. 20). The encoder of this embodiment consists of a message passing neural network, which given node and edge features is designed to learn a hidden representation of a molecule (i.e., a readout vector). This is done by continuously aggregating neighboring node and edge information through a process called message passing. The readout vector is subsequently split into the mean and variance vectors which serve and as the parameters of the posterior distribution from the sampling. The model may learn a latent distribution that governs molecular properties and provide a decoder which can construct chemically valid molecules from samples of the prior 1505. Latent samples are passed through a sequence of dense layers, after which the two different matrices (node feature matrix, N and edge feature tensor) are used to reconstruct the node feature and edge feature matrices. Keeping with the example described in the paragraph above, these two matrices must have the shapes of (No Atoms, No Node Features) and (No Atoms, No Atoms, No Edge Features) respectively. This may be enforced by using a maximum number of allowed atoms to reconstruct. Further, an additional entry for each of the encoded feature distributions may be allowed, which represents the possibility of No Atom/No Feature. The node and edge feature matrices are compared using an approximate graph matching procedure which looks at atom types, bond types, atom-bond-atom types.

Reinforcement learning may be used in parallel to provide an additional gradient signal, checking that decoded molecules are chemically valid using cheminformatics toolkits. In particular, samples from the prior distribution (N (0,1)) as well as posterior distribution (N (mean, std)) are decoded 1506 and their validity is evaluated 1507. If the cheminformatics toolkit is non-differentiable, then a reward prediction network (a separate MPNN encoder) that is trained to predict the validity of an input graph may be used. Together, these components provide an end to end, fully differentiable framework for training. Other choices for data can be QM9, or any other database that is considered valid.

According to one aspect, in order to make use of more molecules, alternative reconstructability criteria may be used to ensure a chemical similarity threshold instead of perfect reconstruction. For example, encoding and decoding several times and using a molecule if its reconstruction has a chemical similarity above a certain threshold may result in a greater number of reconstruct able molecules.

New molecules may also be generated via perturbation, wherein the encodings of the active molecules (i.e., the mean and log(sigma$^2$) values) are taken and Gaussian noise is added to them. A sample from the new (mean, log(sigma$^2$)) values are taken and decoded to derive novel molecules. An important hyperparameter is the magnitude of the Gaussian noise that is added to latent vectors. It is also possible to dynamically adjust the perturbation coefficient, for example, increasing it if the proportion of new molecules is low and decreasing it otherwise.

New molecules may also be generated via interpolation. To generate via interpolation, two random reconstruct able molecules are taken, computed together for an interpolation of their latent (mean, log(sigma$^2$)) representations with a random interpolation coefficient, and then decoded to get a new molecule. Generative Adversarial Networks (GANs) excel at interpolation of high dimensional inputs (e.g., images). According to one aspect, the dimension of p(z) corresponds to the dimensionality of the manifold. A method for latent space shaping is as follows: Converge a simple autoencoder on a large z, find the Principal Component Analysis (PCA) which corresponds to the 95th percentile of the "explained variance", and choose a z within that spectrum (i.e., if the first 17 components of the latent space to represent 95% of the data, choosing z of 24 is a good choice). Now, for high dimensional latent spaces with a Gaussian prior, most points lie within a hyper spherical shell. This is typically the case in multi-dimensional gaussians. To that end, SLERP (spherical linear interpolation) interpolation may be used between vectors v1 and v2. Therefore, interpolation is a direct way to explore the space between active molecules.

Figure 16:
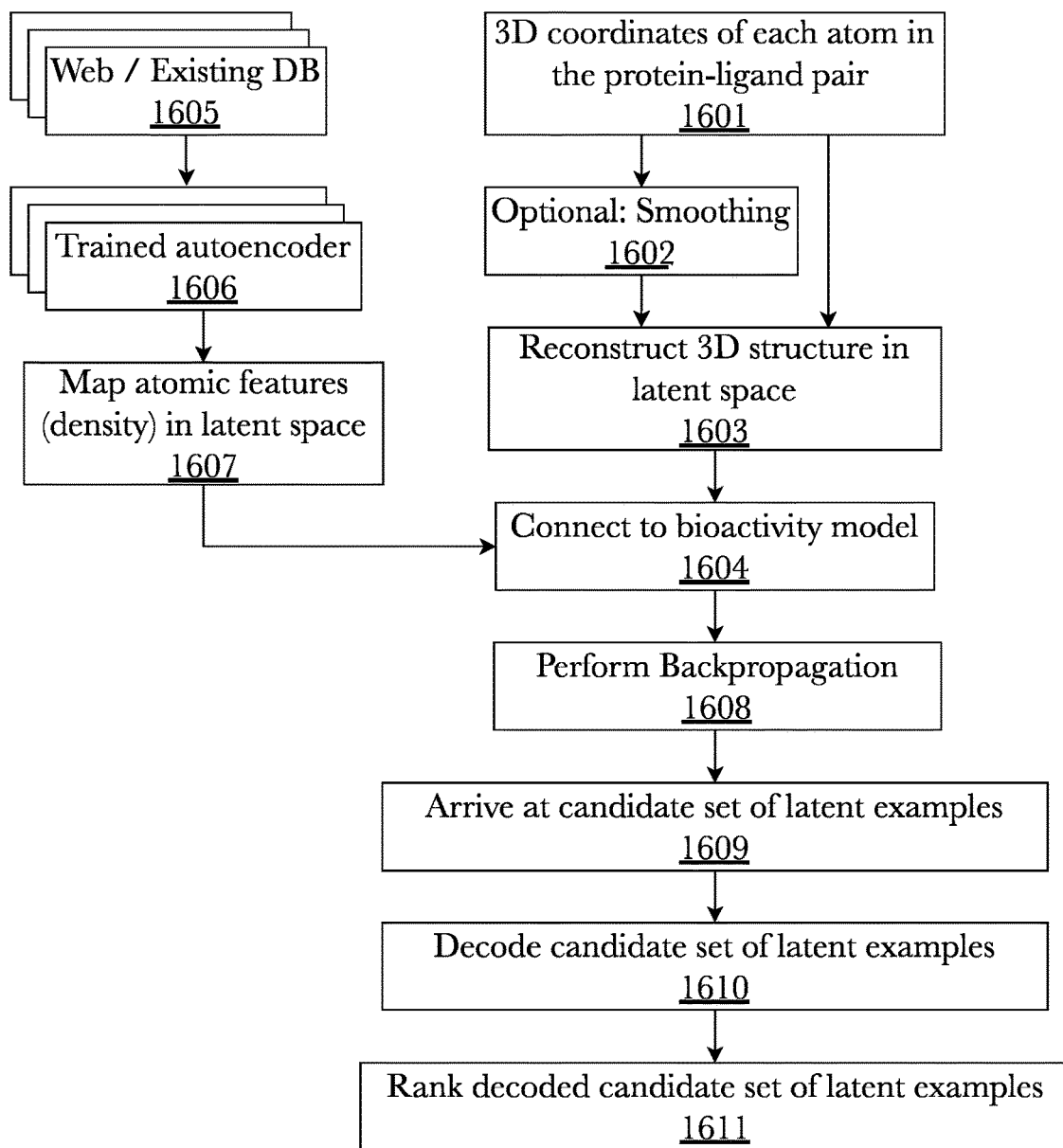
FIG. 16 is a flow diagram illustrating an exemplary method for active example generation using a 3D CNN approach.

FIG. 16 is a flow diagram illustrating an exemplary method for active example generation using a 3D CNN approach. According to an embodiment of active example generation, a 3-dimensional convolutional neural network (3D CNN) is used in which atom-type densities are reconstructed using a sequence of 3D convolutional layers and dense layers. Since the output atom densities are fully differentiable with respect to the latent space, a trained variational autoencoder (VAE) 1606 may connect to a bioactivity-prediction module 1604 comprising a trained 3D-CNN model with the same kind of atom densities (as output by the autoencoder) as the features, and then optimize the latent space with respect to the bioactivity predictions against one or more receptors. After that, the optimal point in the latent space can be decoded into a molecule with desired properties.

Three-dimensional coordinates of potential molecules 1601 are used as inputs to a neural network for 3D reconstruction in latent space 1603 (the 3D models of molecules using volumetric pixels called voxels). Underfitting due to data sparsity may be prevented by optional smoothing 1602 depending on the machine learning algorithm used. Existing molecule examples 1605 are used to train one or more autoencoders 1606 whereby the output of the decoder is used to map atomic features such as atom density in latent space 1607 in the bioactivity model 1604, wherein the bioactivity model consists of a sequence of convolutional and fully connected layers. Backpropagation 1608 (or other gradient-aided search) is performed by searching the latent space for regions that optimize the bioactivities of choice thus arriving at a set of latent examples 1609. Decoding 1610 and ranking 1611 each candidate latent example produces the most viable and best-fit to the initial desired parameters.

As an example, a VAE is trained on an enriched molecule data set until optimal reconstruction is achieved. The decoder of the VAE is used as an input to a bioactivity model, wherein the VAE input is a small molecule and the bioactivity module houses a large molecule, i.e., a protein. The behavior and interactions between the molecules are output from the bioactivity model to inform the latent space of the VAE.

Figure 17:
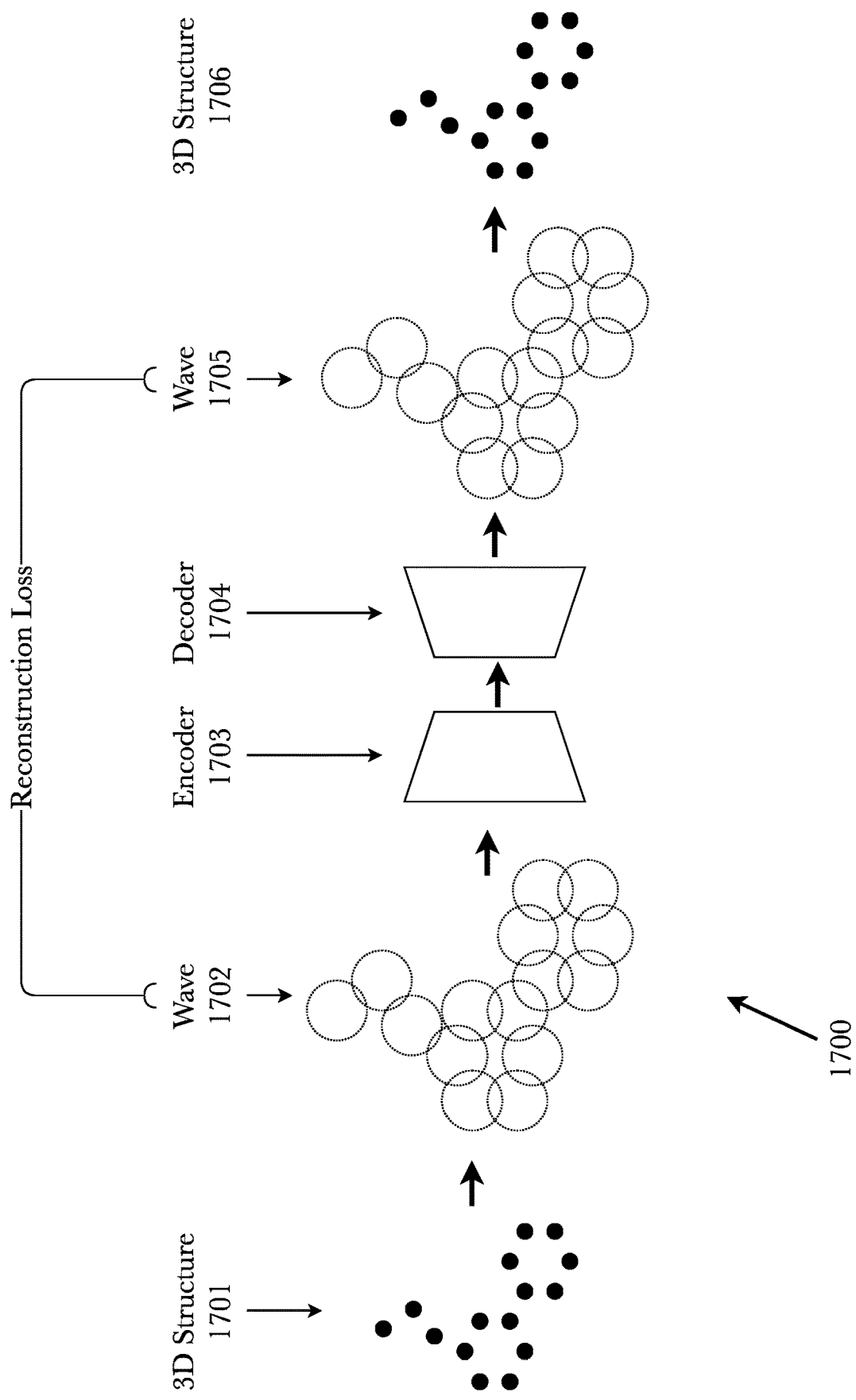
FIG. 17 is a diagram illustrating the training of an autoencoder of a 3D CNN for active example generation.

FIG. 17 is a diagram illustrating the training of an autoencoder 1700 of a 3D CNN for active example generation. In a second preferred embodiment, 3D coordinates of the atomic positions of molecules are reconstructed as smoothed (Gaussian blurring as one method) 3D models 1702, 1705 alleviating the underfitting of encoder 1703 and 3D CNN decoder 1704 models due to high data disparity. Wave representations 1702, 1705 allow voxels to convey the same information as the 3D structures 1701, 1706. One exemplary embodiment uses PyTorch, an open-source machine learning library used for applications such as computer vision and natural language processing, and is used to initially train an autoencoder.

Autoencoders 1700 may also be implemented by other programming languages and forks other than PyTorch. Additional embodiments may comprise a complex pipeline involving Generative Adversarial Networks (GANs) and a hybrid between localized non-maximal suppression (NMS) and negative Gaussian sampling (NGS) may be used to perform the mapping of smoothed atom densities to formats used to reconstruct the molecular graph. Furthermore, training autoencoders 1700 on generating active examples by deconvolution is improved by using a GPU (Graphical Processing Unit) rather than a CPU (Central Processing Unit). Using the embodiments as described above, grants input atom densities to generate detailed deconvolutions by varying noise power spectral density and signal-to-noise ratios.

As a detailed example, the generation may be done in the following steps, using any number of programming languages but is described here using the structure of Python, and by creating various functions (where functions are subsets of code that may be called upon to perform an action). The model is initialized with a trained autoencoder and a dataset of active molecules. The latent representations of the active dataset (or their distributions, in the case a variational autoencoder is used) are computed, by learning the latent space, which may comprise one function. This function may also store the statistics of the active dataset reconstructions, to compare with the statistics of the generated data later. A function which generates a set number of datapoints using the chosen generation method is also employed using a flag method within the class instance may control the generation method (e.g. "perturb", "interp"). Additional parameters for the methods, e.g. the perturbation strength, may be also controlled using instance variables. Another function may be programmed that decodes the generated latent vectors and computes statistics of the generated datasets. These statistics include the validity (percentage of the samples which are valid molecules), novelty (percentage of molecules distinct from the active dataset), and uniqueness (percentage of distinct molecules) of the dataset, as well as the molecular properties, specified in a separate function that computes the properties. Molecular properties may be added or removed to this function at will, without any changes to the rest of the code: summarized statistics and plots are inferred from the molecular properties dictionary. Results may then be summarized in two ways: by printing out the summary of the distributions and generating plots comparing the molecular properties as defined in the computer properties function of the active and generated distributions.

All variables, functions, mad preferences are only presented as exemplary and are not to be considered limiting to the invention in any way. Many avenues of training autoencoders or variational autoencoders are known to those in the art by which any number of programming languages, data structures, classes, and functions may be alternatively switched out depending on implementation and desired use.

Figure 18:
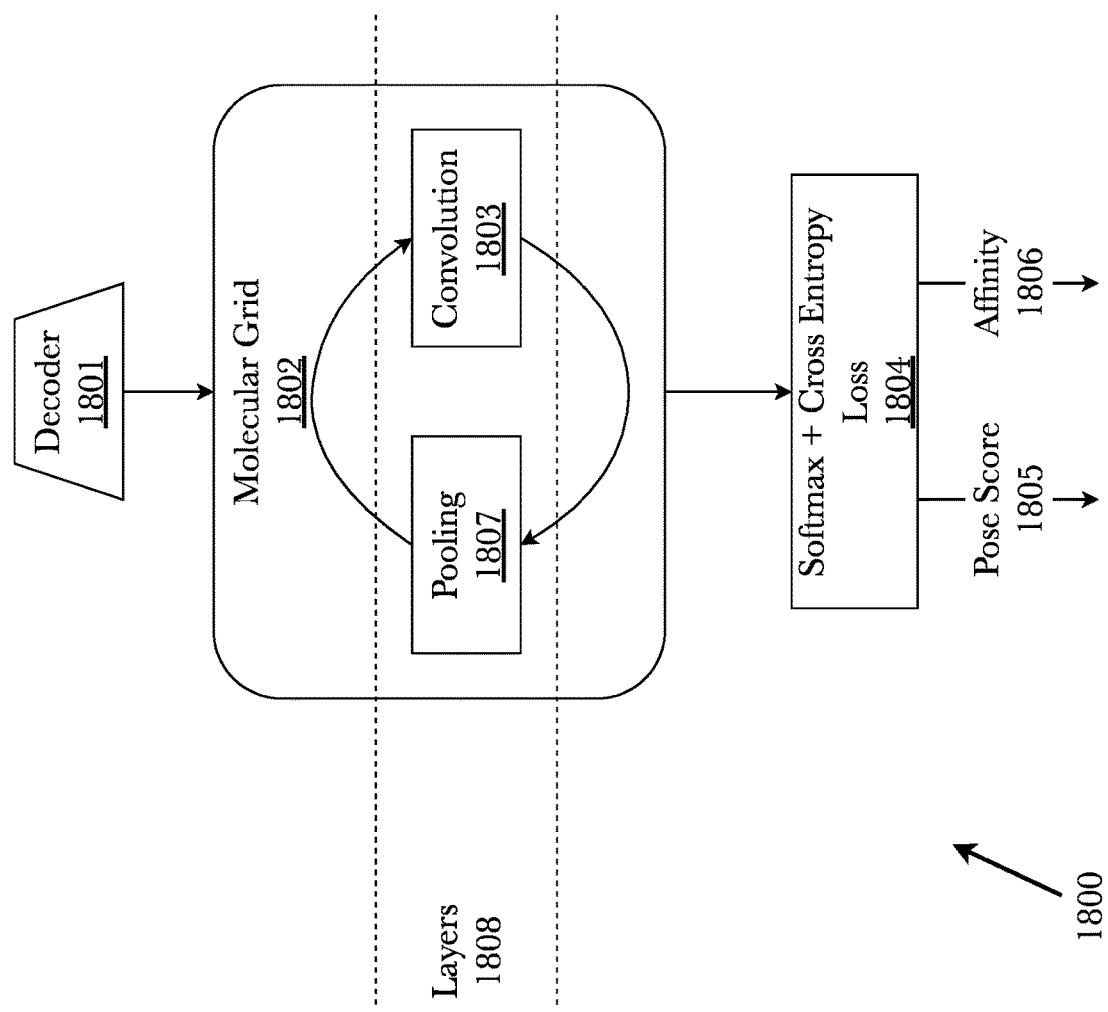
FIG. 18 is a diagram illustrating the interfacing of the decoder to the 3D-CNN bioactivity prediction model.

FIG. 18 is a diagram illustrating the interfacing of the decoder to the 3D-CNN bioactivity prediction model 1800. During training of the neural network machine learning model with inputs of a 3D grid 1802 of Gaussian-like atom type densities, the weights are iteratively modified in order to minimize the losses 1804, which is some measure of the goodness of fit of the model outputs to the training data. In an embodiment, the procedure is performed using some variation of gradient descent, where the changes applied to each weight during the update step are proportional in some way to the gradient of the loss with respect to the weight in question. The calculation of these gradients is often referred to as backpropagation, as the gradients of the loss with respect to a weight (n+1) layers removed from the model output depend, as per the chain rule, only on the gradients of the weights in the layers (0, ..., n) 1808 away from the model output 1805, 1806, and they are therefore calculated first in the layer closest to the model output and loss, the results of which are used both to update the weights and to calculate the gradients of the loss 1804 with respect to weights further back in the model.

Layers 1808 may perform a function with some parameters and some inputs, as long as the computation performed by a layer 1807/1803 has an analytic derivative of the output with respect to the layer parameters (the faster to compute, the better) These parameters may then be learned with backpropagation. The significance of using voxelated atom-features as inputs to a bioactivity model (as in the case of a 3D CNN) is that the loss can be differentiated not only with respect to the layer weights, but also with respect to the input atom features.

According to one aspect, various cheminformatics libraries may be used as a learned force-field for docking simulations, which perform gradient descent of the ligand atomic coordinates with respect to the binding affinity 1806 and pose score 1805 (the model outputs). This requires the task of optimizing the model loss with respect to the input features, subject to the constraints imposed upon the molecule by physics (i.e., the conventional intramolecular forces caused for example by bond stretches still apply and constrain the molecule to remain the same molecule). Attempting to minimize the loss 1804 directly with respect to the input features without such constraints may end up with atom densities that do not correspond to realistic molecules. To avoid this, one embodiment uses an autoencoder that encodes/decodes from/to the input representation of the bioactivity model, as the compression of chemical structures to a smaller latent space, which produces only valid molecules for any reasonable point in the latent space. Therefore, the optimization is performed with respect to the values of the latent vector, then the optima reached corresponds to real molecules.

Application of this comprises replacing the input of a trained bioactivity model with a decoder 1801 portion of a trained 3D CNN autoencoder, which effectively 'lengthens' the network by however many layers 1808 are contained within this decoder. In the case of a 3D CNN bioactivity model, the 3D CNN autoencoder would thus form the input of the combined trained models. This embodiment allows both differentiable representations which also have an easily decodable many-to-one mapping to real molecules since the latent space encodes the 3D structure of a particular rotation and translation of a particular conformation of a certain molecule, therefore many latent points can decode to the same molecule but with different arrangements in space. The derivative of the loss with respect to the atom density in a voxel allows for backpropagation of the gradients all the way through to the latent space, where optimization may be performed on the model output(s) 1805, 1806 with respect to, not the weights, but the latent vector values.

Following this optimization, the obtained minima can be decoded back into a real molecule by taking the decoder output and transforming the atom-densities into the best-matching molecular structure. During optimization of the latent space, it is likely that some constraints must be applied to the latent space to avoid ending up in areas that decode to nonsensical atom densities.

FIG. 20 is a block diagram of an overall model architecture of a system for de novo drug discovery according to one embodiment. The exemplary model described herein is a variational autoencoder (VAE) 2001-2007 together with a reinforcement learning (RL) component 2008-2010 for a graph-based approach. The aim of said model is to learn a latent distribution that governs molecular properties and provide a decoder 2004, 2009 which can construct chemically valid molecules from samples of the prior. With reinforcement learning 2008-2010 to provide an additional gradient signal, decoded molecules may be checked for chemical validity. Samples from the prior distribution as well as posterior distribution are decoded, and their validity is evaluated. As most cheminformatics toolkits chemical validity checking process is not differentiable, a reward prediction network (a separate MPNN encoder 2011) must be used which is trained to predict the validity of input graph 2001. Together, these components provide an end to end, fully differentiable framework for training.

Figure 21:
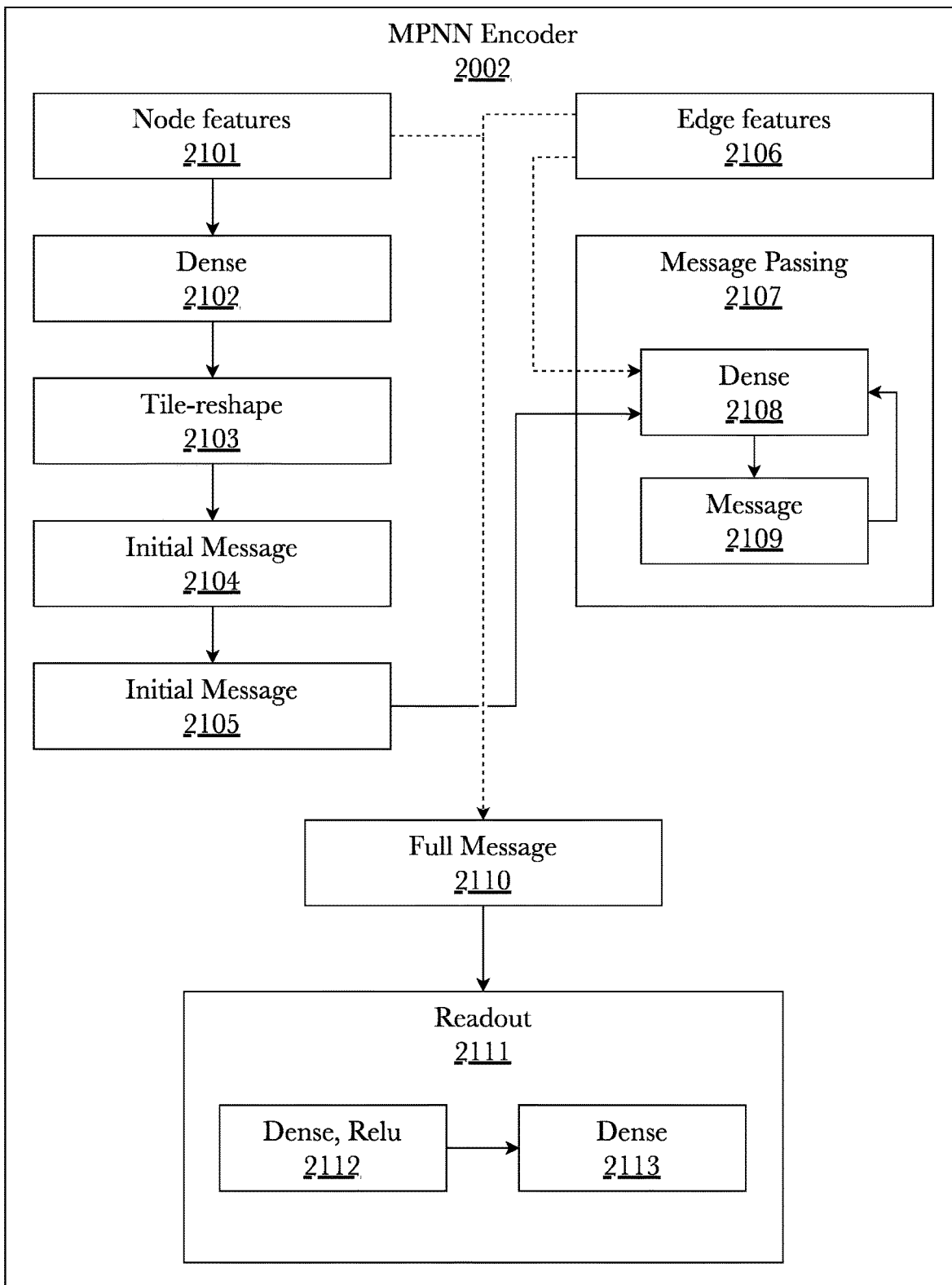
FIG. 21 is a block diagram of a model architecture of a MPNN encoder for de novo drug discovery according to one embodiment.

FIG. 21 is a block diagram of a model architecture of a MPNN encoder 2002 for de novo drug discovery according to one embodiment. MPNN Encoder 2002 consists of given node 2101 and edge features 2106 that are input to dense layers 2102, reshaped 2103, summed 2104, concatenated 2105, and circulated within a message passing neural network 2107-2110, which learns a hidden representation of a molecule (Readout vector 2111). This is done by continuously aggregating neighboring node 2101 and edge 2106 information through a process called message passing 2107. Readout vector is subsequently split in to the mean and variance vectors 2112, 2113 which serve and as the parameters of the posterior distribution from which the latent samples 2302 are sampled.

Figure 22:
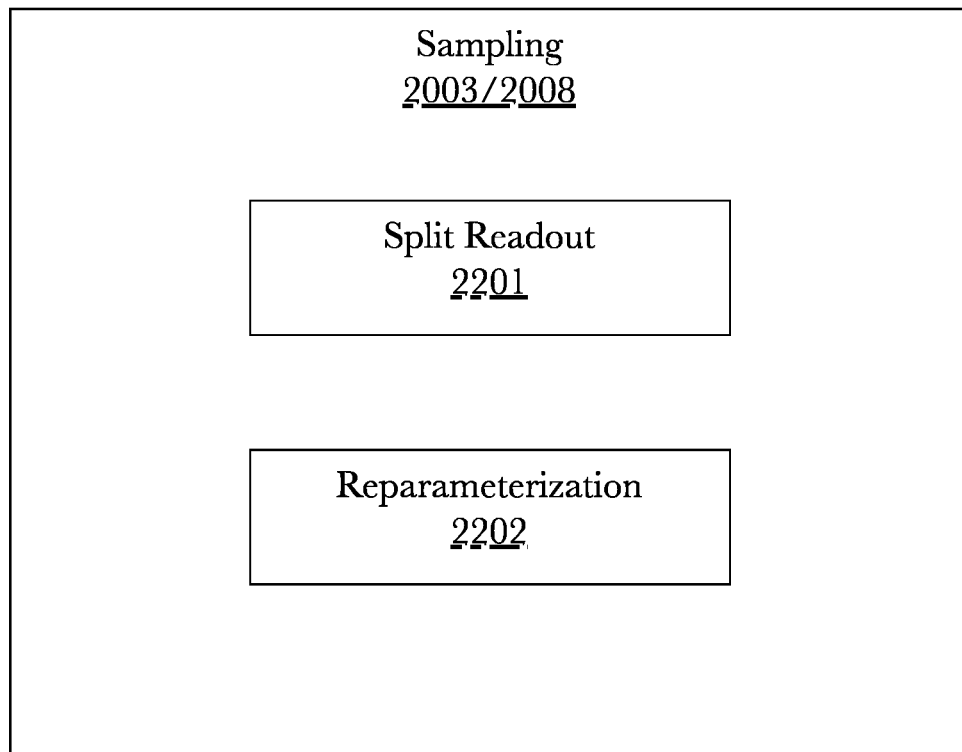
FIG. 22 is a block diagram of a model architecture of a Sampling module for de novo drug discovery according to one embodiment.

FIG. 22 is a block diagram of a model architecture of a Sampling module 2003/2008 for de novo drug discovery according to one embodiment. The sampling module comprises a split readout function 2201 that produces the mean and log(sigma) of the batch. A reparameterization function 2202 is used to get a differentiable sampling procedure and a sample of N (mean, std) using a known property of the Gaussian distribution. N (mean, std) is equal to N (0, 1) times sigma plus the mean.

Figure 23:
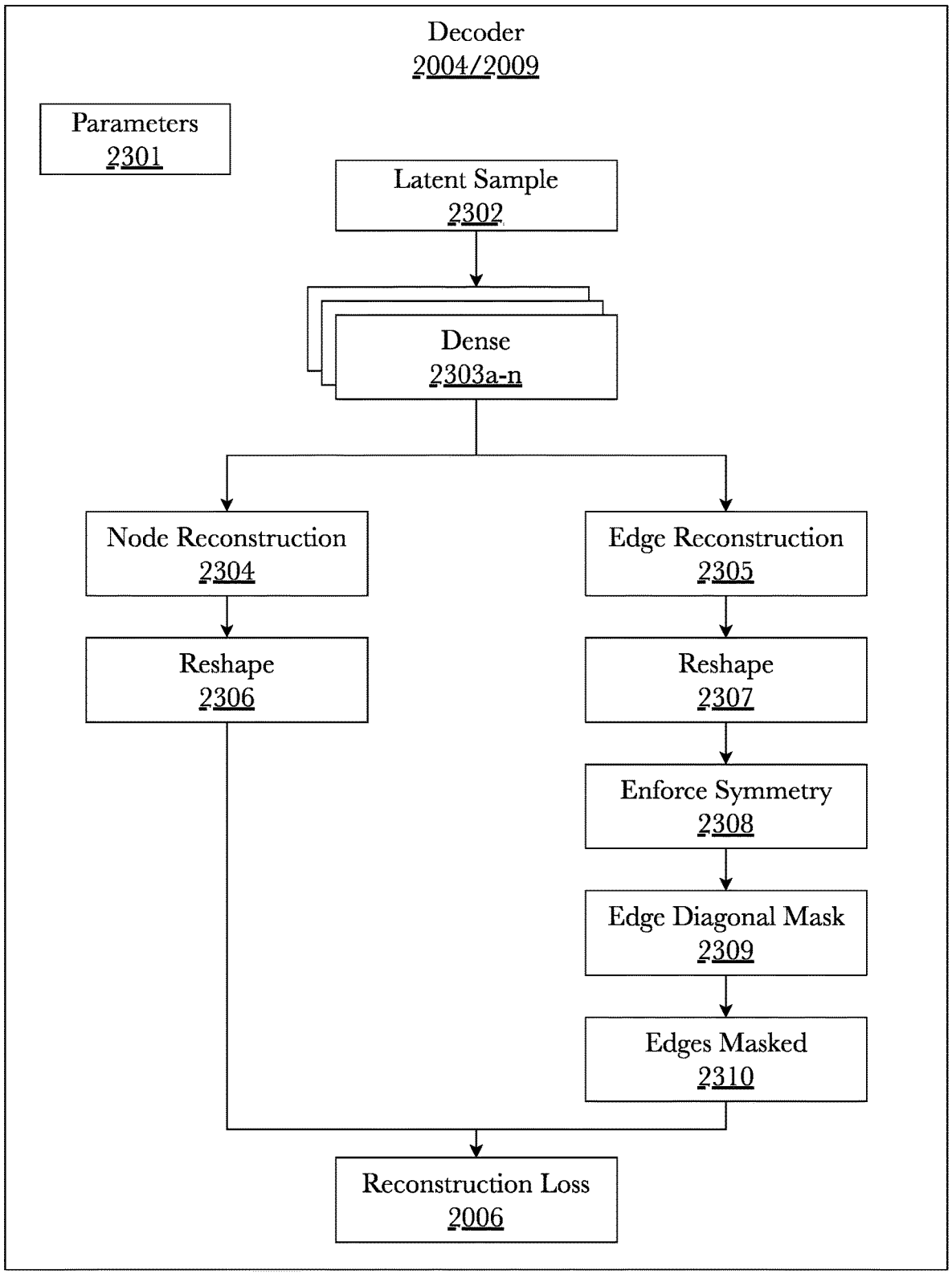
FIG. 23 is a block diagram of a model architecture of a decoder for de novo drug discovery according to one embodiment.

FIG. 23 is a block diagram of a model architecture of a decoder 2004/2009 for de novo drug discovery according to one embodiment. A decoder 2004/2009 with parameters 2301 for the maximum number of atoms to generate along with node and edge size is used to formulate the reconstruction loss 2006. Latent samples 2302 are passed through a sequence of dense layers 2303*a-n* and subsequently processed via two different matrices to reconstruct node feature 2304 and edge feature 2305 matrices. Shape functions 2306, 2307 ensure the shapes of (No Atoms, No Node Features) and (No Atoms, No Atoms, No Edge Features) respectively. Currently this is enforced by using a maximum number of allowed atoms to reconstruct. Further, an additional entry for each of the encoded feature distributions is performed, which represents the possibility of No Atom/No Feature 2308-2310. Finally, the node and edge feature matrices are compared using an approximate graph matching procedure 2006 which looks at atom types, bond types, atom-bond-atom types.

Figure 24:
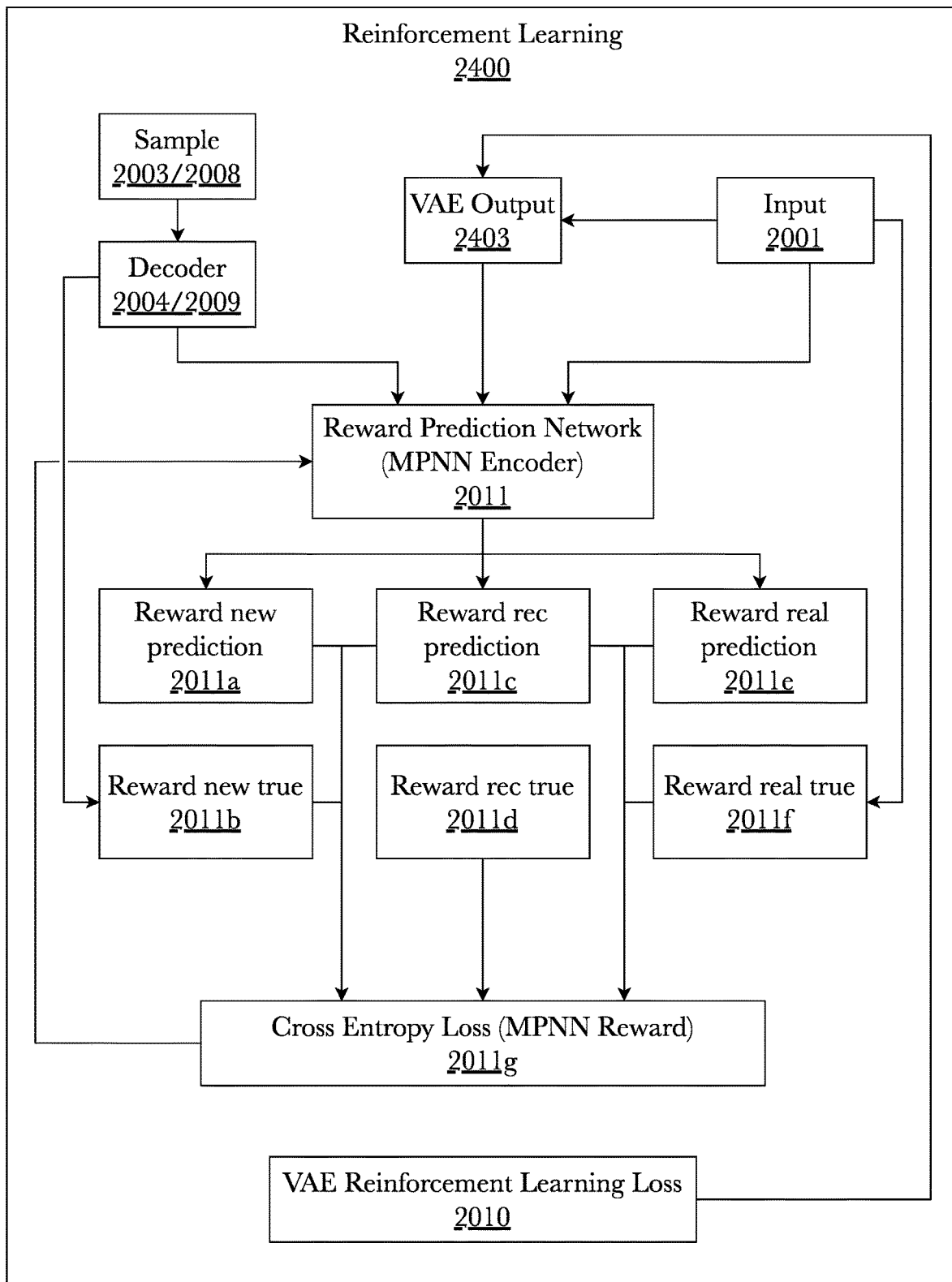
FIG. 24 is a block diagram of a model e for reinforcement learning for de novo drug discovery according to one embodiment.

FIG. 24 is a block diagram of a model architecture for reinforcement learning 2400 for de novo drug discovery according to one embodiment. The reinforcement learning 2400 as also shown in FIG. 20, comprises samples 2003/2008 and nodes and edges that inform a reward prediction network 2011. The reward prediction network 2011 receives a batch of latent examples from the decoders 2004/2009, nodes and edges from the VAE output 2403 and the input 2001, where the output of the VAE 2403 is made up of reconstructions of received nodes and edges from the input 2001. The MPNN encoder 2011 is trained to predict rewards 2011*a-f* given the nodes and edges. Cross entropy loss 2011*g* is the sum of each of the individual reward combinations 2011*a-f* and is backpropagated through the reward prediction network 2011, while the VAE RL loss 2010 is fed back into the VAE output 2403.

Figure 25:
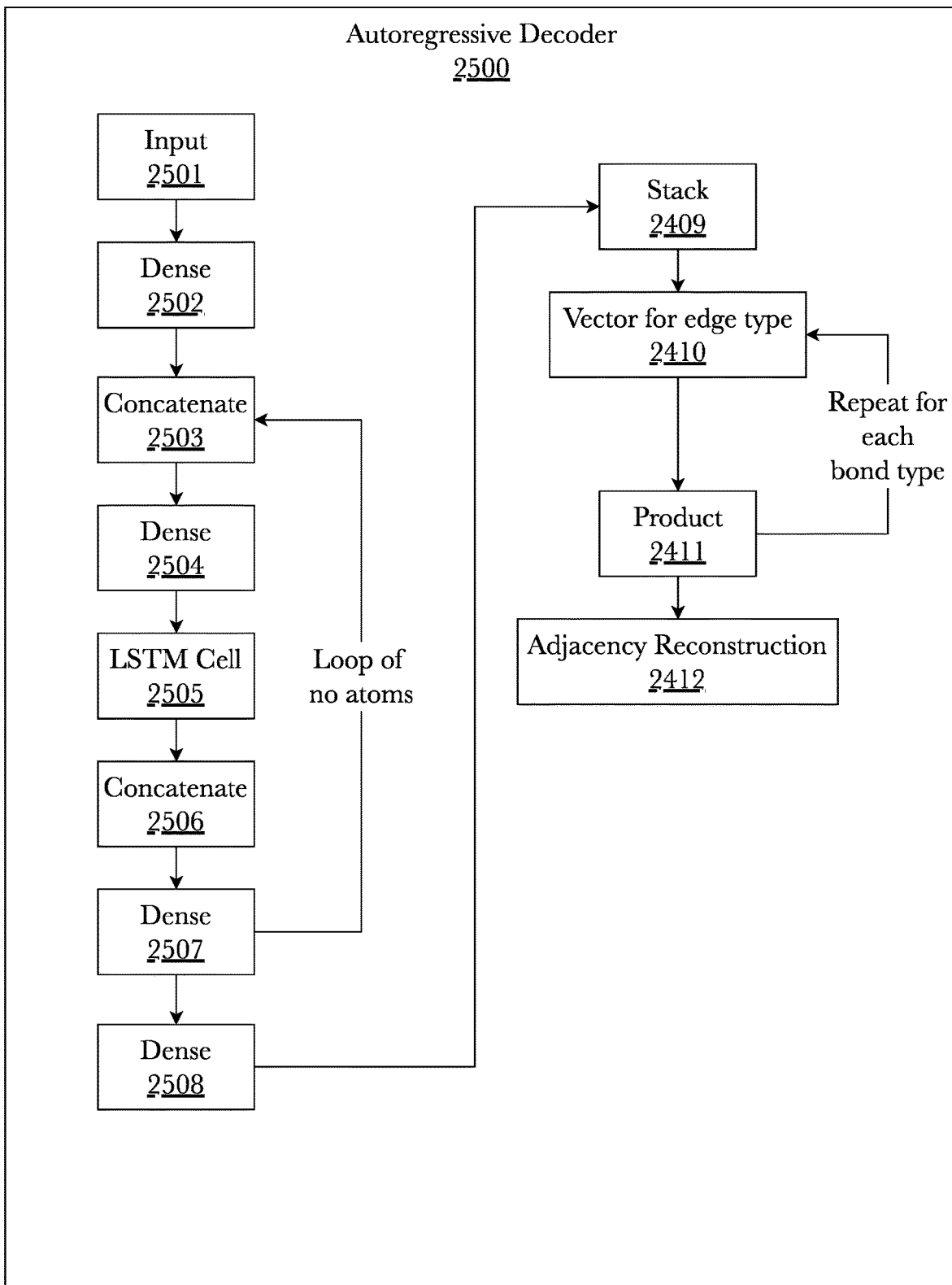
FIG. 25 is a block diagram of a model architecture of an autoregressive decoder for de novo drug discovery according to one embodiment.

FIG. 25 is a block diagram of a model architecture of an autoregressive decoder 2500 for de novo drug discovery according to one embodiment. Latent vectors of size dimension z are inputs 2501 to the autoregression decoder 2500 and subsequently calculated into dense layers 2502 where their dimensions may be expanded. A concatenation function 2503 precedes a second dense layer 2504 where pre-LSTM feature extraction occurs. After the LSTM cell function 2505, which corresponds to the LSTM recurrence operation, another concatenation occurs 2506 before a third dense layer 2507 extracts nonlinear features. The loop between the third dense layer 2507 and the first concatenation has no atoms. The fourth dense layer 2508 processes atom node features for the stack 2409 to begin node reconstruction. For each bond type a vector for the edge type is created 2410 where the product 2411 outputs probable bond types between nodes. Lastly, adjacency reconstruction 2412 is modeled by a set of edge-specific factors, (e.g., logistic sigmoid function, the corresponding diagonal vector matrix) which are learned parameters.

Figure 26:
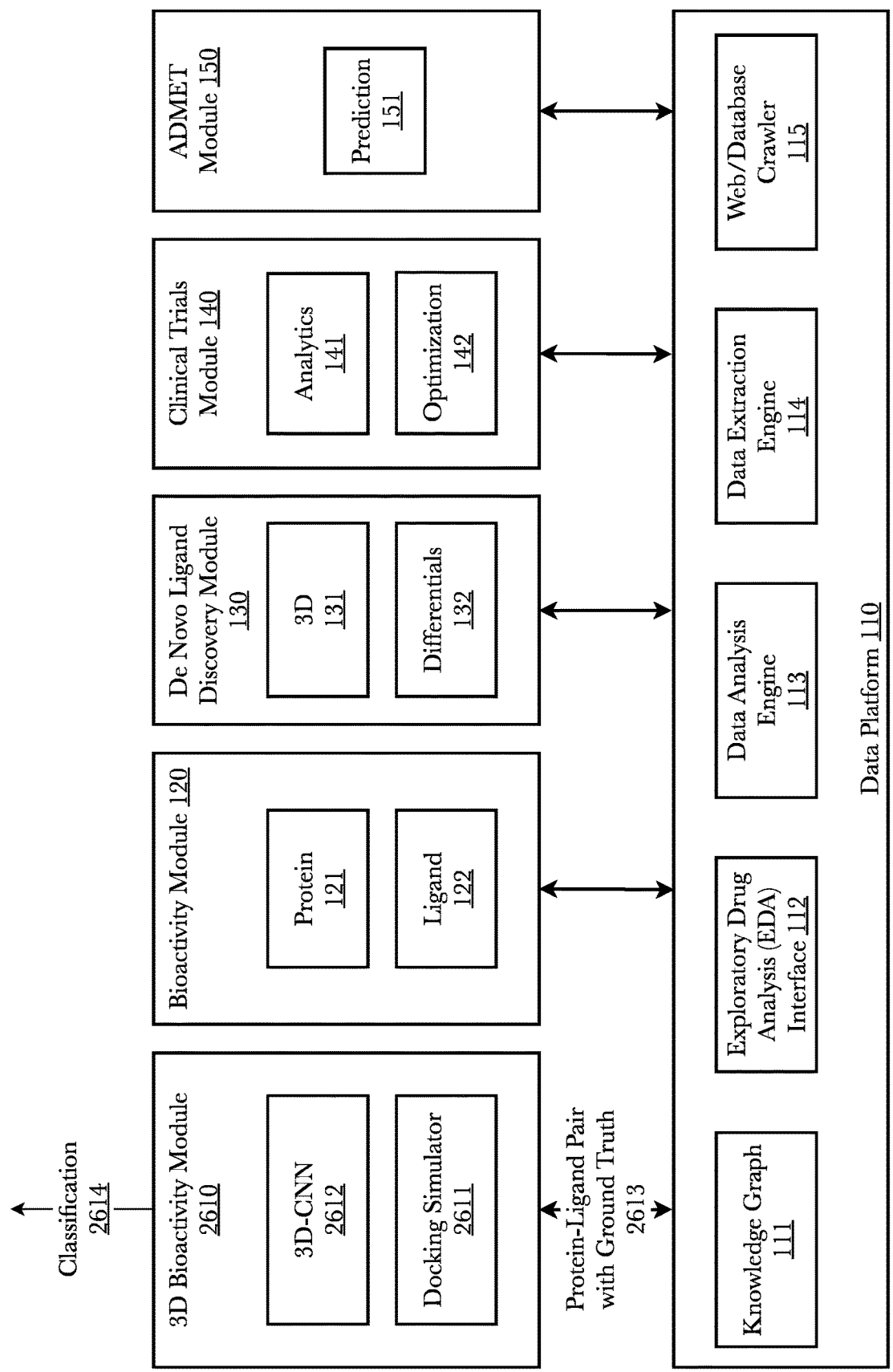
FIG. 26 is a block diagram of an exemplary system architecture for a 3D Bioactivity platform.

FIG. 26 is a block diagram of an exemplary system architecture for a 3D Bioactivity platform. According to one embodiment, a 3D bioactivity module 2610, comprising a docking simulator 2611 and a 3D-CNN 2612 may be incorporated into the system described in FIG. 1 containing elements 110-151. A data platform 110 scrapes empirical lab results in the form of protein-ligand pairs with a ground-truth state 2613 from public databases that is then used in a docking simulator 2611 to produce a data set for which to train a three-dimensional convolutional neural network (3D-CNN 2612) classifier, which as disclosed herein is a model that can classify a given input of a certain protein-ligand pair is active or inactive and whether or not the pose is correct 2614. A key feature of the 3D-CNN bioactivity module 2610 as disclosed herein, is the ability to produce visualizations of the interactions in the input that are vital to the active/inactive classifications in a more interpretable manner than a FASTA-based model currently used in the art. The output incorporates gradients relating to the binding affinity of specific atoms that a user may use to understand where the model was most attentive and would further provide an explanation why specific molecules are bioactive and why certain molecules are not and to identify the important residues of the binding site. Once the residues are identified, sequence-based similarities algorithms may identify similar motifs in other proteins from the same family or in completely novel proteins relating to that ligand interaction. Furthermore, the 3D-CNN model disclosed herein improves upon current art by penalizing the model for incorrect docking, thus leading to a three class classification 2614: active, inactive, and incorrect docking.

Figure 28:
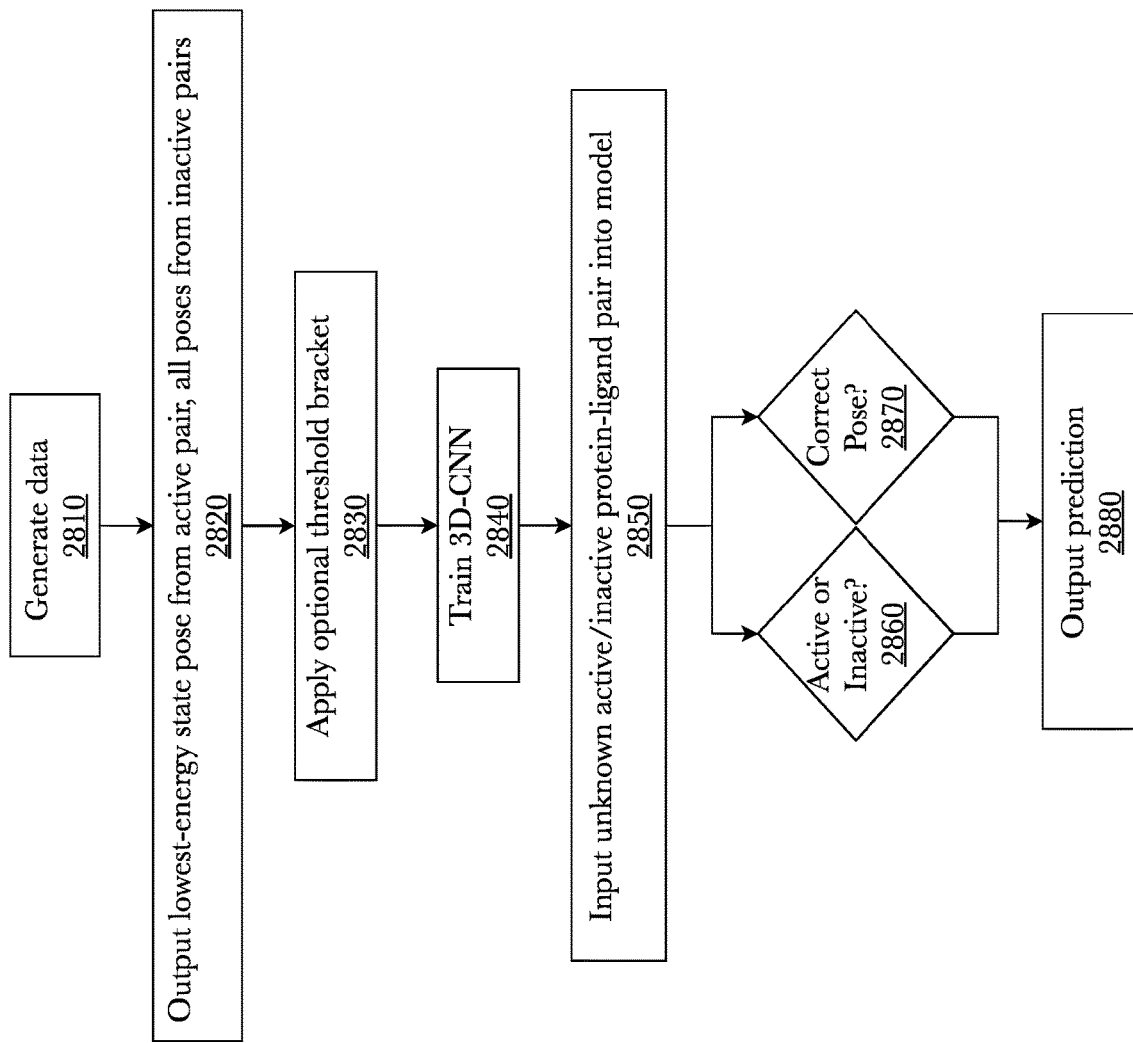
FIG. 28 is a flow diagram illustrating an exemplary method for classifying protein-ligand pairs using a 3D Bioactivity platform.

FIG. 28 is a flow diagram illustrating an exemplary method for classifying protein-ligand pairs using a 3D Bioactivity platform. Data is generated 2810 from lab-based empirical evidence which constitutes protein-ligand pairs and their ground-truth state. That data is sent to a docking simulation whereby energy states of the input poses are output along with a classification of active/inactive—from the lab data 2820. The training data presents a choice of a threshold bracket 2830. The threshold bracket is a trade-off between the average information contained in each datapoint, and the sheer quantity of data, assuming that datapoints with more extreme inactive/active $IC_{50}$ values are indeed more typical of the kind of interactions that determine whether or not a protein-ligand pair is active or inactive. In the case of the 3D-model, using the dataset with no threshold performs consistently better across most metrics. The channels used for the data set are hydrophobic, hydrogen-bond donor or acceptor, aromatic, positive or negative ionizable, metallic and total excluded volume. Regardless of the choice of threshold, the data is then used to train a 3D-CNN to know the classification of a molecule regarding activation and pose propriety 2840. The 3D bioactivity platform then receives an unknown molecule 2850 that is fed into the model to determine its classifications 2860/2870. The prediction is output 2880, and in some embodiments, may be used in backpropagation to further inform the model.

Figure 30A:
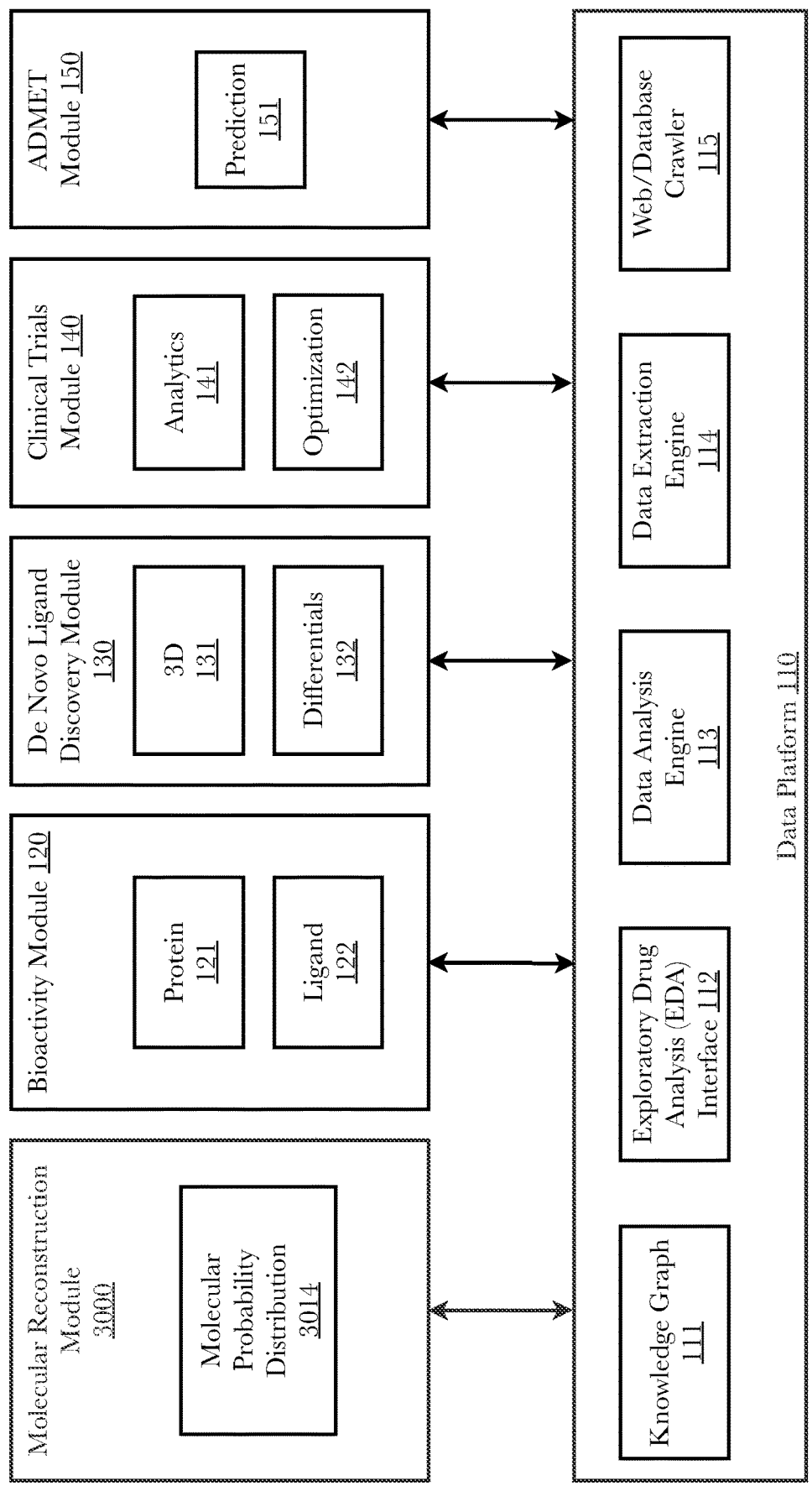
FIG. 30A is a block diagram illustrating an exemplary overall system architecture for a pharmaceutical research system with a molecular reconstruction module.

FIG. 30A is a block diagram illustrating an exemplary overall system architecture for a pharmaceutical research system with a molecule reconstruction module 3000. According to one embodiment, a molecular reconstruction module 3000 is added to a pharmaceutical research system. Molecular reconstruction module 3000 may replace other 3D encoders present in other embodiments or work with them in tandem. Molecular reconstruction module 3000 learns a mapping which may translate wave-like representations of a reconstructed molecule into a Gaussian-like representation for enhanced interpretation. In other words, molecular reconstruction module 3000 may reconstruct valid molecular representations from dense (probabilistic) voxels of the interpretable semi-Gaussian-like molecules.

Figure 30B:
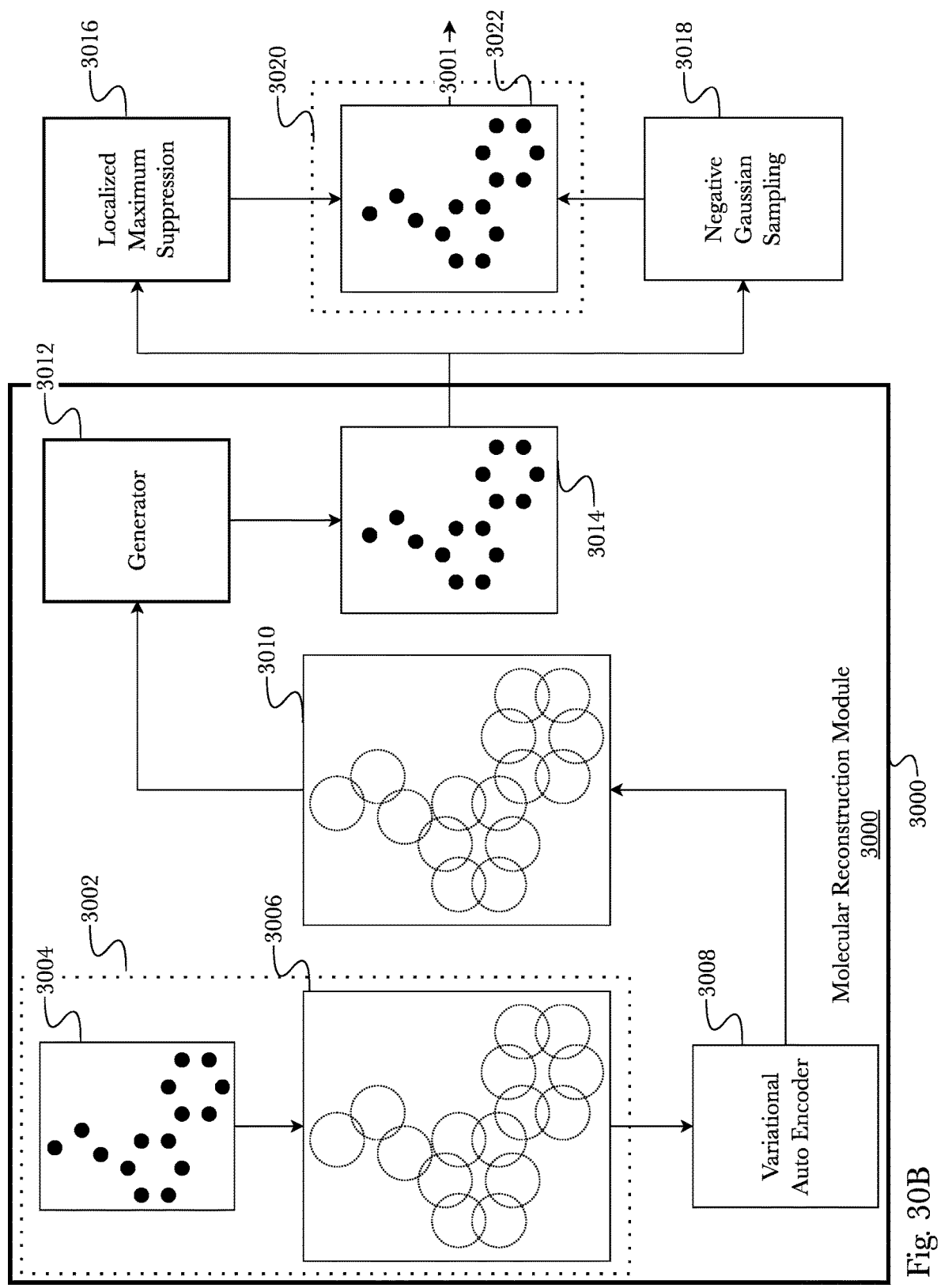
FIG. 30B is a block diagram illustrating an exemplary overall system architecture for a molecular reconstruction module.

Molecular reconstruction module 3000 constructs molecular probability distributions 3014 using the pipeline illustrated in FIG. 30B. Initially, molecular representations are constructed using molecular gridding 3002, which may take advantage of GPU accelerated libraries for deep learning, according to one aspect. Subsequently, the true molecular representation 3004 is used to construct a wave-transformed molecular representation 3006. The wave-transformed molecular representation 3006 is sent to a 3D Convolutional Variational Auto-Encoder 3008 that outputs a reconstructed equivalent 3010 of the wave-transformed molecular representation 3006. A generator 3012 (e.g., semi-inverse Weiner deconvolution) is used on the previous output 3010 to further produce another output 3014 comprising a reconstructed equivalent of the true representation of the molecule. This output 3014 is a probability distribution of the target molecule that provides significant information for use in density-to-molecule transformations and other applications within the biochemists and pharmaceutical industries. One example of the use of the probability distribution is the following density-to-molecule transformation steps comprising localized maximum suppression 3016 and negative Gaussian sampling 3018 which together produce one-hot encoded molecular grids which are then converted to one or more molecular graphs 3020 to produce molecular representations 3022—such as SMILES—which can be output 3001 and used to checked for validity.

Figure 31:
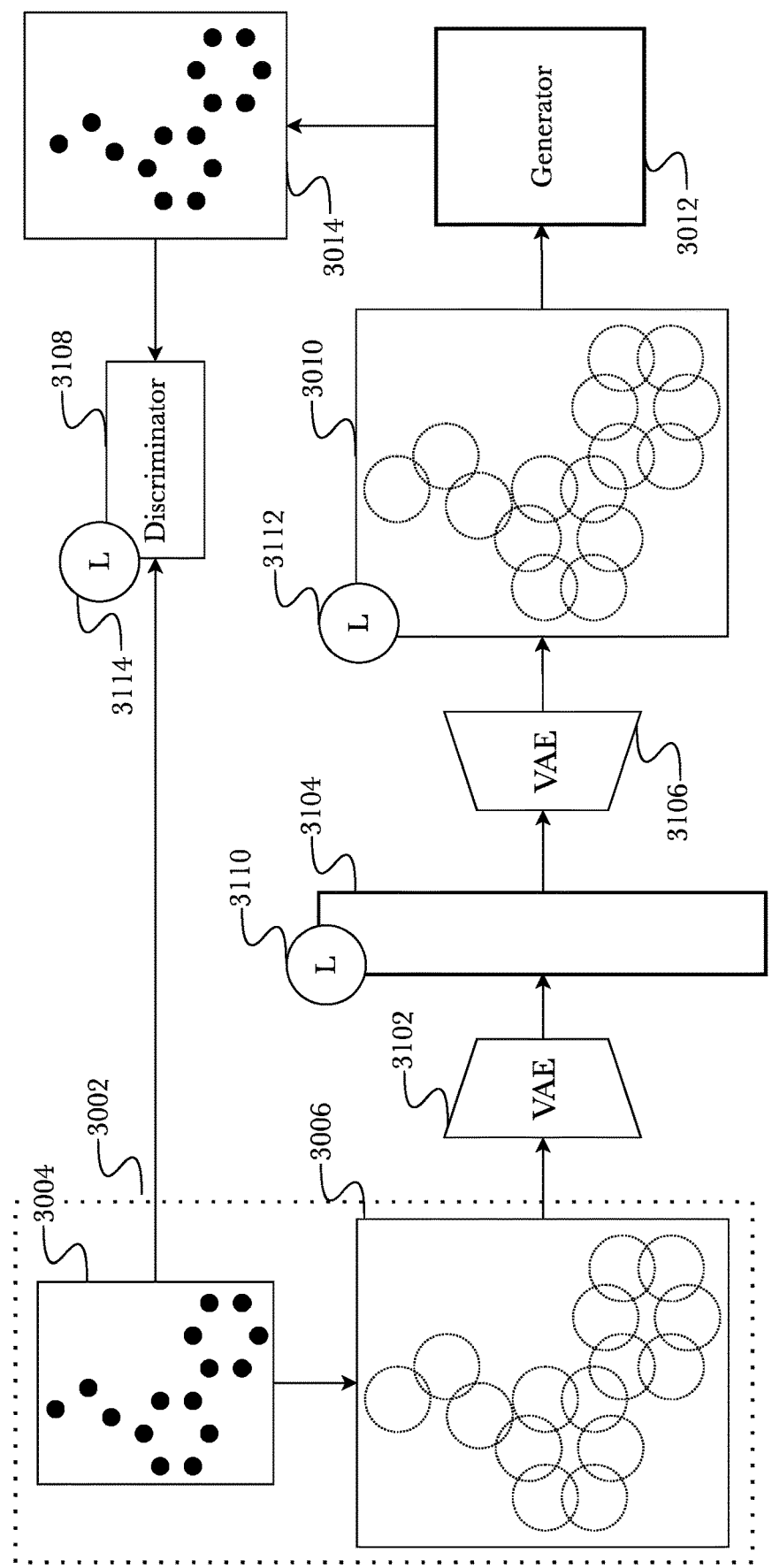
FIG. 31 is a block diagram illustrating an exemplary overall system architecture for hybrid adversarial training of the molecular reconstruction module.

In order to train such a generator 3012, an exemplary pipeline is provided as illustrated in FIG. 31. Given the goal of mapping into a "form" equivalent to that of the true molecular representation 3004, a discriminator 3108 is trained to identify if the reconstructed molecule 3014 comes from the training distribution (true molecule distribution 3004), or is generated by the generator 3012. This learns a mapping which can finetune the noise wavy reconstruction into an interpretable form. Pretraining the generator 3012 may be exploited by using batch accumulation to store the signal-to-noise ratio (SNR). Which is a way to empirically extract the noise distribution from a number of reconstructions (SNR is a function of the difference between 3006 and 3010). With this, the rather tedious GAN training process may be expeditiously performed. Moreover, it reduces the chance for perfect discriminator issues common during GAN training. The discriminator 3108 may also be pretrained via supervised maximum likelihood estimation. By detaching, the gradients from the outputs in the generator 3012, both the generator 3012 and discriminator 3108 may be pretrained. Exemplary code for the implementation of a pretrained generator 3012 is found in FIG. 32. Likewise, FIG. 33 is exemplars code for the implementation of a pretrained discriminator 3108.

The pipeline further comprises three losses 3110-3114. The goal of the overall system is to generate interpolatable and interpretable molecules represented as one-hot encodings in a 3D grid, where inputs are wave-like representations of molecules in a per-channel type. The losses are as follows: Kullback-Liebler divergence 3104 loss 3110, VAE 3102/3106 reconstruction loss, and adversarial loss 3114 which contributes to the VAE graph as well. However, it may be decided to detach gradients after backpropagating through the generator 3012 as it may be desirable to condition the generative model to learn the mapping of the generator 3012. In one embodiment, it is recommended that once the model has converged in this setup, the VAE reconstruction loss 3112 should be shut off and allow both the VAE 3102/3106 and generator 3012 to be finetuned with the adversarial loss 3114.

Figure 38:
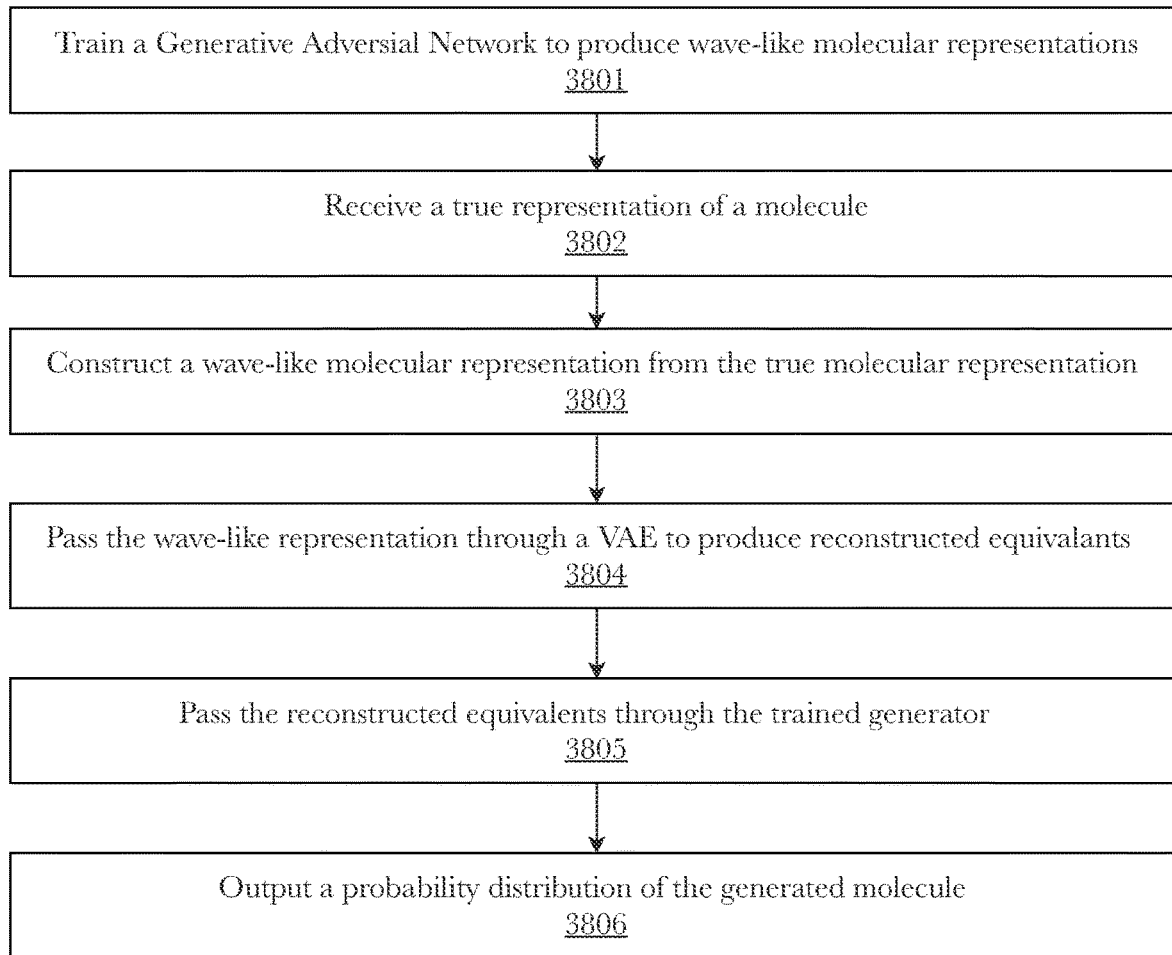
FIG. 38 is a flow diagram illustrating an exemplary method for reconstructing molecules from voxelated representations.

FIG. 38 is a flow diagram illustrating an exemplary method for reconstructing valid molecules from voxelated representations. In a first step 3801, a generator is trained in a generative adversarial network to produce wave-like molecular representations. In a second step 3802 one or more true representations of molecules are received and used to construct wave-like representations 3803. The wave-like representations comprise tensors of molecular data well suited for machine learning. In a fourth step 3804, the wave-like representations are passed through a variational autoencoder to produce soft Gaussian-like reconstructed equivalents of each respective molecule. In a fifth step 3805, the trained generator from the first step 3801 is used to generate valid and interpretable semi-gaussian molecules. In a sixth step 3806, probability distributions of the target molecule are generated and made available for further use. The molecular representations, i.e., probability distributions may be output for use with other components of a pharmaceutical research system or other external uses by the pharmaceutical and research industries.

Figure 39:
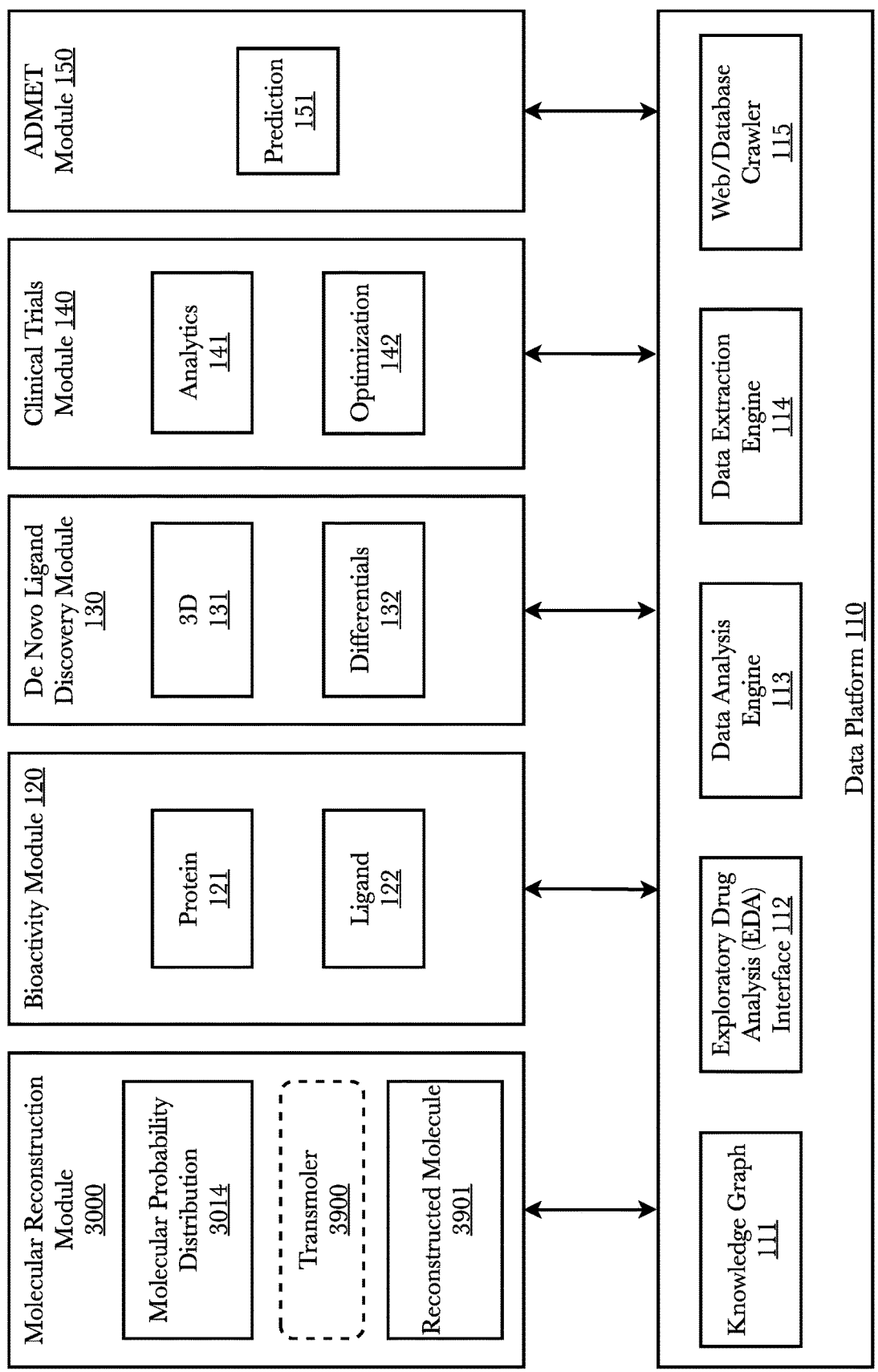
FIG. 39 is a block diagram illustrating an exemplary overall system architecture for a pharmaceutical research system with a molecular reconstruction module comprising a transmoler.

FIG. 39 is a block diagram illustrating an exemplary overall system architecture for a pharmaceutical research system with a molecular reconstruction module 3000 comprising a transmoler 3900. According to one embodiment, a transmoler 3900 is added to a molecular reconstruction module 3000 in a pharmaceutical research system which may comprise the components and aspects from FIG. 30A. Molecular reconstruction module 3000 may create a Gaussian-like representation of a molecule from input, which is then output as a molecular graph 3901, e.g., SMILES, using a transmoler 3900. Another aspect comprises generated density clouds from the De Novo 130 and/or Bioactivity modules 120 being sent directly to a transmoler 3900. This allows the pharmaceutical research system to hilly reconstruct valid molecular representations 3901 from dense (probabilistic) voxels of the interpretable semi-Gaussian-like molecules. Thus, this embodiment, and other contained herein, closes the generative 3D model, of which the various embodiments transform a distribution density to a chemical format. This is important for de nova discovery. However, generative molecules from voxelated representations aside, this embodiment may also generate molecules from protein structures. Instead of finding active molecules from a molecule and a bioactivity predictor, a binding site is scanned and from that scan the transmoler 3900 will predict certain substructures of the molecule in space that lead to high activity.

Figure 44:
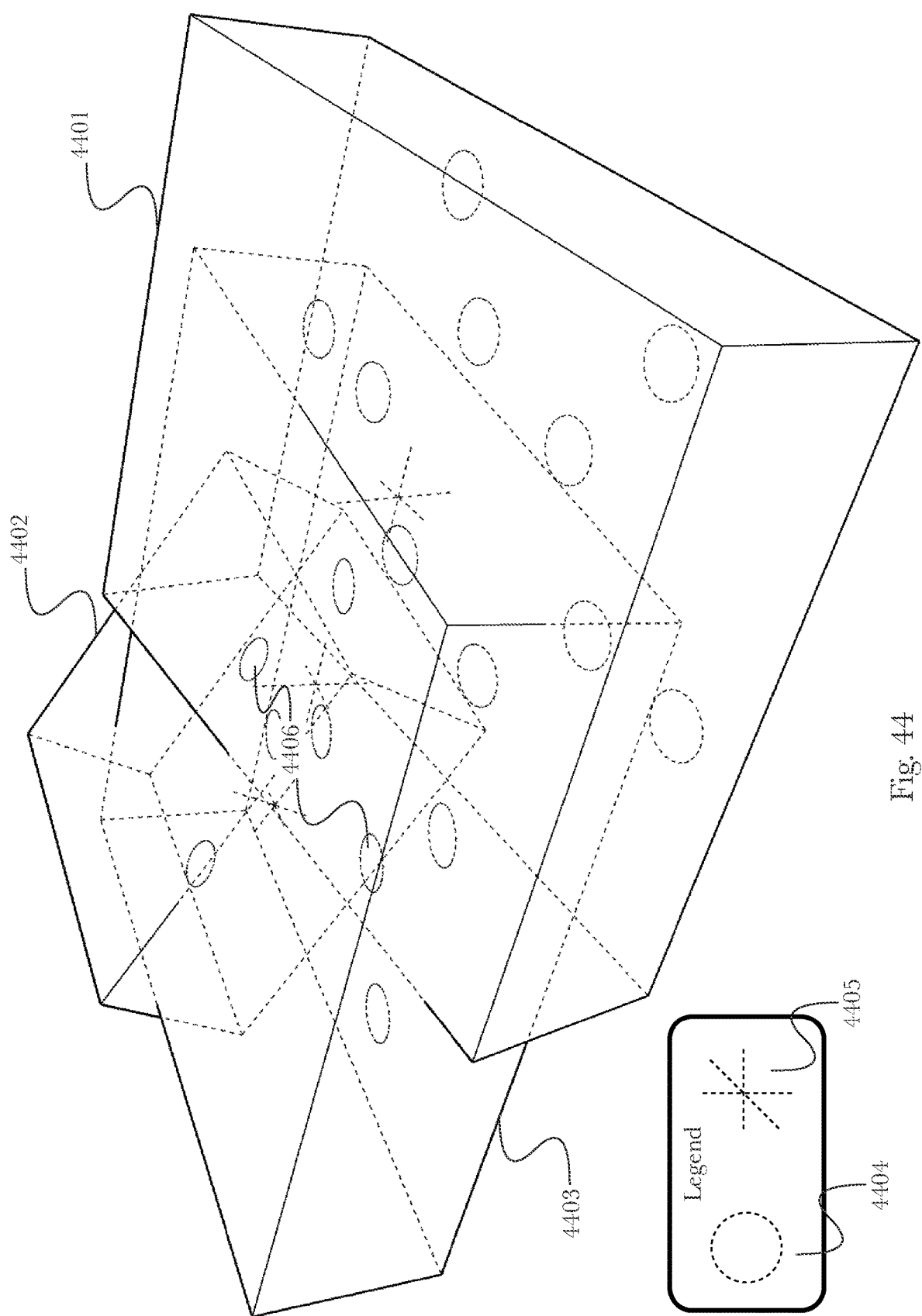
FIG. 44 is a diagram illustrating an exemplary molecule mapped in Euclidean space.

More specifically, transmoler 3900 represents substructures in Euclidean space and is programmed to make predictions as a set of encodings. Firstly, every molecule may be decomposed into its substructures via data preprocessing determining substructure properties. Every substructure in a molecule may then be represented in Euclidean space by drawing a box around it and computing the eigenvectors of its atomic distribution. The bounding box gives information about its position and occupancy in space, whilst the eigenvectors provide information about their orientation. Orientation is very important in chemistry as it provides insight as to how the molecule is structured in 3D space, allowing stereo and cis-trans isomers to be disambiguated further. Bounding boxes may be represented as oriented or unoriented. FIG. 44 illustrates an exemplary molecule mapped in Euclidean space. The exemplary molecule, its substructures, and other properties depicted here may not reflect chemically-valid real-world properties. This figure is presented for understanding and is reduced from a real-world complex model for simplicity sake. Looking now at the figure, three substructures are presented (where the atoms 4404 would form known substructures, such as a benzine ring) that are surrounded by bounding boxes 4401-4403. Each substructure having a substructure centroid with directional eigenvectors 4405, and a unique substructure signature embedding. Note, some atoms are shared 4406 between substructures. Not shown here, are all of the predicted substructure bounding boxes and centroids. Transmoler predicts many bounding boxes, however, according to this figure, a Hungarian-matching algorithm has already been applied which has selected the most likely predictions to be ground-truth and removed the rest. From the results of the Hungarian-matching algorithm, a tensor comprising a set of predictions (i.e., substructure centroids, substructure dimensions, substructure embedding, and substructure direction) is sent to a junction tree connector module for conversion to a standard chemical notation format. A detailed description of the preceding process and of a transmoler 3900 is provided in FIG. 40.

Figure 40:
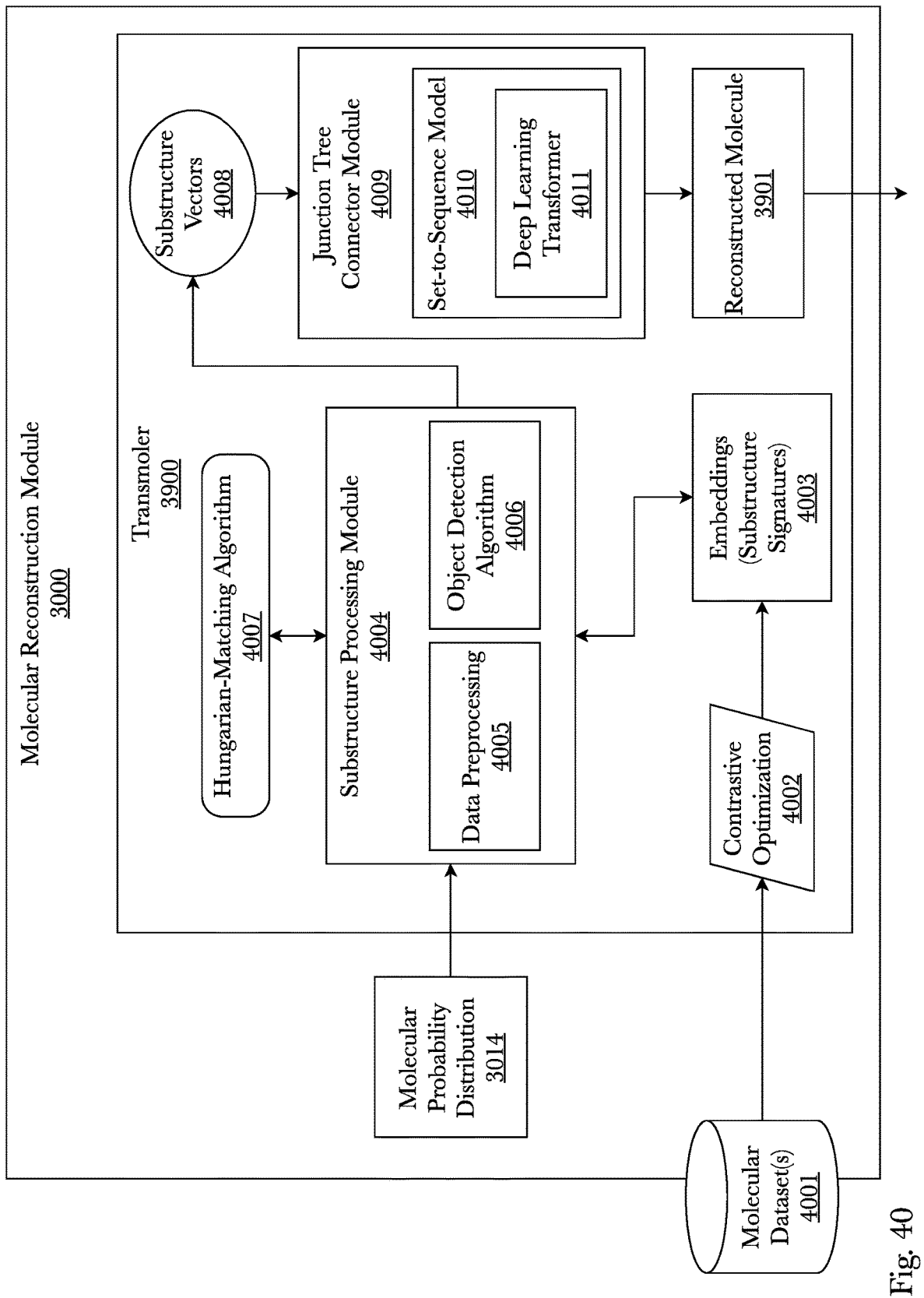
FIG. 40 is a block diagram illustrating an exemplary overall system architecture for a molecular reconstruction module comprising a transmoler.

FIG. 40 is a block diagram illustrating an exemplary overall system architecture for a molecular reconstruction module 3000 comprising a transmoler 3900. Transmoler 3900 receives an input of a gaussian representation of a molecule 3014, and may be tasked with the conversion of probability densities 3014 to molecular graph representations 3901. Given the redundancy in molecular chemistry, commonalities between scaffolds of a query molecule may be exploited to find which substructures constitute it. It is not enough to extract centroids sampled from the gaussian representations as this is, by definition, a subset of the gaussian representation, which may be inherently inferior. To succeed in finding substructures, two steps are disclosed: find volumes where it is desired to query a substructure, and classify the query substructure with the current vocabulary. One novel aspect of at least this embodiment is to treat the preceding two steps as an object detection task, although instead of training the object detection model on classification, the model is trained via template matching. This avoids the massive issue regarding class imbalance inherent in classification tasks. Not only would a classifier component struggle to learn highly sparse one-hot representations, but it would also struggle to generalize to all possible substructures. Therefore, the present embodiment uses template-based matching models to find a query structure inside a larger corpus.

According to the present embodiment, in order to determine a substructure (e.g., benzine ring) in a 3D gaussian representation, transmoler 3900 parses the molecule through one or more bounding cubes, and from the reference bounding space, transmoler 3900 may then parse through query scaffolds and determine the most adequate one based on a matching score. To achieve this, an object detection algorithm (e.g., DETR) may be used where the classification objective is changed into a regression objective. Since transmoler 3900 translates classification into template matching, a new objective based on the following observations may be created: a) similar scaffolds are to have a low representational shift, and b) dissimilar scaffolds are to have a high representational shift.

Figure 41:
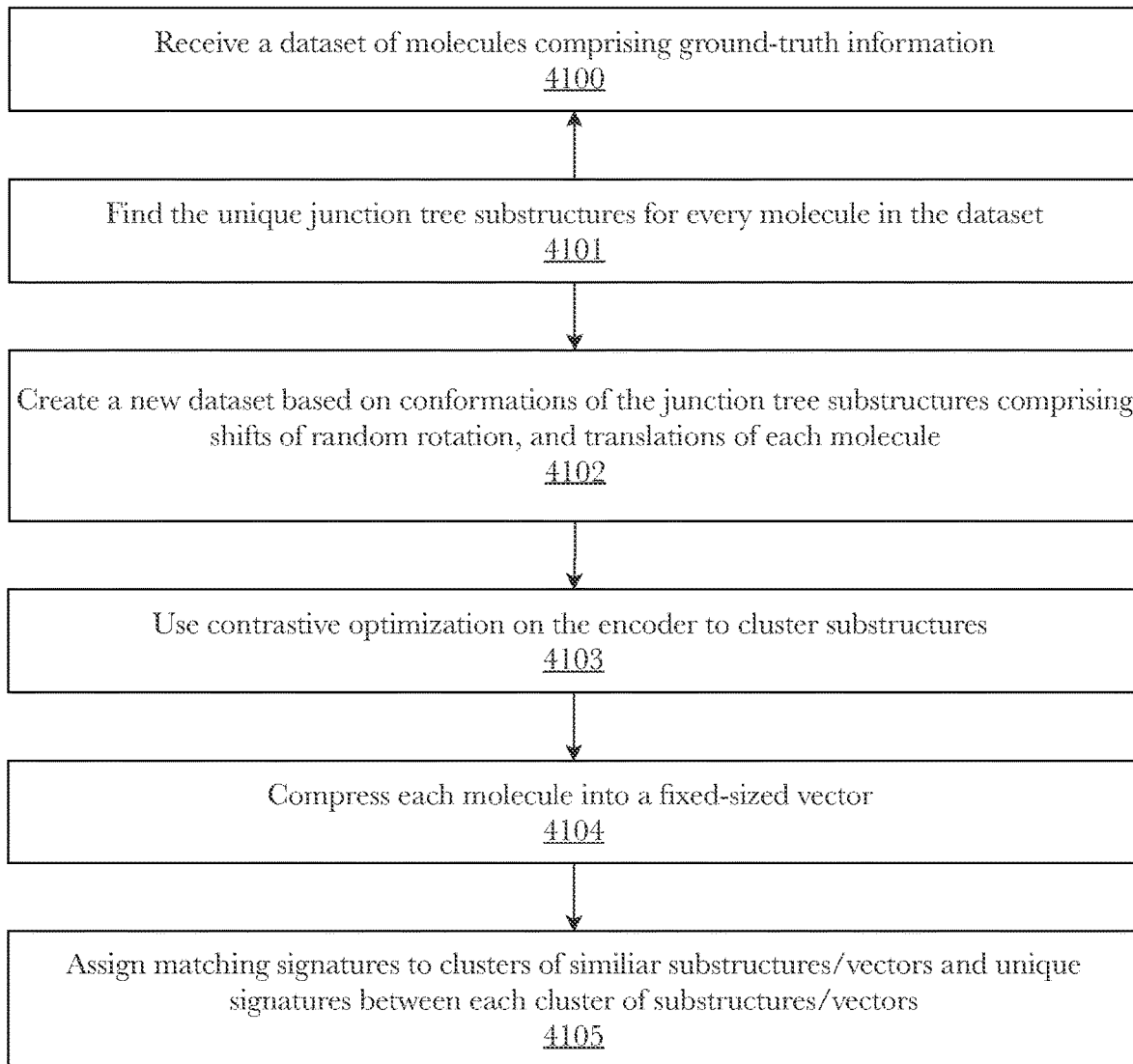
FIG. 41 is a flow diagram illustrating an exemplary method for creating embeddings used for comparative analysis by a substructure processing module, according to one embodiment.
Figure 42:
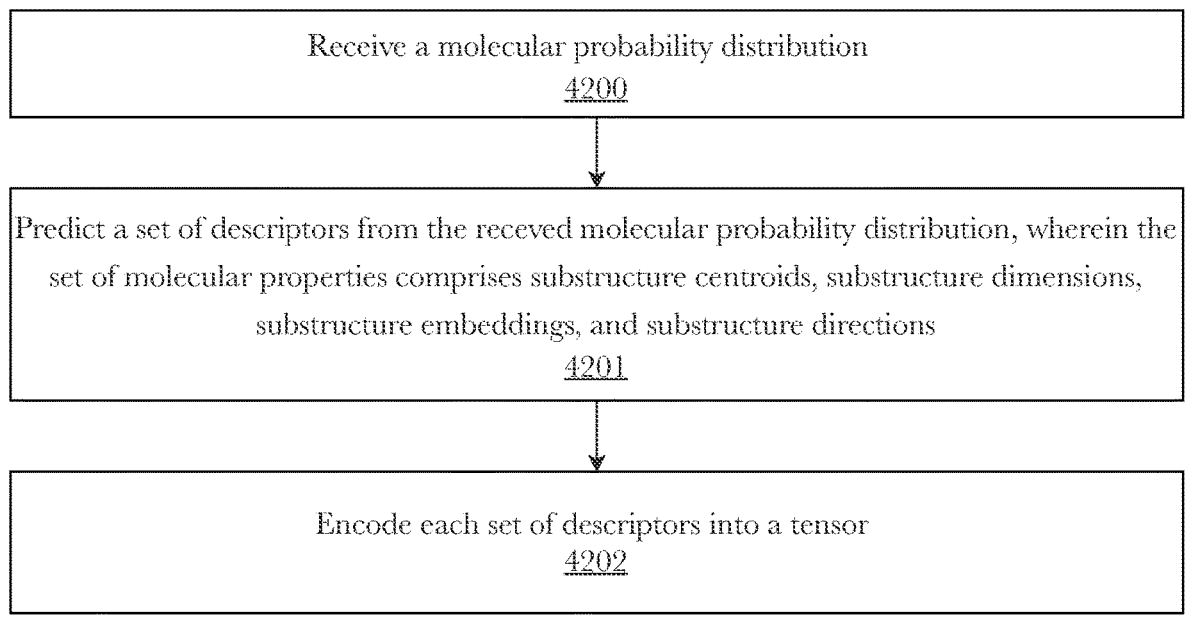
FIG. 42 is a flow diagram illustrating an exemplary method for using a substructure processing module to predict and encode a set of molecular descriptors, according to one embodiment.

Transmoler 3900 may be conceptualized in three parts: a) a sub-system for creating substructure signatures 4001-4003, b) a sub system for substructure identification and prediction 4004-4008, and c) a sub-system for molecular reconstruction 4009-4011, according to one embodiment. Where FIG. 40 pertains to the systems, FIG. 41-FIG. 43 refer to the methods of each sub-system, respectively. Regarding creating substructure signatures (FIG. 40 and FIG. 41), ground-truth vectorized descriptors of substructures—which are translationally and rotationally invariant—are devised by training embeddings (i.e., substructure signatures) using the following methodology:

A) Train an embedding using an encoder (as overfilled as possible) and contrastive, optimization 4002 with conformer augmentation techniques (rotation, translation, conformation invariance).

B) Use steerable CNNs or some form graph/point-based model (although CNNs are preferred since data formats may be kept monotonic for debugging purposes) 4101.

C) Penalize representational shift from A and A*, where A* is equivalent to A after some random rotation (e.g., [−pi, pi]), and slight translation only slight since these may be centered) and A* may be another conformation of A.

D) Penalize latent space distribution to maintain the embedding in the same hypersphere 4101.

Because the transmoler 3900 uses object regression, it is favored to form structural descriptors which allow template matching to be internalized by an object detector system. To that end, embeddings of junction Tree (JT) nodes using contrastive loss functions 4003/4103 may be constructed 4101/4102 by jointly: minimizing the distance between conformers of identical substructure, and maximizing the distance between embeddings of different substructures. After finding the representative substructures 4102, a new dataset is created based on conformations of these substructures as well as random translations and rotations of these. A 3D CNN model is used to produce substructure embeddings (JT fingerprints). An encoder is then optimized via contrastive methods 4103. Using contrastive optimization 4003/4103, all substructure vectors are trained to be dissimilar—this repulsive force will distance similar (chemical proximity) molecules less than non-similar molecules, consequently producing clusters of similar substructures. Embeddings are then built by compressing the 3D molecular structure (CNNs) into a fixed-sized vector 4104. Clusters of similar substructures/vectors may be assigned similar signatures, while the clusters themselves will not have similar signatures compared to other clusters 4105. The similarity between signatures is a distinction as to the similarity of the substructures, thus achieving a 3D-aware continuous distribution of chemically similar environments.

In summary, take a dataset of millions of molecules 4001/4100, separate each molecule independently, identify the shared substructures 4101, create a signature for each unique substructure, and train similar substructures to have similar signatures 4003. Fundamentally, the embedding module 4003 automatically orders a possible vector space of the substructures that are provided and outputs an embedding space that makes molecular sense. With the embedding space completed, details of the second part of the transmoler (i.e., the substructure identification and prediction (FIG. 40 and FIG. 42)) follows below.

Akin to typical residual CNN pretrained models used for transfer learning, heavy duty voxel featurizers may also be desired for this application. The parameters trained on ResVAE's 3D wave-based encoder-decoder as described in the co-pending parent application, i.e., FIG. 30A-FIG. 38, may be exploited to this end and fine-tuned to reconstruct wavy molecular representations from gaussian inputs instead. Hence, the backbone of the transmoler 3900 consists of a pre-trained gaussian autoencoder.

Figure 45:
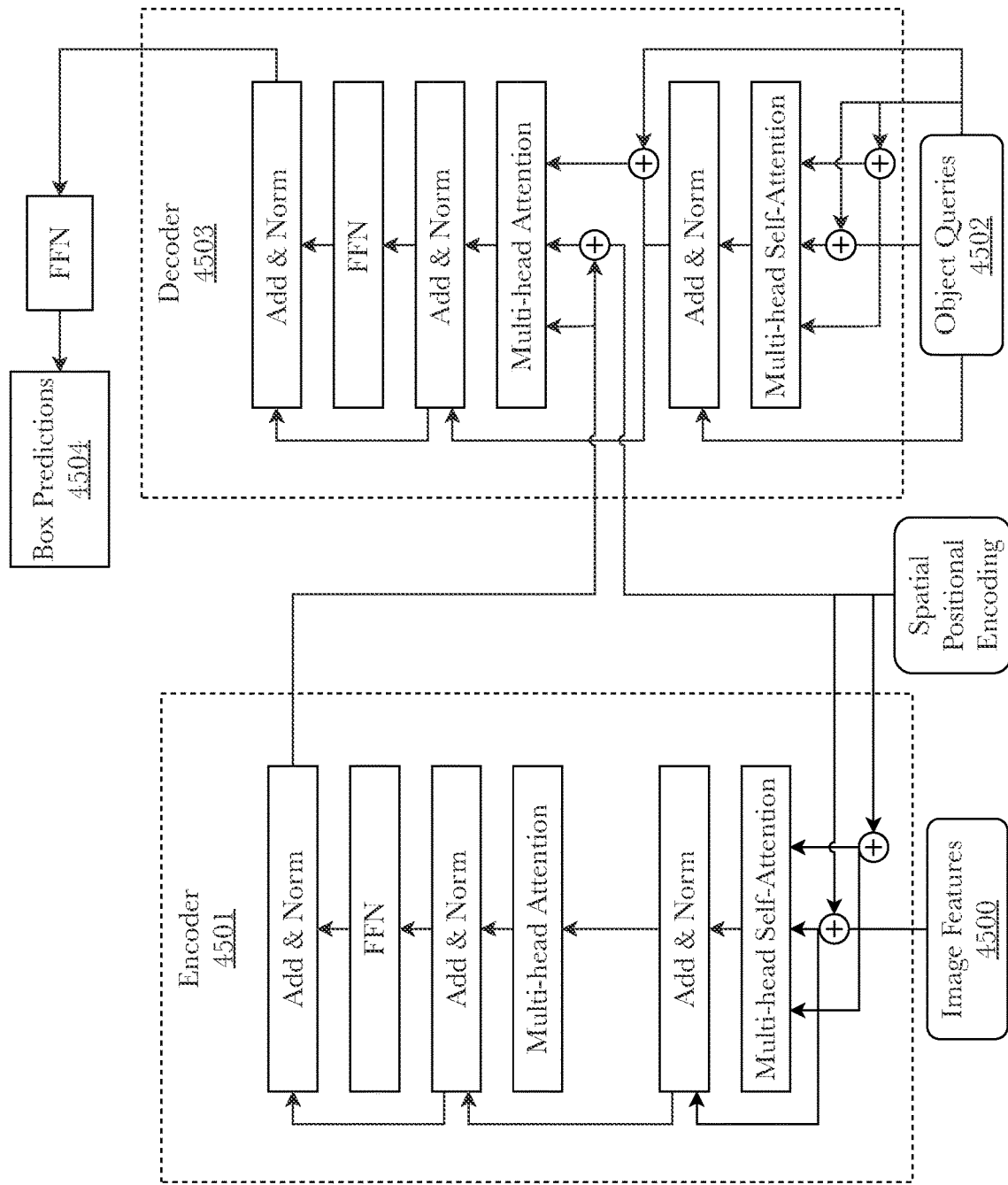
FIG. 45 is a block diagram illustrating a base model architecture for a transmoler.

Once the backbone has been pre-trained and the embeddings space 4003 for each substructure have been optimized via contrastive optimization 4002, the transmoler 3900 may now be trained. Generally, the training process of the transmoler 3900 works as illustrated in FIG. 45. The base system is an object detector and Gaussian reconstructions are passed in through the backbone and concatenate the feature representations of $n^{th}$ hidden layer Fn (where Fn is a vector (sentence equivalent) of dimensions 512) into a sentence 4500. Positional encoding 4505 based on the 3D occupancy of each of the variables in the feature representation Fn 4500 is also added. This positional encoding 4505 serves as a reference signal which aims to enforce a spatial ordering of the concatenated variables in Fn 4500. The representation is then encoded using a transformer-based encoder 4501 and uses the hidden representation to condition transmoler's decoding 4503 stage. During decoding 4503, object queries 4502 (learned query vectors) are used to output different box predictions 4504. Note that these object queries 4504 are learned during training and are then fixed at test time. For each Box Prediction 4504 the following is approximated: eigenvectors, substructure centroids, embedding predictions, box dimensions, and class probability (true box or fake box).

It is not a trivial endeavor to assign which bounding boxes predicted by an object detection algorithm 4006 correspond to ground truth boxes. This is because each molecule may have a different number of substructures. In contrast to the molecular probability distribution 3014, which is always the same dimensions, albeit different information. Thus, a Hungarian matching algorithm 4007 is used to determine the best possible scenario, i.e., the best match to ground truth. The Hungarian Matching algorithm determines the bipartite matching between ground truth boxes and predicted boxes which minimizes the total loss. This algorithm performs a search over all possible permutations. Learning is massively improved by performing the best possible match between ground truth boxes and predicted boxes since this allows a much smoother gradient signal to be backpropagated. Experimental evidence has proven the implementation of this algorithm to be effective.

With the transmoler 3900 training complete 4200 and an available corpus of ground-truth substructure embeddings 4003, a substructure processing module 4004 during actual use ingests 4201 molecular probability distributions 3014, predicts the proper substructures 4201, and outputs 4202 a tensor (a set of concatenated vectors) 4008 comprising a set of encodings. The tensor 4008—which fully describes the molecule and is more compressed than a Gaussian distribution 3014—comprises substructure centroids, substructure dimensions, substructure embeddings (mappable to a known molecular graph), and substructure directions (eigenvectors), all of which may be visually represented with modelling tools (see FIG. 44), albeit the substructure embedding are typically latent 4202. Once the right substructures are identified (space and orientation) and classified (embedding lookup), the substructures roar be connected at the graph level. Details on the molecular reconstruction using graph connectivity theory follow below.

Figure 43:
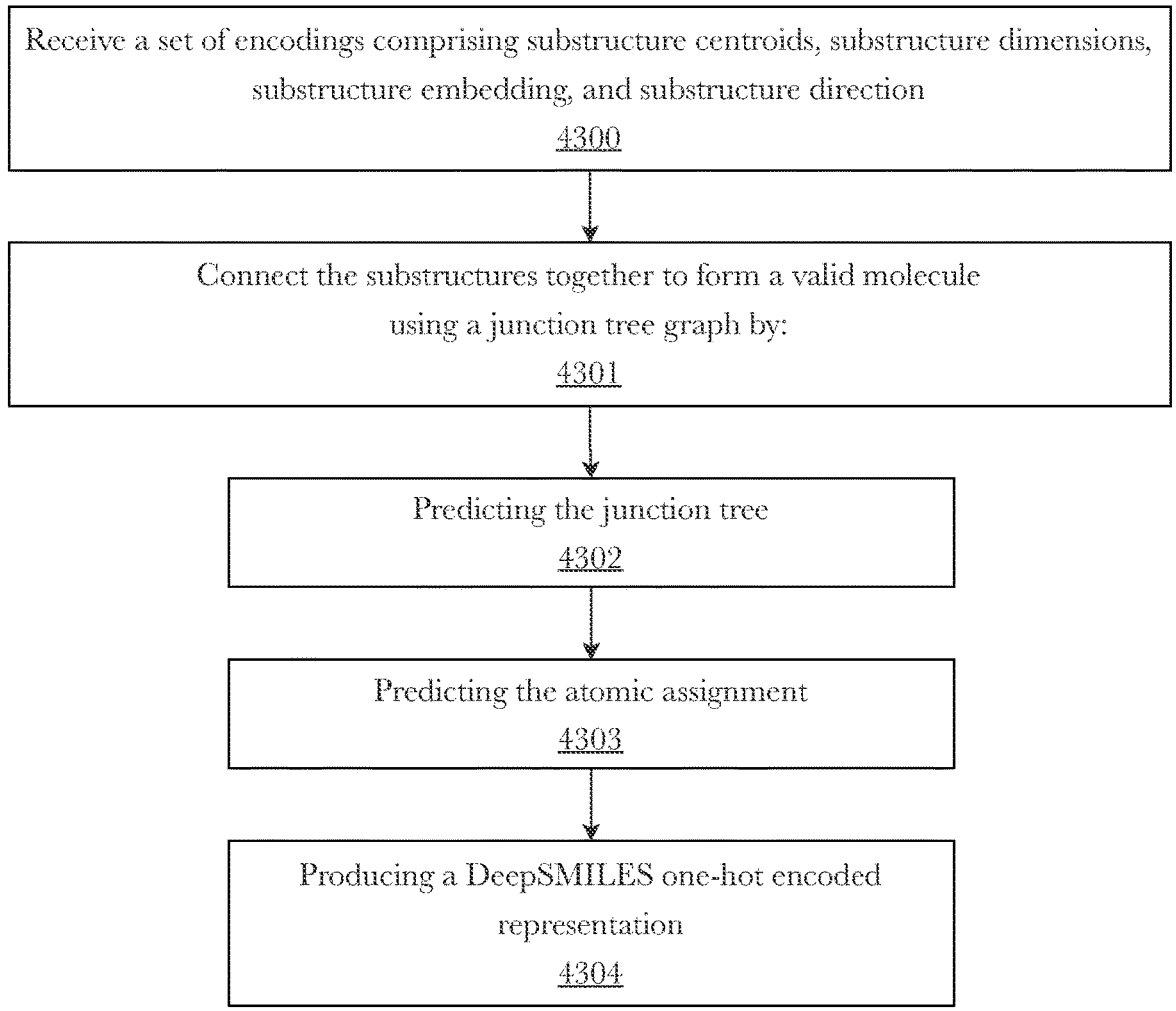
FIG. 43 is a flow diagram illustrating an exemplary method for converting a tensor of predictions into a molecular string representation, according to one embodiment.

Molecular reconstruction may be accomplished via junction tree (JT) technologies according to one embodiment (FIG. 40 and FIG. 43). Molecular reconstruction begins with the set of encodings which contain information about substructure centroids, substructure dimensions, substructure embedding (mappable to SMILES), and substructure direction (eigenvectors), the substructure vector 4008/4300. Because the vector 4008 identifies the right substructures (space and orientation) and classifications (embedding lookup), the next step is to connect these substructures at the graph level 4301. Additionally, the 3D conformation of the input molecule can also be recovered in an intermediate stage, as the gaussian backbone's encoded feature map. The latter may be useful to help discern which atoms overlap from within adjacent substructures.

To graphically determine how substructures connect in 3D space, it is evident that substructures with overlapping bounding boxes indicate that these are adjacent (existing edge), and those atoms which overlap within these bounding boxes correspond to the linking node (referring to FIG. 44). However, there are many corner cases, and it is not obvious to translate this knowledge into graphical form. Thus, two steps are disclosed in the present embodiment to overcome this obstacle. The first being to predict the junction tree 4302 and the second being to predict the atomic assignment 4303.

Predicting the junction tree 4302 requires that all JT nodes be connected to its adjacent neighbors. This can be accomplished by one of the two following methods: 1) Node-based (classifying each pair wise node as "connected" or not to each other.) or 2) Edge-based (creating edges (adjacency matrix prediction). To achieve the second path, first create a maximal graph for all pairwise JT Node connections and predict which edges are actually correct. Force the model to only consider the set of neighbors which lie under a certain distance threshold, and can create either a sequential model which prunes edges until decides not to do so, or rather a deterministic model which predicts the affinity matrix (symmetric).

According to one embodiment, an edge-based approach is used, where message-passing neural-networks may be used over transmoler's 3900 hidden representations (the gaussian backbone's encoded feature map and the substructure vector 4008). Subsequently perform a Delaunay triangulation or analogous method (e.g., relative neighborhood graph) to reduce the node population. However, a complication exists where it is uncertain which node is which, thus a solution is required to be able to train JTPruning the output 4008. It is important to realize that the true JT is unique to the number of predicted nodes and their embeddings. Thus, the novel solution is to create an assigning function which looks at the JTNodes and assigns each node to the output 4008 based on a Hungarian matching algorithm 4007. Assign the most promising nodes to the nodes in the JT graph and during training, the edges for the isolated node should be empty. Note, that this may help discard redundant node predictions during test-time, thus it is recommended to use a relatively low classification threshold, and then discard using JTPrune. Furthermore, given atom-based dependencies, a hierarchical graph convolution system is preferred where the top-level nodes contain JTNode features, and bottom-level nodes contain atom-wise & edge-wise features sampled from the embedding.

This embodiment may also generate (like data by adding random nodes in different places, and JTPrune will detect these. This pray be incrementally implemented via curriculum learning and the following guidelines: train on ground truth; start adding random clones of nodes in different places; randomly add noise to the embeddings so that they are slightly different; and finally, train with the substructure vector 4008, using Hungarian matching assignment.

Predicting the atomic assignment 4303 once the junction tree is known comprises predicting how to connect, the nodes in the atom level. This is not trivial. However, disclosed herein are two methods to perform the predictions:

A) Predict the atomic assignment, where it may be determined which atoms from neighboring nodes are the same (note, by definition, for every neighboring JTNode there must be at least 1 overlapping atom). Henceforth referred to as AtomBind.

B) Build the graph sequentially from graph permutations and scoring functions. Henceforth referred to as JTDecode.

According to one embodiment using Atombind, the atoms are directly predicted from neighboring JT nodes which overlap. In a first step, the graphical representation of each embedding (minimal cosine similarity) is extracted. In a second step, a hierarchical GNN is created and performs autoregressive message passing along all high-level nodes. In a third step, permutate each possible leaf-based connectivity by finding all unique graphical assignments, and predicting the atom-level (pairwise node) classification of intersection. However, there may be complications which arise from symmetries and redundancies. Rotationally symmetric substructures may connect in many different forms. Hence, all the unique connections must be analyzed. According to one embodiment, a solution to the complications noted above comprises predicting the connection type. A classification for each type of connection is created and then classify for each JTNode type, via hierarchical message passing, the type of connection for each substructure.

According to one embodiment using JTDecode, the graphical connection is grown sequentially by permuting through all possible neighboring permutations. A proxy may be used to train to maximize the probability of predicting the right JT. A scorer may be built which learns to predict if an autoregressive encoding of the "current graph" being built is indeed part of the input latent representation.

Alternatively, another embodiment may comprise all the intermediate steps (predict the junction tree 4302 and predict the atomic assignment 4303) implicitly, i.e., finding nodes adjacent to one another; discard nodes which are inherently wrong (overpopulated scenario); predict missing molecular sequences; predicting connectivity from node to node; and stereoisomer and cis-trans isomer compatibility. Employ an attention-based set-to-sequence architecture 4010 such as the performer used to parse an un-sequenced and unconnected set of predicted junction tree nodes floating in space, where the features of each node are represented by the vector output 4008. A node level mechanism may then perform attention on these to predict the molecule DeepSMILES one-hot encoded representations 4304. Beam search and re-conformerization can also be performed to improve the models performance. In particular, re-conformarization involves reconstructing a molecule using our generative 3D restricted variational autoencoder and saving the gaussian representation (Xr'). Using Xr' to predict the set of box attributes (i.e., prediction boxes (Pb) attributes) using the substructure processing module 4004. Using Pb to generate various DeepSMILES using beam search (standard deep learning sequence prediction procedure). Then use re-conformerization of the predicted molecules to determine which of these better match Xr' via a registration. Since set sequence models suffer from over generation, this process can be very useful, ensuring or motivating the decoded molecule to actually represent its gaussian representation Xr'. Irrespective of the various approaches previously laid forth for molecular reconstruction, the transmoler 3900 output may be a SMILES representation 4304 given an input of a gaussian distribution representative 3014 of a molecule.

Detailed Description of Exemplary Aspects

Figure 10:
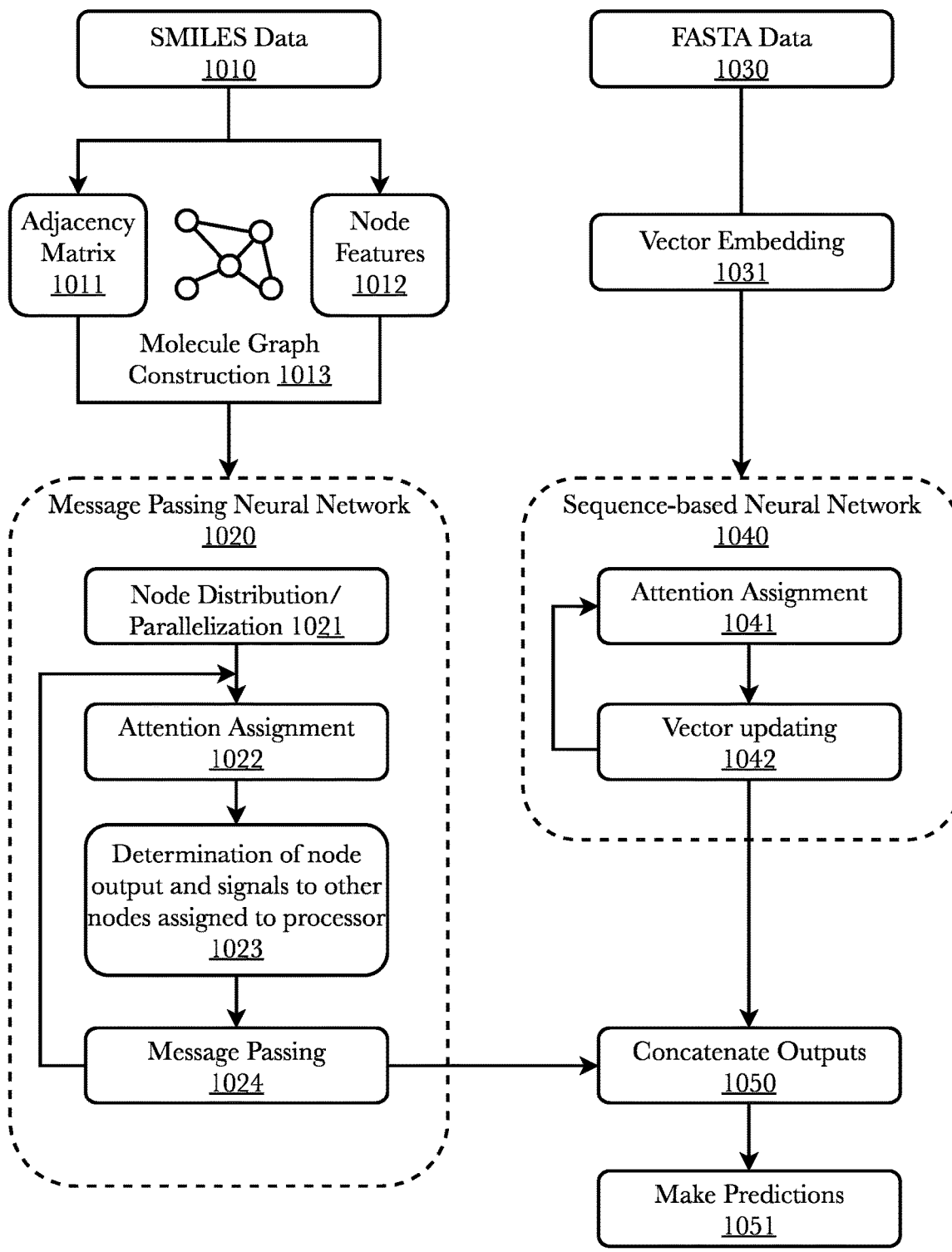
FIG. 10 is a diagram illustrating an exemplary architecture for prediction of molecule bioactivity using concatenation of outputs from a graph-based neural network which analyzes molecule structure and a sequence-based neural network which analyzes protein structure.

FIG. 10 is a diagram illustrating an exemplary architecture for prediction of molecule bioactivity using concatenation of outputs from a graph-based neural network which analyzes molecules and their known or suspected bioactivities with proteins and a sequence-based neural network which analyzes protein segments and their known or suspected bioactivities with molecules. In this architecture, in a first neural network processing stream, SMILES data 1010 for a plurality of molecules is transformed at a molecule graph construction stage 1013 into a graph-representation wherein each molecule is represented as a graph comprising nodes and edges, wherein each node represents an atom, and each edge represents a connection between atoms of the molecule. Each node represents the atom as node features comprising an atom type and a number of bonds available for that atom. The node features are represented as a node features matrix 1012. The molecule, then is represented as nodes (atoms) connected by edges (bonds), and is specified as an adjacency matrix 1011 showing which nodes (atoms) are connected to which other nodes (atoms).

At the training stage, the adjacency matrices 1011 and node features matrices 1012 for many molecules are input into the MPNN 1020 along with vector representations of known or suspected bioactivity interactions of each molecule certain proteins. Based on the training data, the MPNN 1020 learns the characteristics of molecules and proteins that allow interactions and what the bioactivity associated with those interactions is. At the analysis stage, a target molecule is input into the MPNN 1020, and the output of the MPNN 1020 is a vector representation of that molecule's likely interactions with proteins and the likely bioactivity of those interactions.

Once the molecule graph construction 1013 is completed, the node features matrices 1012 and adjacency matrices 1011 are passed to a message passing neural network (MPNN) 1020, wherein the processing is parallelized by distributing groups 1021 nodes of the graph amongst a plurality of processors (or threads) for processing. Each processor (or thread) performs attention assignment 1022 on each node, increasing or decreasing the strength of its relationships with other nodes, and outputs of the node and signals to other neighboring nodes 1023 (i.e., nodes connected by edges) based on those attention assignments are determined. Messages are passed 1024 between neighboring nodes based on the outputs and signals, and each node is updated with the information passed to it. Messages can be passed between processors and/or threads as necessary to update all nodes. In some embodiments, this message passing (also called aggregation) process is accomplished by performing matrix multiplication of the array of node states by the adjacency matrix to sum the value of all neighbors or divide each column in the matrix by the sum of that column to get the mean of neighboring node states. This process may be repeated an arbitrary number of times. Once processing by the MPNN is complete, its results are sent for concatenation 1050 with the results from a second neural network, in this case a long short term memory neural network 1040 which analyzes protein structure.

In a second processing stream, FASTA data 1080 is converted to high-dimensional vectors 1031 representing the amino acid structure of proteins. The vectors are processed by a long short term memory (LSTM) neural network 1040 which performs one or more iterations of attention assignment 1041 and vector updating 1042. The attention assignment 1041 of the LSTM 1040 operates in the same way as that of the MPNN 1020, although the coding implementation will be different. At the vector updating stage 1042, the vectors comprising each cell of the LSTM 1040 are updated based on the attention assignment 1041. This process may be repeated an arbitrary number of times. Once processing by the LSTM 1040 is complete, its results are sent for concatenation 1050 with the results from the first processing stream, in this case the MPNN 1020.

Concatenation of the outputs 1050 from two different types of neural networks (here an MPNN 1020 and an LSTM 1040) determines which molecule structures and protein structures are compatible, allowing for prediction of bioactivity 1051 based on known or suspected similarities with other molecules and proteins.

Figure 11A:
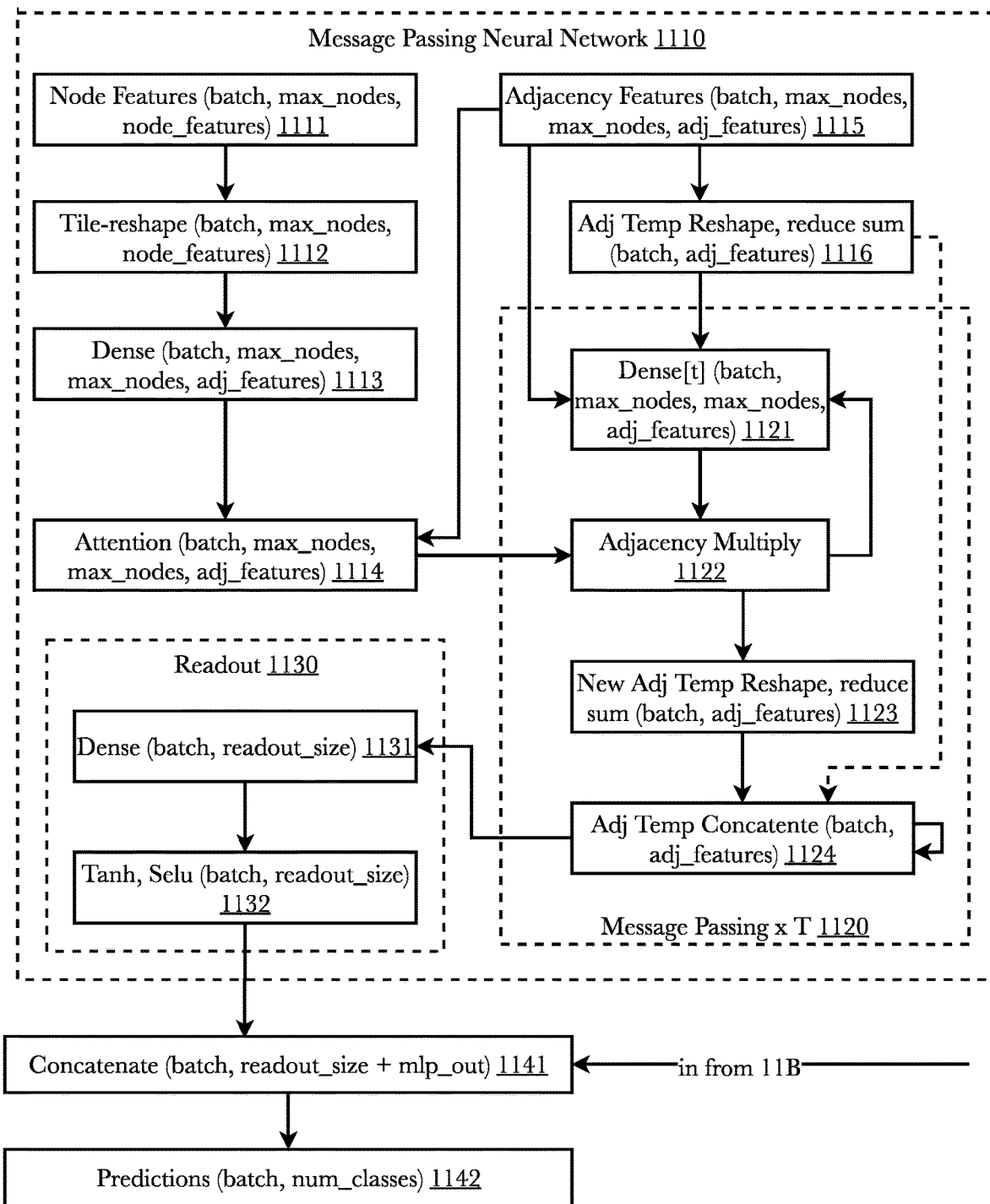
FIGS. 11A and 11B illustrates an exemplary implementation of an architecture for prediction of molecule bioactivity using concatenation of outputs from a graph-based neural network which analyzes molecule structure and a sequence-based neural network which analyzes protein structure.
Figure 11B:
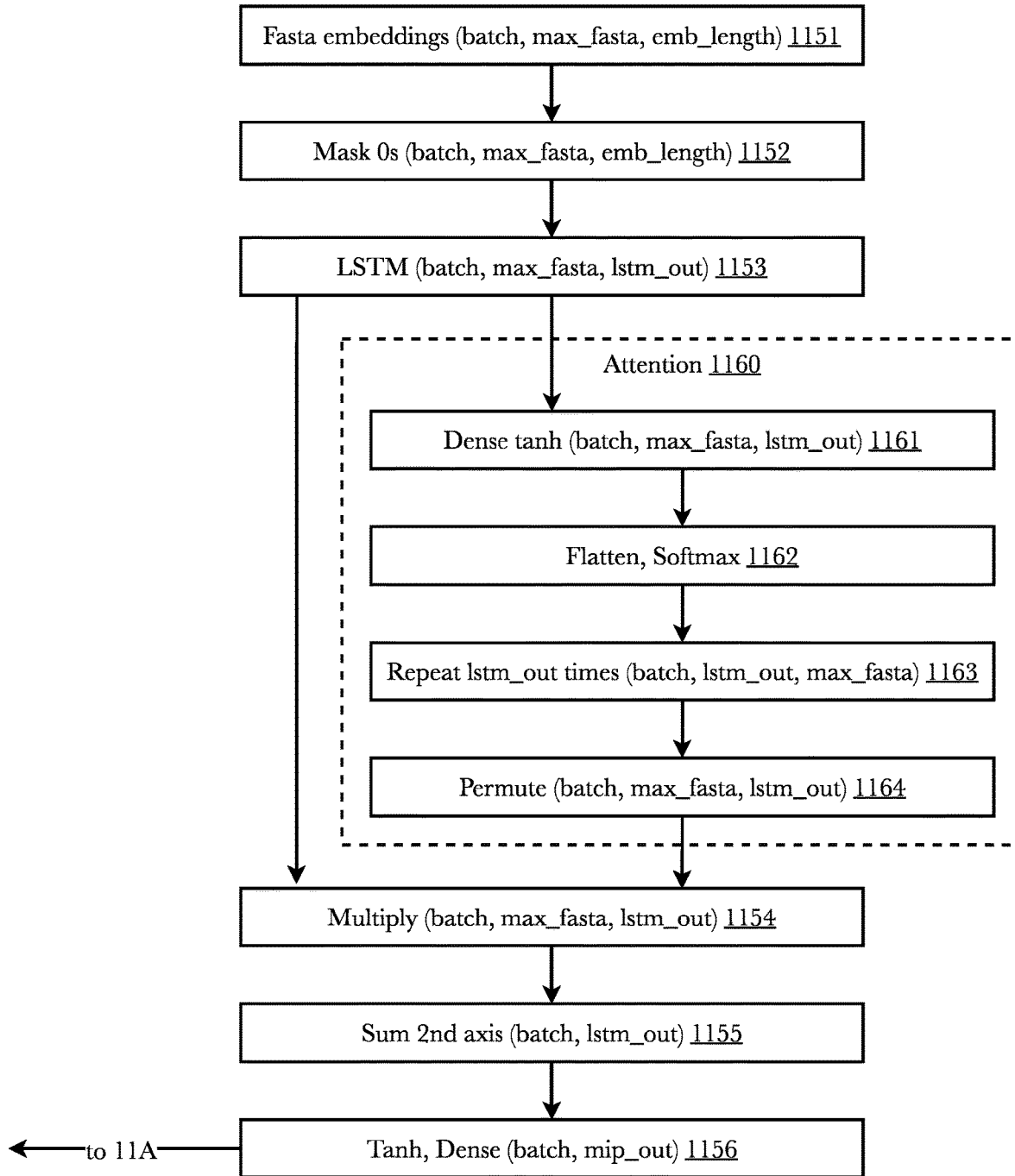

FIGS. 11A and 11B illustrate an exemplary implementation of the architecture for prediction of molecule bioactivity using concatenation of outputs from a graph-based neural network which analyzes molecule structure and a sequence-based neural network which analyzes protein structure. In this example, details regarding a particular implementation of the general architecture shown in FIG. 10 are described.

As shown in FIG. 11A, node features 1111 are received for processing. A reshaping process 1112 may be performed which to conform the dimensionality of the inputs to the dimensionality required for processing by the MPNN. A dense function 1113 is performed to map each node in the previous layer of the neural network to every node in the next layer. Attention is then assigned 1114 using the adjacency matrix contained in the node. The adjacency features (the adjacency matrix) 1115 are simultaneously reshaped 1116 to conform the dimensionality of the inputs to the dimensionality required for processing by the MPNN.

At this stage, a message passing operation 1120 is performed, comprising the steps of performing a dense function 1121 (used only on the first message pass) to map each node in the previous layer of the neural network to every node in the next layer, matrix multiplication of the adjacencies 1122, reshaping of the new adjacencies 1123, and where the message passing operation has been parallelized among multiple processors or threads, concatenating the outputs of the various processors or threads 1124.

Subsequently, a readout operation 1130 is performed comprising performance of a dense function 1131 and implementation of an activation function 1132 such as tan h, selu, etc. to normalize the outputs to a certain range. In this embodiment, the readout operation 1130 is performed only at the first message pass of the MPNN 1110.

As shown in FIG. 11B, FASTA data is converted to high-dimensional vectors 1151, which may then be masked 1152 to conform the vectors to the fixed input length required by the LSTM 1153. The LSTM 1153 then processes the vectors using an attention mechanism 1160 comprising the steps of performing a dense function 1161 to map each node in the previous layer of the neural network to every node in the next layer, performing a softmax function 1162 to assign probabilities to each node just before the output layer. The process is repeated a number of times which may be configured by a parameter 1163. Where permutation invariance is an issue (i.e., where changes in the order of inputs yield changes in the outputs), permutations may be applied to the inputs 1164 to ensure that differences in outputs due to differences in inputs are incorporated.

After attention has been assigned 1160, the vectors in the cells of the LSTM 1153 are multiplied 1154, summed 1155, and a dense function 1156 is again applied to map each node in the previous layer of the neural network to every node in the next layer, and the outputs of the LSTM 1153 are sent for concatenation 1141 with the outputs of the MPNN 1110, after which predictions can be made 1142.

Figure 12:
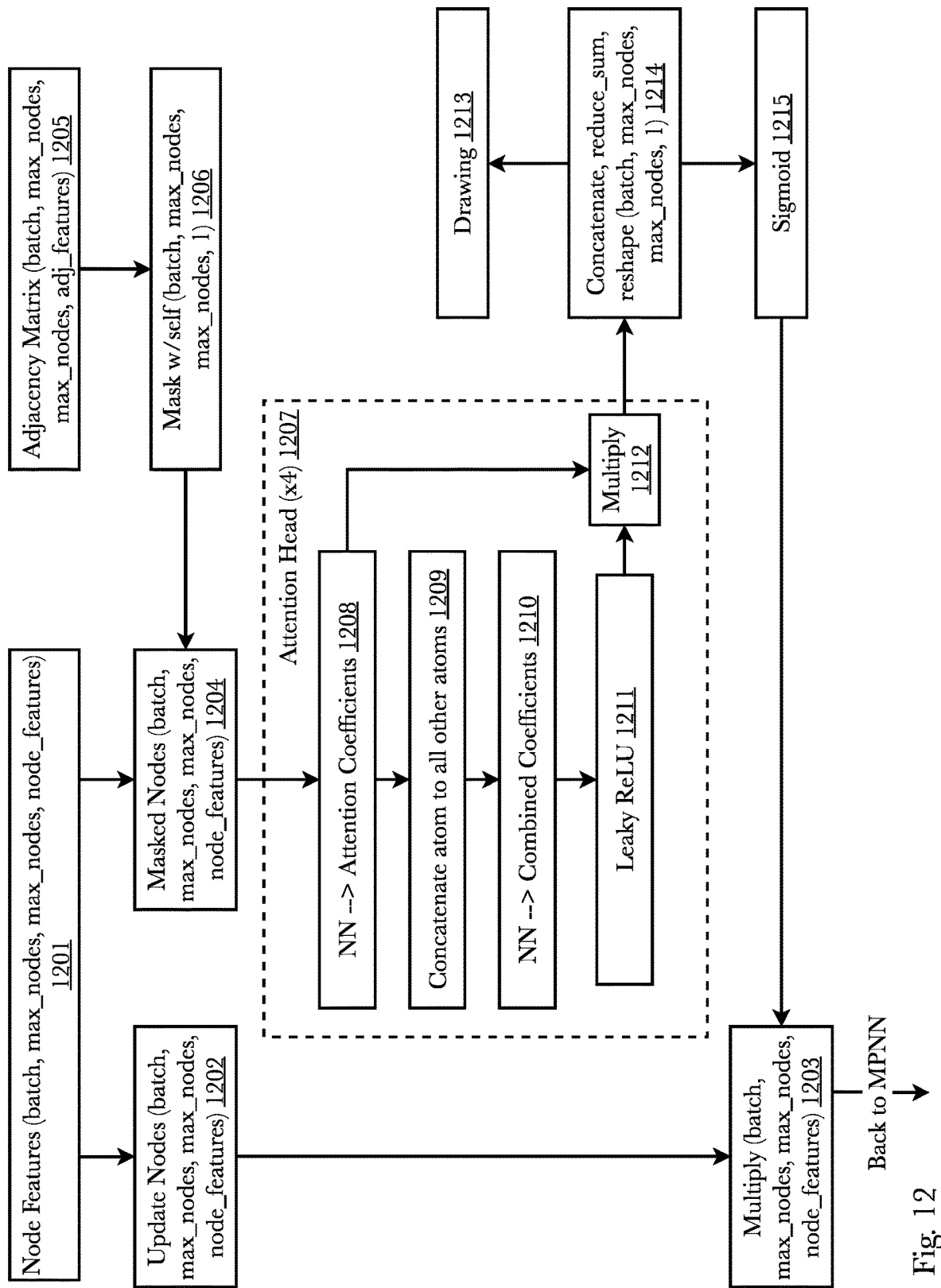
FIG. 12 illustrates an exemplary implementation of the molecule attention assignment aspect of an architecture for prediction of molecule bioactivity using concatenation of outputs from a graph-based neural network which analyzes molecule structure and a sequence-based neural network which analyzes protein structure.

FIG. 12 illustrates an exemplary implementation of an attention assignment aspect of an architecture for prediction of molecule bioactivity using concatenation of outputs from a graph-based neural network which analyzes molecule structure and a sequence-based neural network which analyzes protein structure. This is an exemplary implementation of attention and may not be representative of a preferred embodiment. In this example, details regarding a particular implementation of the attention assignment blocks shown in FIG. 10 are described. The particular implementation of this example involves a multi-head attention mechanism.

As node features 1201 are received for processing, they are updated 1202 and sent for later multiplication 1203 with the outputs of the multiple attention heads 1207. Simultaneously, the nodes are masked 1204 to conform their lengths to a fixed input length required by the attention heads 1207. The adjacency matrix 1205 associated with (or contained in) in each node is also masked 1206 to conform it to a fixed length and sent along with the node features to the multi-head attention mechanism 1207.

The multi-head attention mechanism 1207 comprises the steps of assigning attention coefficients 1208, concatenating all atoms to all other atoms 1209 (as represented in the adjacency matrix), combining the coefficients 1210, performing a Leaky ReLU 1211 function to assign probabilities to each node just before the output layer, and performing matrix multiplication 1212 on the resulting matrices.

The outputs of the multi-head attention mechanism 1207 are then concatenated 1214, and optionally sent to a drawing program for display of the outputs in graphical form 1213. A sigmoid function 1215 is performed on the concatenated outputs 1214 to normalize the outputs to a certain range. The updated node features 1202 are then multiplied 1203 with the outputs of the multi-head attention mechanism 1207, and sent back to the MPNN.

Figure 13:
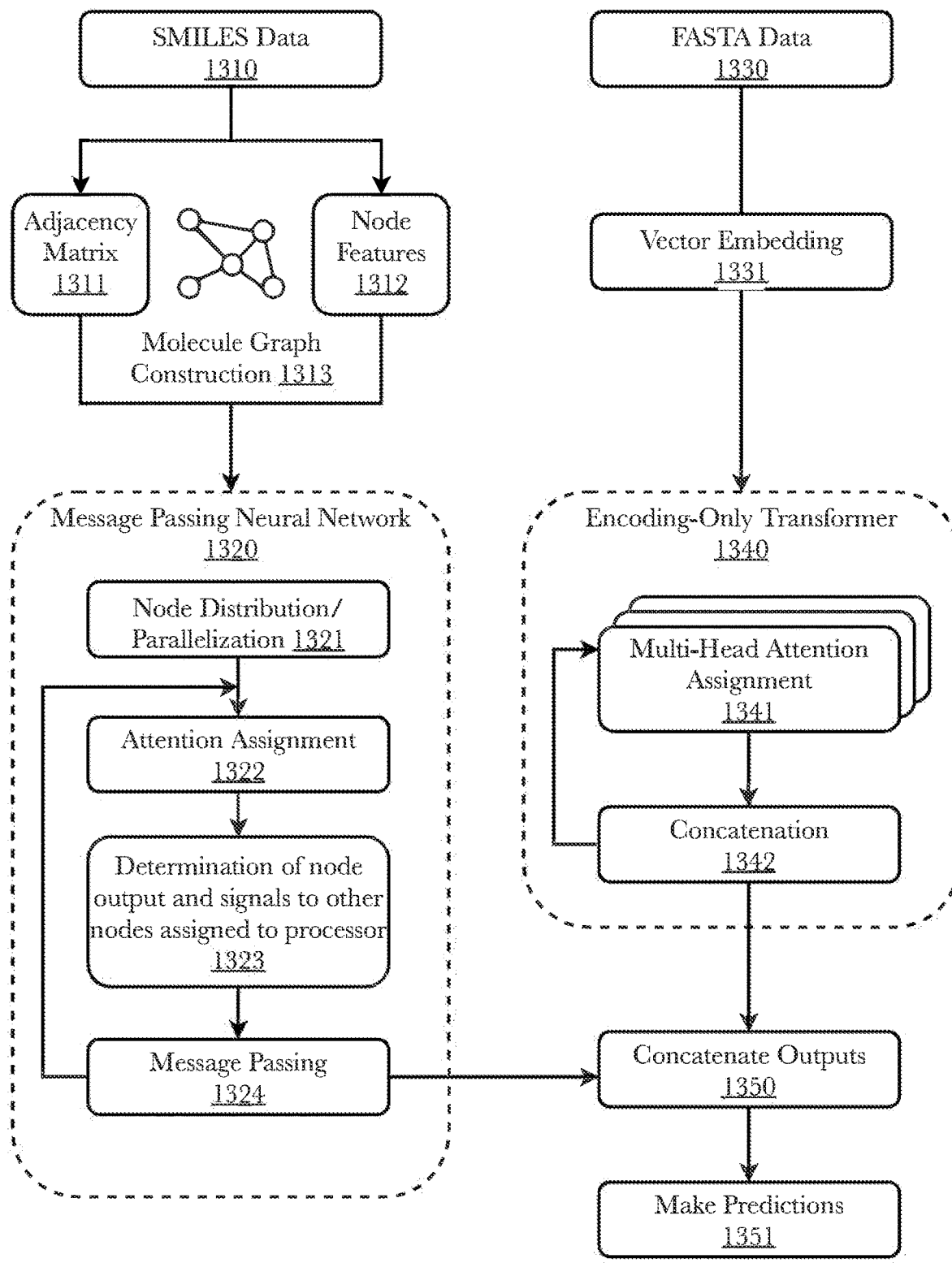
FIG. 13 is a diagram illustrating an exemplary architecture for prediction of molecule bioactivity using concatenation of outputs from a graph-based neural network and an attention-based transformer.

FIG. 13 is a diagram illustrating an exemplary architecture for prediction of molecule bioactivity using concatenation of outputs from a graph-based neural network winch analyzes molecules and their known or suspected bioactivities with proteins and a sequence-based neural network which analyzes protein segments and their known or suspected bioactivities with molecules. In this architecture, in a first neural network processing stream, SMILES data 1310 for a plurality of molecules is transformed at a molecule graph construction stage 1313 into a graph-based representation wherein each molecule is represented as a graph comprising nodes and edges, wherein each node represents an atom and each edge represents a connection between atoms of the molecule. Each node represents the atom as node features comprising an atom type and a number of bonds available for that atom. The node features are represented as a node features matrix 1312. The molecule, then, is represented as nodes (atoms) connected by edges (bonds), and is specified as an adjacency matrix 1311 showing which nodes (atoms) are connected to which other nodes (atoms).

At the training stage, the adjacency matrices 1311 and node features matrices 1312 for many molecules are input into the MPNN 1320 along with vector representations of known or suspected bioactivity interactions of each molecule certain proteins. Based on the training data, the MPNN 1320 learns the characteristics of molecules and proteins that allow interactions and what the bioactivity associated with those interactions is. At the analysis stage, a target molecule is input into the MPNN 1320, and the output of the MPNN 1320 is a vector representation of that molecule's likely interactions with proteins and the likely bioactivity of those interactions.

Once the molecule graph construction 1013 is completed, the node features matrices 1012 and adjacency matrices 1011 are passed to a message passing neural network (MPNN) 1020, wherein the processing is parallelized by distributing groups 1321 nodes of the graph amongst a plurality of processors (or threads) for processing. Each processor (or thread) performs attention assignment 1322 on each node, increasing or decreasing the strength of its relationships with other nodes, and outputs of the node and signals to other neighboring nodes 1323 (i.e., nodes connected by edges) based on those attention assignments are determined. Messages are passed between neighboring nodes based on the outputs and signals, and each node is updated with the information passed to it. Messages can be passed between 1324 processors and/or threads as necessary to update all nodes. In some embodiments, this message passing (also called aggregation) process is accomplished by performing matrix multiplication of the array of node states by the adjacency matrix to sum the value of all neighbors or divide each column in the matrix by the sum of that column to get the mean of neighboring node states. This process may be repeated an arbitrary number of times. Once processing by the MPNN is complete, its results are sent for concatenation 1350 with the results from a second machine learning algorithm, in this case an encoding-only transformer 1340.

In a second processing stream, FASTA data 1330 is converted to high-dimensional vectors 1331 representing the chemical stricture of molecules. The vectors are processed by an encoding-only transformer 1340 which performs one or more iterations of multi-head attention assignment 1341 and concatenation 1342. Once processing by the encoding-only transformer 1340 is complete, its results are sent, for concatenation 1350 with the results from the neural network, in this case the MPNN 1320.

Concatenation of the outputs 1350 from two different types of neural networks (here an MPNN 1320 and an LSTM 1340) determines which molecule structures and protein structures are compatible, allowing for prediction of bioactivity 1351 based the information learned by the neural networks from the training data.

Figure 19:
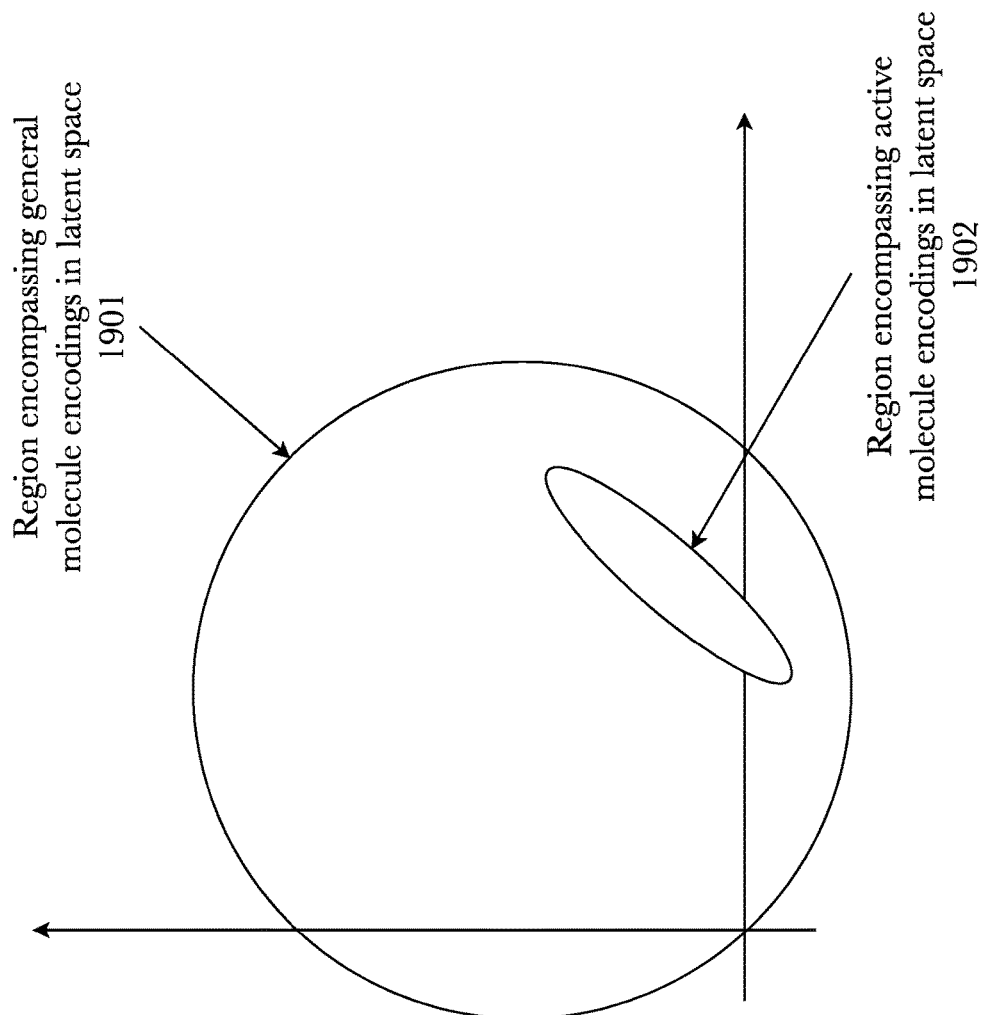
FIG. 19 is a diagram illustrating molecule encodings in latent space.

FIG. 19 is a diagram illustrating molecule encodings in latent space 1901. Once a model is trained that achieves a desirable reconstruction accuracy, a pipeline uses the model to generate molecules similar to a target dataset. Evaluating the generated molecules for chemical validity is performed using defined metrics to compare the generated data and to gauge whether the generation method is performing well. There are a few ways to compare how well the generation process works. When attempting to reconstruct the same molecule, the models sometimes produce molecules that are chemically impossible. It is therefore informative to compare the validity ratio of the generated molecules to the validity ratio of the reconstructed molecules of the active dataset. Ideally, the ratio is similar. If, on the other hand, the validity of the generated data is lower, it might mean that: (a) the exploration method of the latent space is not suitable—the explored space goes beyond the chemically meaningful regions; (b) the latent, space representation is not smooth enough. A second method is by using molecular weight. The generated molecules are expected to have a similar molecular weight distribution to the active samples—a discrepancy would signal problems similar to those above. Lastly, chemical similarity. Computing and comparing the chemical similarity coefficients to estimate the molecular similarity of the generated and active molecules. This similarity should match the similarity of the active compounds amongst one another. These metrics can be used as a simple check validity (i.e., to see if the generated molecules "make sense"). Validity checking is particularly important in cases where certain properties are imposed, such as log P or molecular weight, to the generated molecules, as this is done by modifying the elements in the latent space, and allow the system to find the viable ranges of these parameters by finding where the above metrics start to deteriorate.

New molecules are generated by estimating a distribution of latent space 1902 that the active molecules are embedded into, then sampling from this distribution 1902 and running the samples through a decoder to recover new molecules. The distribution is approximated by a multivariate Gaussian, with mean and covariance matrices computed from the latent representations of the active molecules.

Figure 27:
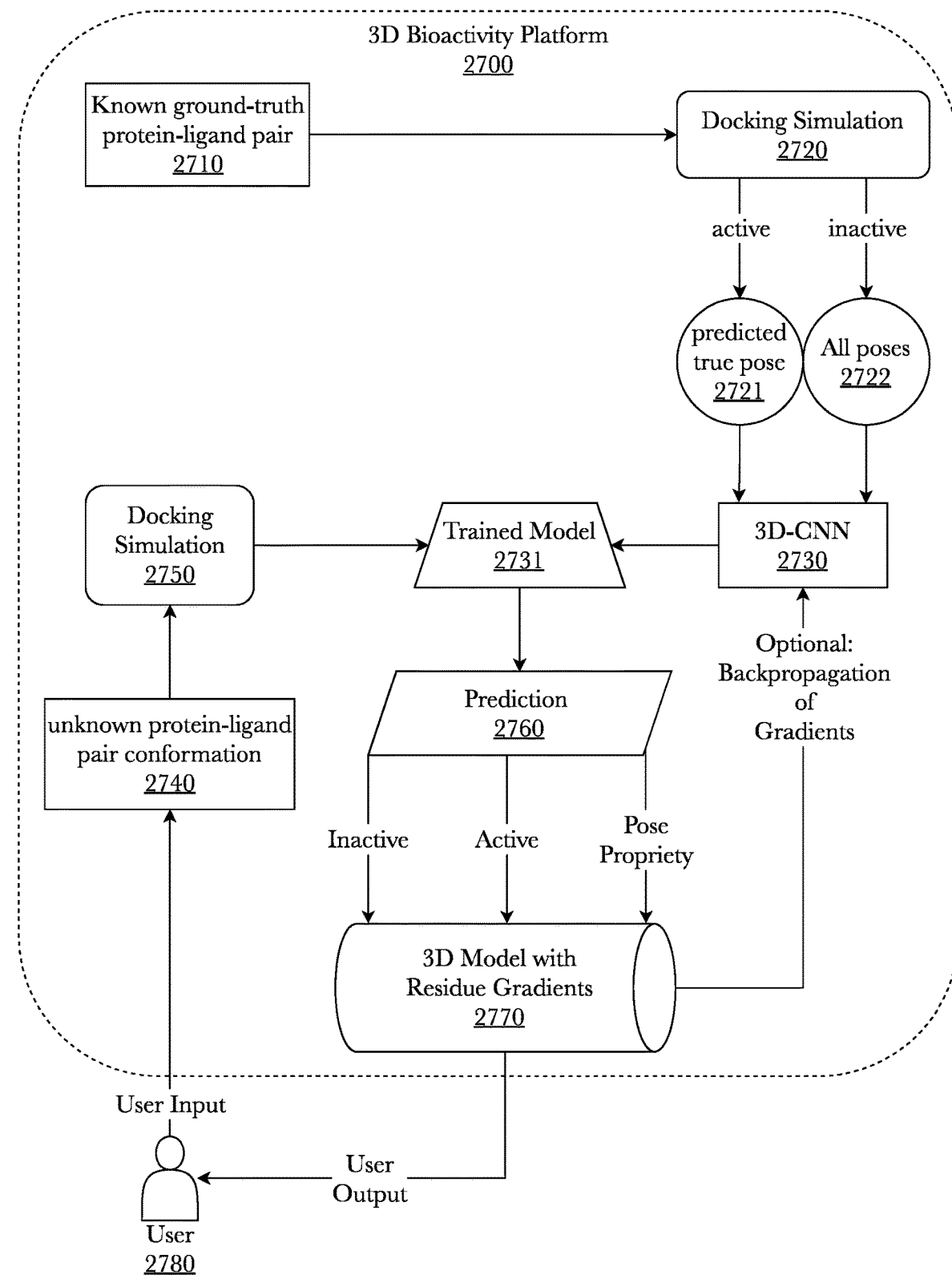
FIG. 27 is a block diagram of an exemplary model architecture for a 3D Bioactivity platform.

FIG. 27 is a block diagram of an exemplary model architecture for a 3D Bioactivity platform 2700. The model architecture used is a three-dimensional convolutional neural network (3D-CNN) 2730. Convolutional Neural Networks 2730 are widely used on tasks such as image classification. They are multi-layer perceptrons that are regularized in such a way as to take advantage of the translational invariance of the content of pictures (e.g., a gavel is a gavel whether it is in the center or corner of an image). In a convolutional layer, each output neuron is not connected to all the input neurons, but to a spatially-localized subset. CNN architectures operate analogously in higher-dimensional spaces. Docking simulations 2720/2750 take as input the ligand and protein molecules 2710/2740 and their three-dimensional structures. Docking 2720 assigns scores to each pose 2721/2722 to be used in the model 2731 depending on the embodiment. Some embodiments may use all poses, whereas other embodiments use only the highest scored pose for active molecules and all poses for inactive molecules. After docking simulations 2720/2750 have been completed, molecules are voxelated and are used as the model 2731 input, which are used to train the model 2731 to predict 2760 or classify these voxelated representations into active/inactive and pose propriety categories.

In reality, the observed bioactivity of a ligand is not due to a single pose within the binding site, but due to the contributions from a number of possible poses. According to one embodiment, the population of a given pose is given as:

$$W_b = e^{\frac{-E}{kT}}$$

where E, k and T correspond to the free energy of binding, Boltzmann's constant, and the temperature, respectively. It estimate of E from the Force Field can be determined, and subsequently the loss may be defined as:

$$L = \frac{\sum_{poses}(W_b * (\text{Model (pose)} - \text{True\_affinity})^2)}{\sum_{poses}(W_b)}$$

This loss function corresponds to interpreting not as the true free energy of binding, but instead as the probability of a pose being the "true" pose. This method allows for superimposing the probability-weighted atom density grids, which speeds computation up enormously. The loss function above is merely exemplary and modifications to the loss function above are anticipated.

According to an aspect of various embodiments, an additional 'Pose Score' output node to the CNN is improvised. 3D-CNNs 2730 comprise an additional output node that is trained on classifying the input poses as being "low" root-mean-square deviation (RMSD) (<2 Angstrom RMSD vs. crystal structure) and "high" RMSD (>2 Angstrom RMSD vs. crystal structure). This predicted classification is used to modulate the binding-affinity loss as follows: Affinity prediction is trained using an L2-like pseudo-Huber loss that is hinged when evaluating high RMSD poses. That is, the model is penalized for predicting both a too low and too high affinity of a low RMSD pose, but only penalized for predicting too high an affinity for a high RMSD pose. Since the PDB dataset used comprises crystal structures for each available datapoint, it is possible to generate corresponding classification labels into high/low RSMD poses for each docked complex. Two aspects of various embodiments are therefore anticipated. The first aspect comprises extracting RMSD labels for datapoints where crystal structures are available and do not contribute any "Pose Score" loss to the remaining items. The second aspect comprises using Boltzmann-averaging of pose predictions. This second aspect has the advantage of not requiring crystal structures of any complexes.

The output 2770 of the model 2731 may combine the separate poses at test-time. Actions taken on the predictions may be selected from one of the actions in the list comprising: Analogous Boltzmann-weighing of the predictions, Averaging of the predictions across all poses, simple predictions only on the best pose, or any combination thereof.

The visualizations 2770 produced by the model 2731 may use methods such as integrated gradients, which require only a single forwards/backwards pass of the models, which is an improvement over the current state of the art According to various embodiments, integrated gradients, and other gradient visualizations are achieved by computing the voxel saliencies, and coloring a surface/molecule of its properties. If a MaxPool layer is an initial layer of the model 2731, simple smoothing (i.e., halving the resolution of the grid) may correct the visualization from the zero-average voxel-importance.

Other visualizations methods comprise assigning voxel-gradients back to the atoms of the input molecules, which are adapted to propagate whatever importances are computed for each voxel. Importances provide the user with an explanation of which parts of the protein-ligand pair the model 2731 predicts is most strongly bonded. The more important the atom, the higher the number. The number may be represented by one or more colors or shading. The importance reference system described above, i.e., the color-coordinated importances, is only one example of an importance reference system. Other methods such as coloring, shading, numbering, lettering, and the like may be used.

One use of the exemplary 3D bioactivity platform 2700 embodiment disclosed herein comprises a user 2780 that inputs unknown molecule conformations 2740 into the 3D bioactivity platform 2700 and receives back a prediction as to whether the molecule is active or inactive, a pose score (telling the propriety of the pose), and a 3D model complete with gradient representations of the significant residues 2760/2770.

Figure 29:
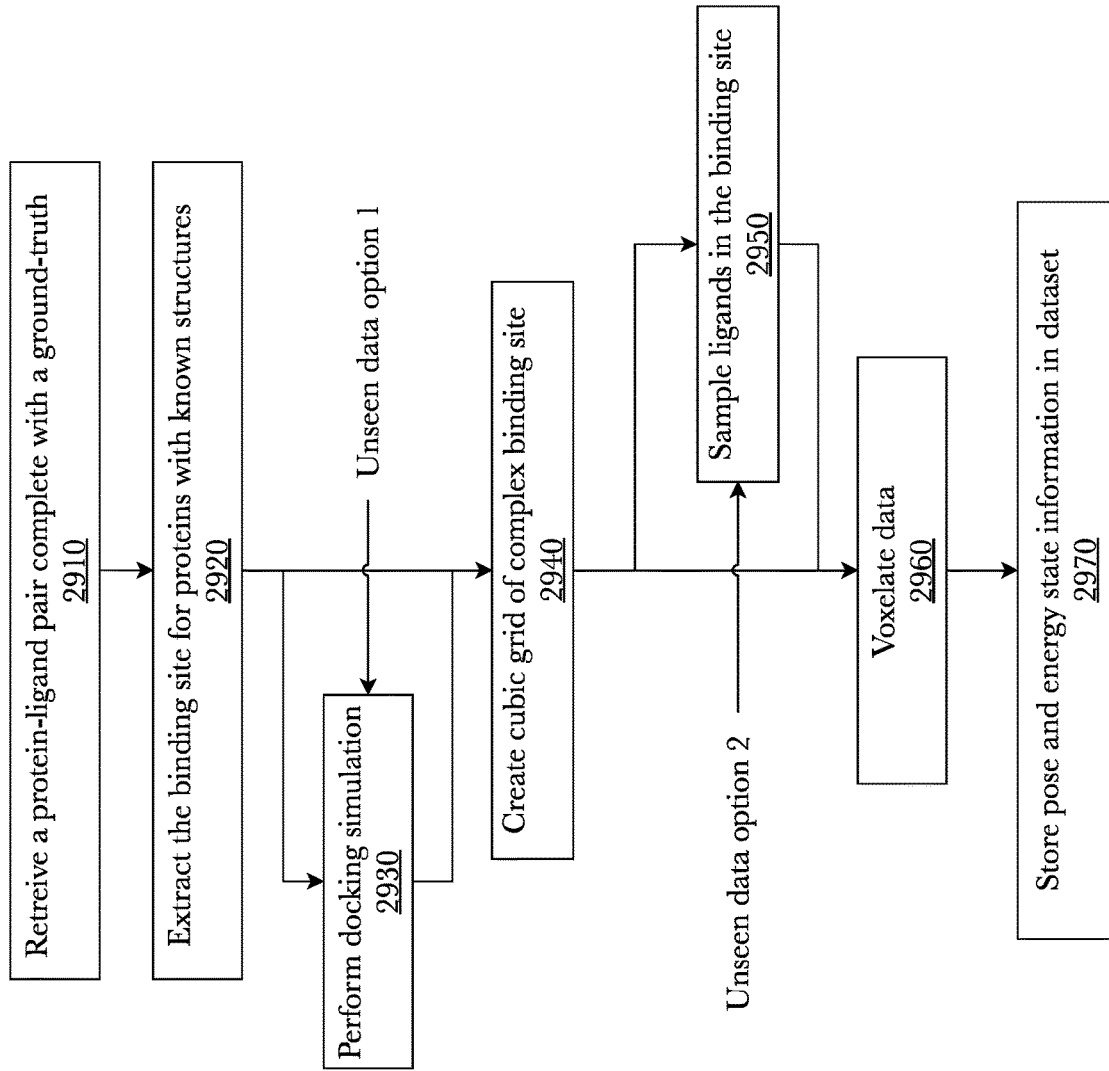
FIG. 29 is a flow diagram illustrating an exemplary method for generating data for use in training a 3D-CNN used by a 3D Bioactivity platform.

FIG. 29 is a flow diagram illustrating an exemplary method for generating data for use in training a 3D-CNN used by a 3D Bioactivity platform. Training data is generated for the training of the classifier via docking, wherein method of docking gives the energy states of each protein-ligand pose. The lower the energy state, the stronger the binding affinity. Inputs for the docking mechanism comprise a particular protein-ligand pair and its ground-truth state (i.e., whether it is active or inactive) 2910. On such a pair, the docking simulation is performed and if the pair is labeled as inactive, all data points are kept in the training dataset, if an active label is found as the ground truth state, only the best (lowest energy) pose is kept. According to another embodiment, the top 20 (lowest energy) poses are kept for the training dataset. Further anticipated embodiments acknowledge that any number of poses may be kept for training and the examples contained herein are merely exemplary. According to aspects of various embodiments, simple force-field based optimization of a ligand pose in a binding pocket can substitute for docked poses at reduced computational expense in a binding affinity prediction task without a significant decrease in accuracy. Force-field optimization considers at least one of the constant terms selected from the list of dissociation, inhibition, and half-concentration (IC50) in order to capture the molecular interactions, e.g., hydrogen bonds, hydrophobic bonds, etc. Many databases known in the art may be used to get this information such as the Protein Data Bank (PDB) as one example. In simple terms, docking guides the machine learning (3D-CNN) to realize what poses to keep and to realize what the molecule likely looks like in the pocket.

Prior to featurization, the model input should be a cubic grid centered around the binding site of the complex, the data being the location and atom type of each atom in each the protein and ligand, flagged as to belonging either to the protein or die ligand. This is trivial for complexes with known structures, wherein the binding site is the center of the ligand. For unseen data, two exemplary options are anticipated: generate complexes using docking, or generate complexes by sampling ligand poses.

According to one embodiment, an initial step in dataset creation is to extract the binding sites from all the proteins for which have known structures (this need only be done once ever) 2920. Next, using the aforementioned docking option, complexes are created via docking simulations 2930. However, if the foregoing second option is used, then sampling the ligands in the binding site using the cropped protein structures may be done post-step three for faster data loading 2950. The next step 2940 is to crop to a 24 Angstrom box around the binding-site center (either geometric or center-of-mass). The data is then voxelated 2960 and stored in a dataset 2970. Different box sizes or centering choices is anticipated, however, in one embodiment, the data is voxelated to a certain resolution, e.g., 0.5 Angstrom. This resolution is sensible as it ensures no two atoms occupy the same voxel.

Figure 34:
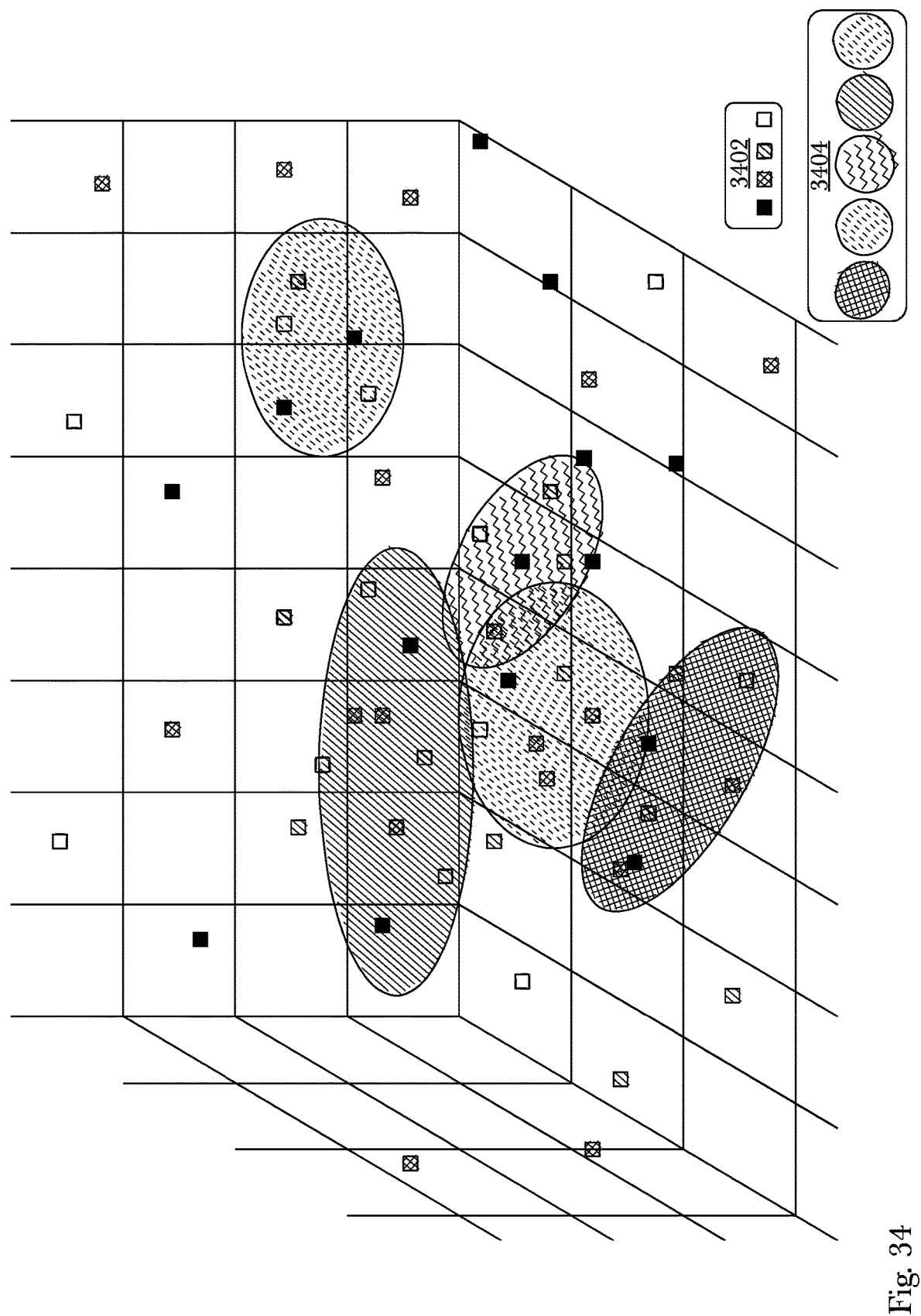
FIG. 34 is an exemplary visualization of a localized maximum suppression step of the maximal sampling method used by a molecular reconstruction module.
Figure 35:
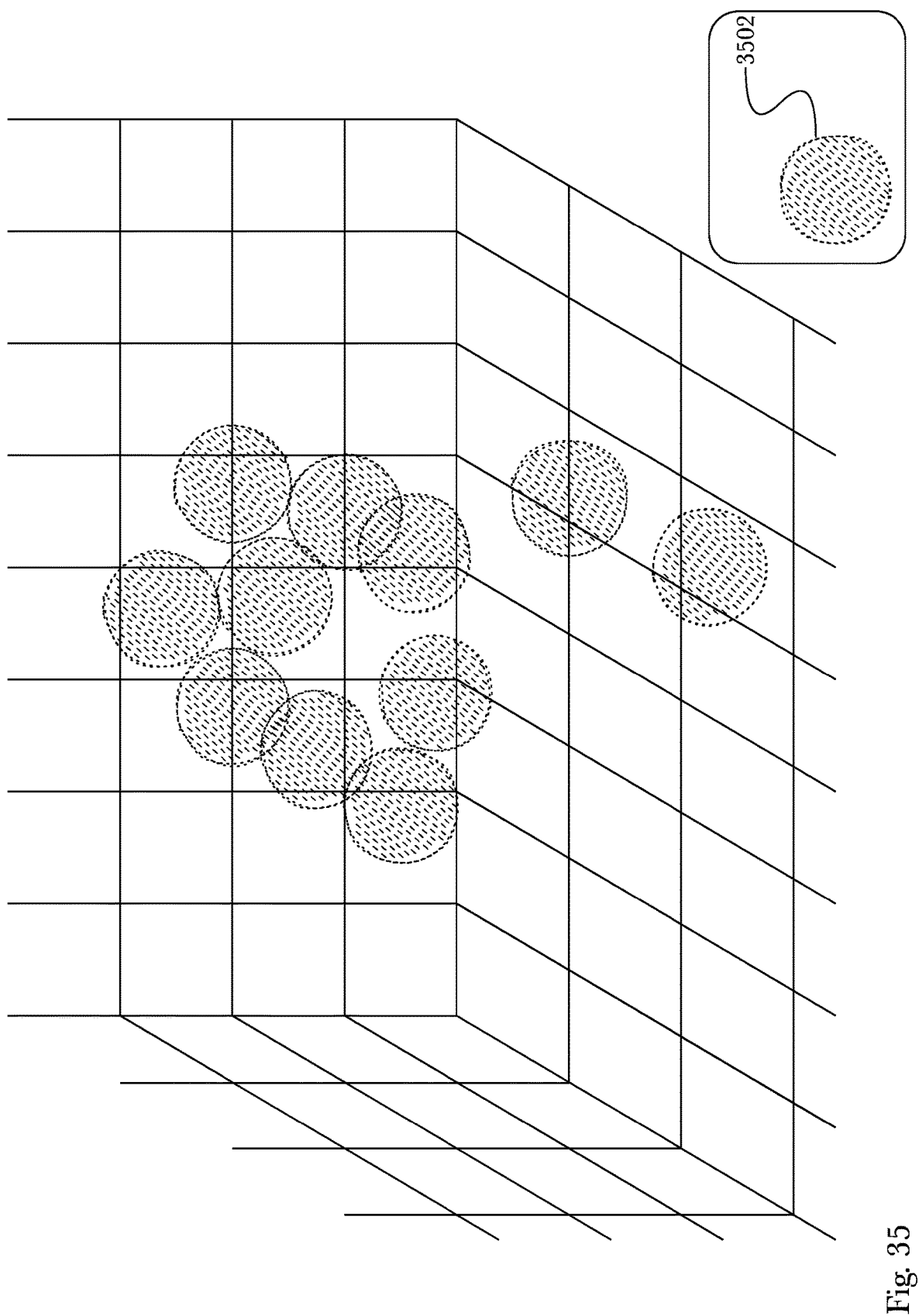
FIG. 35 is an exemplary visualization of a Gaussian mixture model step of the maximal sampling method used by a molecular reconstruction module.
Figure 36:
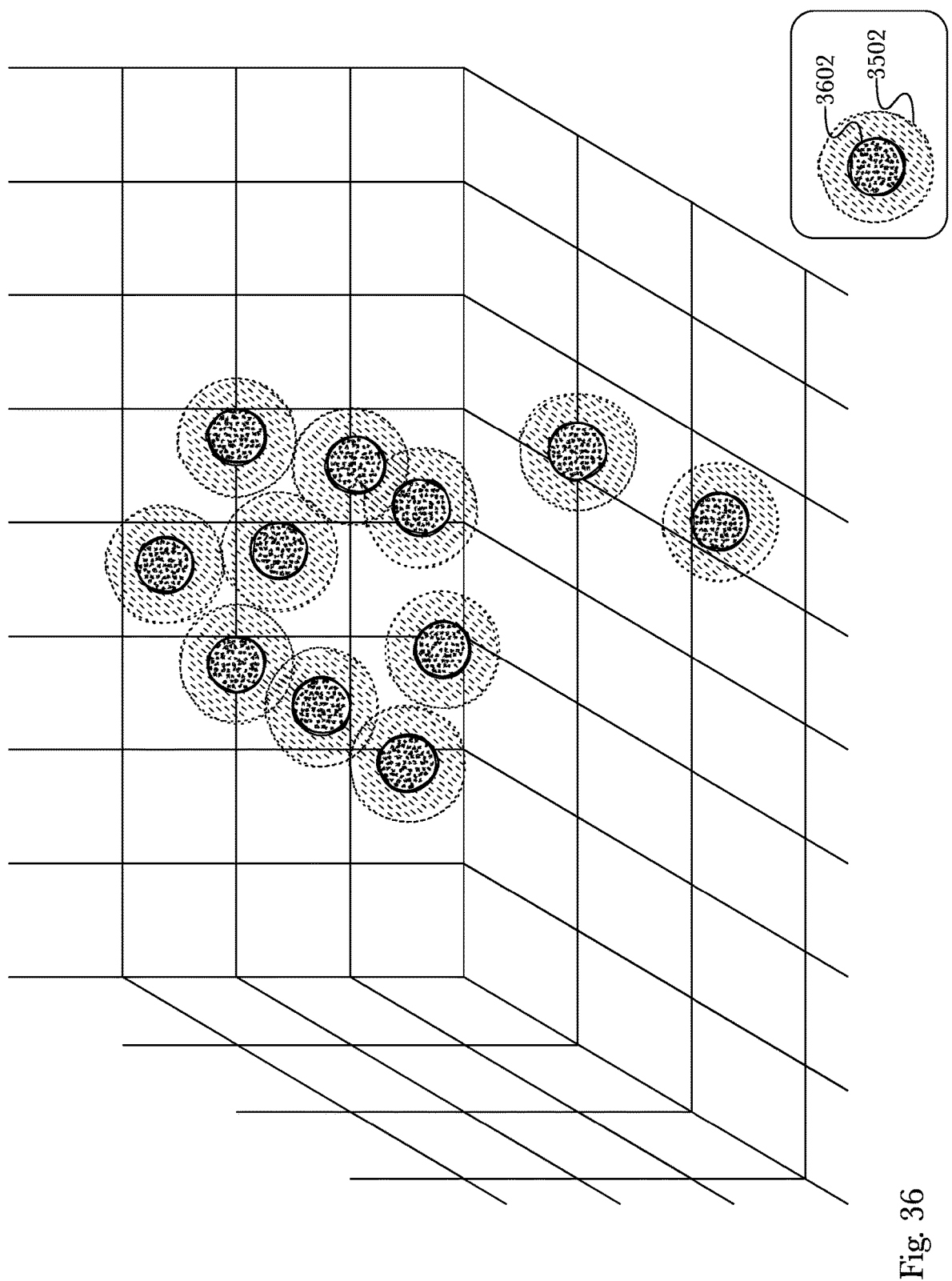
FIG. 36 is an exemplary visualization of a Gaussian mixture model (with centroids) step of the maximal sampling method used by a molecular reconstruction module.
Figure 37:
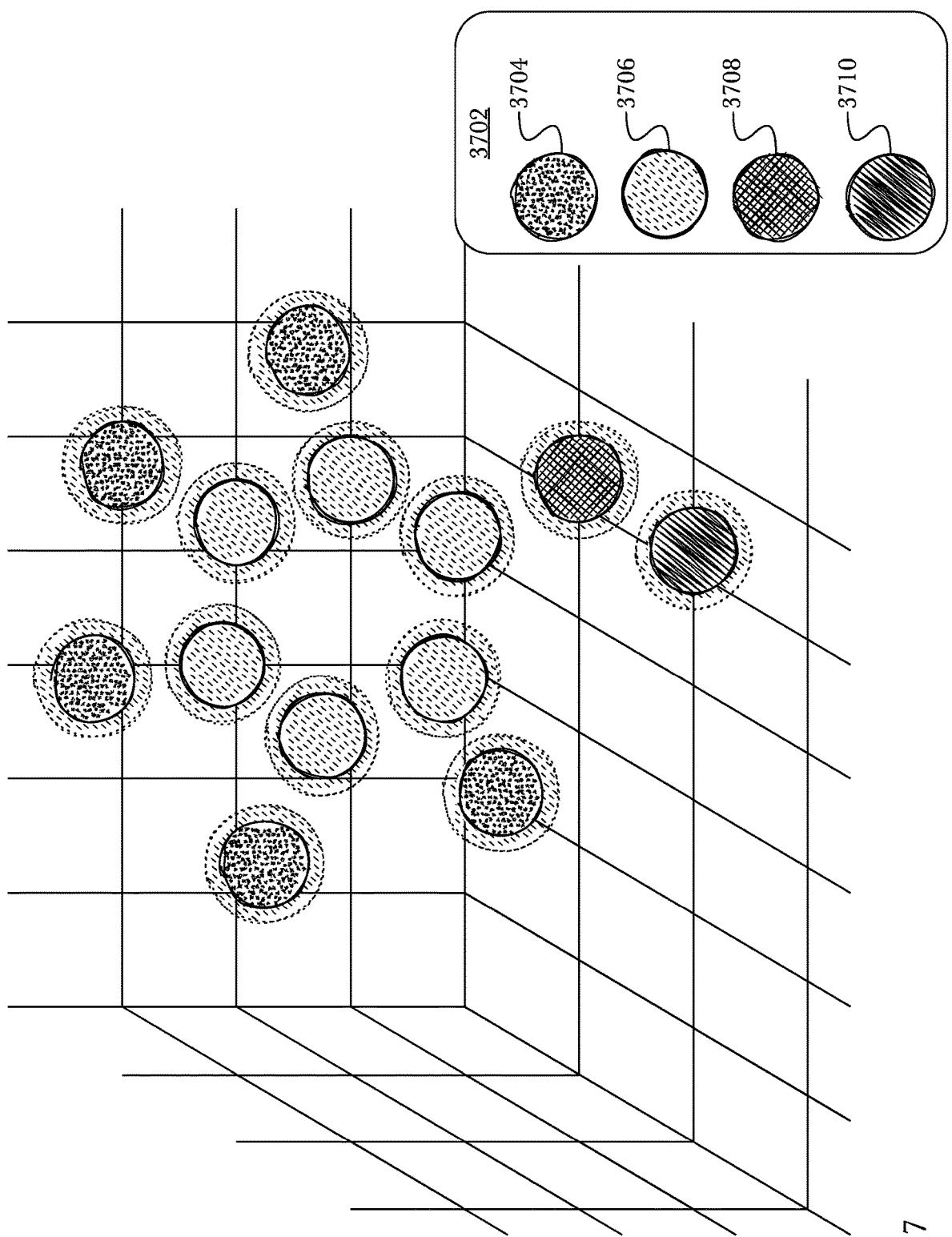
FIG. 37 is an exemplary visualization of a Akaike's Information Criteria and Bayesian Information Criteria step of the maximal sampling method used by a molecular reconstruction module.

FIG. 34 is an exemplary visualization of a localized maximum suppression step of the maximal sampling method used by a molecular reconstruction module. Further expanding on the density-to-molecule transformation described in FIG. 30B, maximal sampling is employed because it may be decided that the true molecule representation should represent spatial probability distributions instead of low-resolution discretized one-hot tensors which dictate the position of the atoms in space. The reason for this is that by allowing the position of an atom to be defined as a spherical 3D Gaussian-like distribution, we vastly relax the resolution errors from discretizing the grid. Maximal sampling is a form of sampling where a probability distribution obtains the local maxima of said distribution. It is a form of non-maximal suppression or simulated annealing. With this, a set of one-hot representations of a dense molecular distribution can be obtained, which can be used to construct its SMILES (amongst other molecular representations) equivalent. FIG. 34 illustrates the step of localized maximum suppression where the goal of this step is to transform the probabilistic representation (Gaussian) of the point clouds produced by the generator. To that end, a form of localized suppression based on Gaussian Mixture Models (GMMs) is employed. Since the Gaussian representation of the atom 3402 is isotropic, we use Spherical GMMs (SGMMs). GMMs are a form of unsupervised learning where clusters are formed during an expectancy-maximization optimization procedure. As shown in the figure, each Gaussian (i.e., the various patterns 3404), finds a way to position itself (optimization of Mean and Covariance matrix), in order to adequately describe the observed data. FIG. 35, FIG. 36, and FIG. 37 illustrate an optimization of the GMM models by composing every channel in the true representation as Gaussian spheres 3502. GMM operation learns the mean and covariance matrices. The number of clusters is approximated by the "occupancy" of each channel, and a search space is performed based on Akaike's Information Criteria and Bayesian Information Criteria. The result is a space of GMM centroids 3602. After this process is performed independently for all channels, a resulting representation is provided 3702. As a simplified example, imagine after the optimization of the GMM models, a molecular representation may be provided of a carbon ring 3706 with hydrogen 3704, oxygen 3710, and sulfur 3708 atoms.

FIG. 34-FIG. 37 are merely exemplary and have been significantly simplified to improve readability and comprehension and is further not indicative of a true representation of all of the possible complex representations actually produced by the various embodiments. Furthermore, any factual inaccuracies in FIG. 34-FIG. 37 are merely owing to the reduction of complexity from the real-world examples for the purposes of readability and comprehension of the figures.

Hardware Architecture

Generally, the techniques disclosed herein may be implemented on hardware or a combination of software and hardware. For example, they may be implemented in art operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 46:
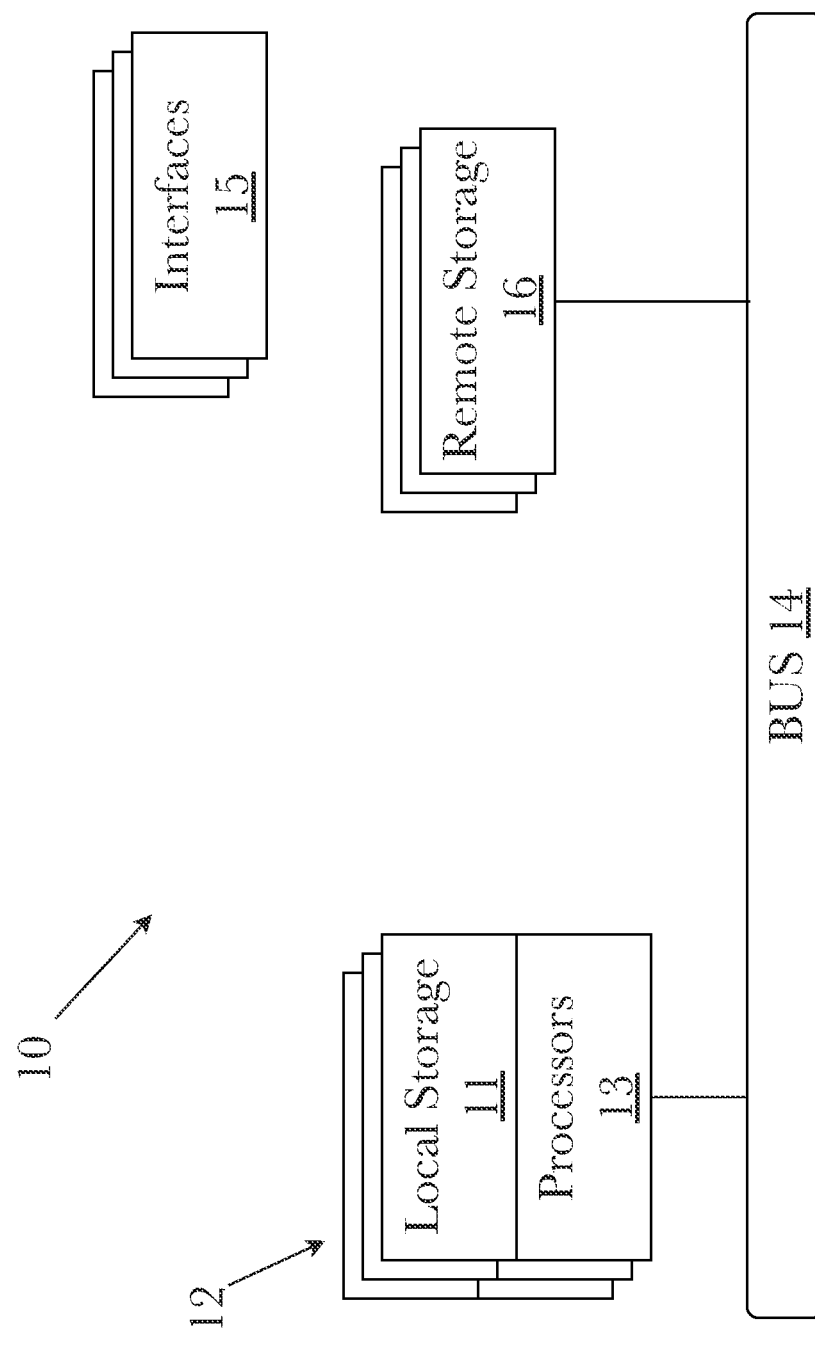
FIG. 46 is a block diagram illustrating an exemplary hardware architecture of a computing device.

Referring now to FIG. 46, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "'processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 13 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 46 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media, designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 47:
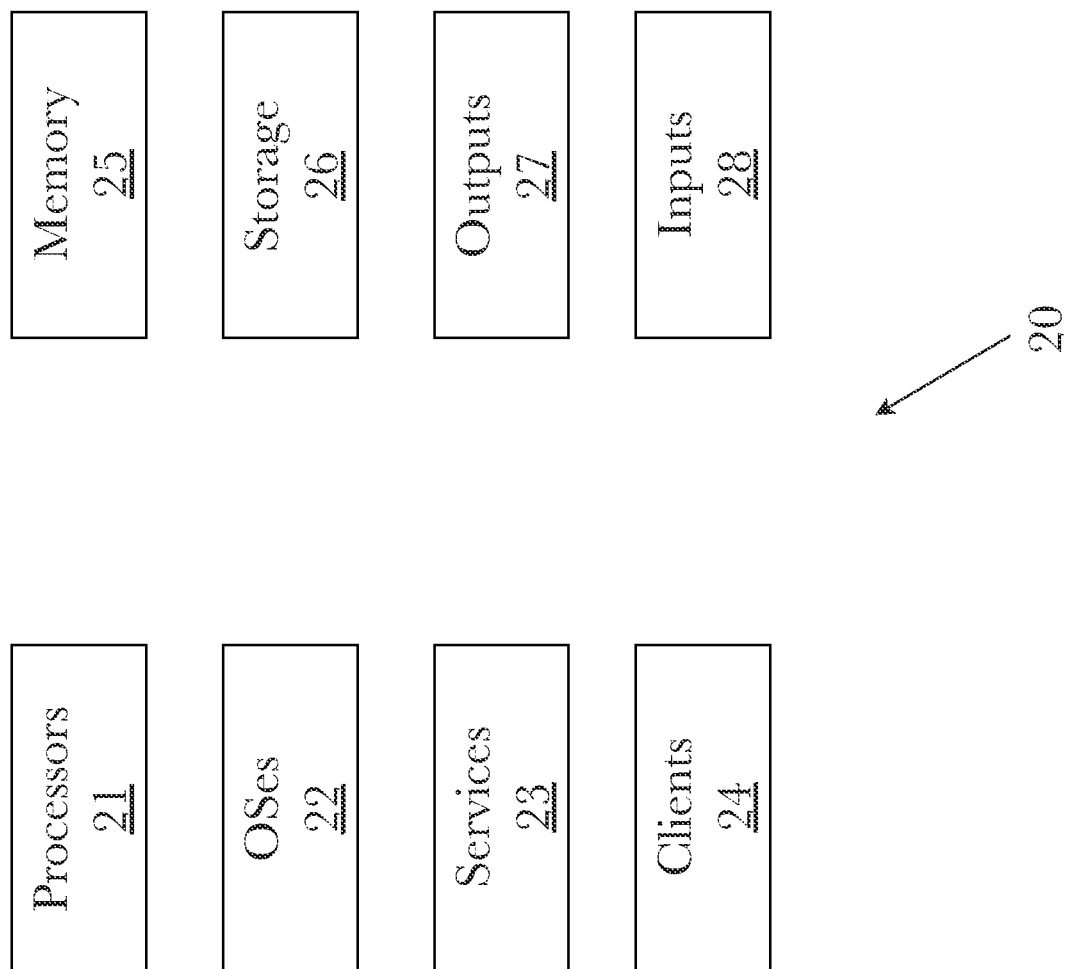
FIG. 47 is a block diagram illustrating an exemplary logical architecture for a client device.

In some aspects, systems may be implemented on a standalone computing system. Referring now to FIG. 47, there is shown a block diagram depicting a typical exemplary architecture of one or more aspects or components thereof on a standalone computing system. Computing device 20 includes processors 21 that software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more, screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 46). Examples of storage devices 26 include flash memory, magnetic hard drive, CD-ROM, and/or the like.

Figure 48:
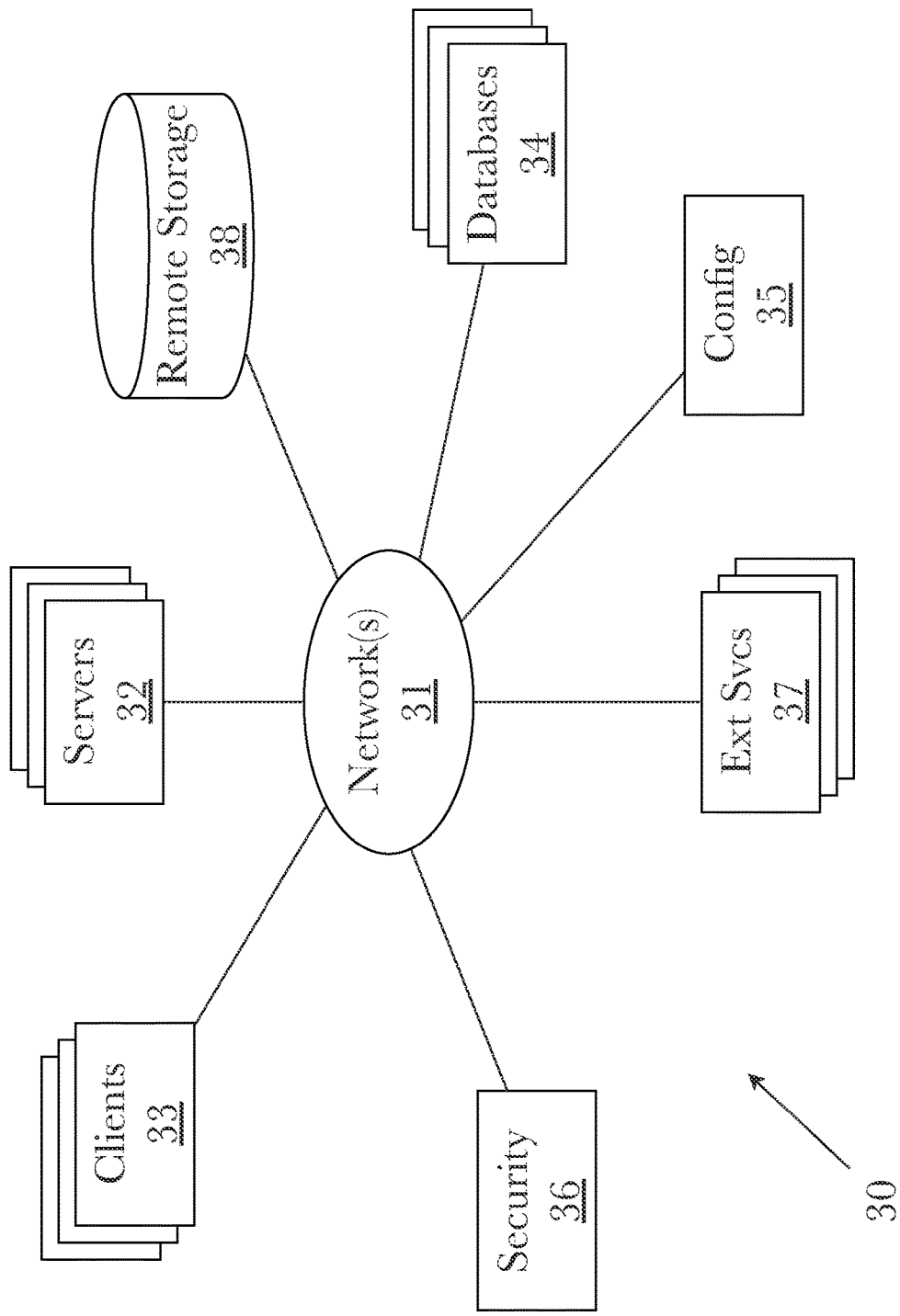
FIG. 48 is a block diagram showing an exemplary architectural arrangement of clients, servers, and external services.

In some aspects, systems may be implemented on a distributed computing network, such as one having any number of clients and/or servers. Referring now to FIG. 48, there is shown a block diagram depicting an exemplary architecture 30 for implementing at least a portion of a system according to one aspect on a distributed computing network. According to the aspect, any number of clients 33 may be provided. Each client 33 may run software for implementing side portions of a system; clients may comprise a system 20 such as that illustrated in FIG. 47. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 49:
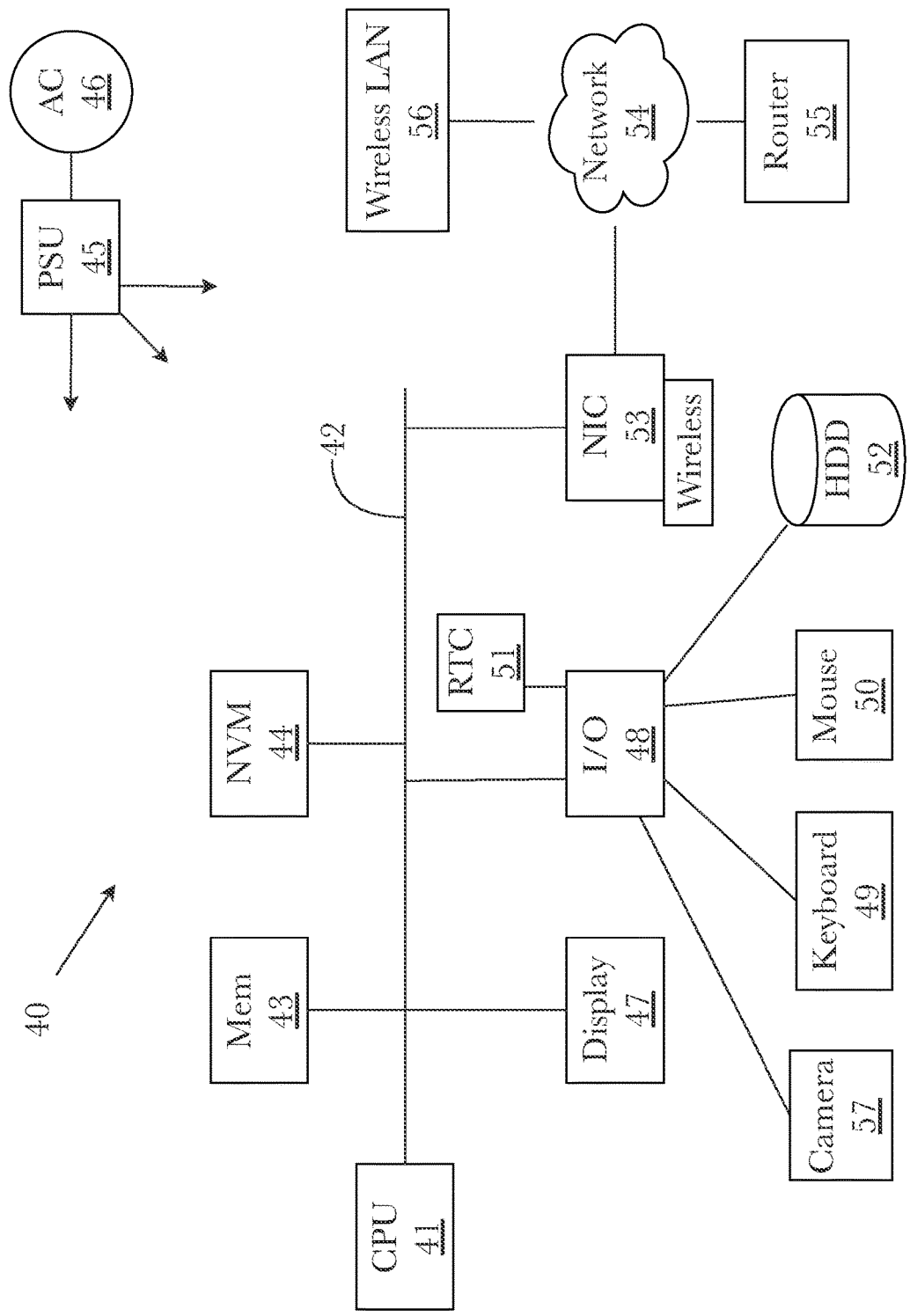
FIG. 49 is another block diagram illustrating an exemplary hardware architecture of a computing device.

FIG. 49 shows an exemplary overview of a computer system 40 as may be used in any of the various locations throughout the system. It is exemplary of any computer that may execute code to process data. Various modifications and changes may be made to computer system 40 without departing from the broader scope of die system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have, to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. Tor example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for the reconstruction of molecular representations from molecular probability distributions, comprising:
a computer system comprising a memory and a processor;
an embeddings module, comprising a first plurality of programming instructions stored in the memory and operating on the processor, wherein the first plurality of programming instructions, when operating on the processor, causes the computer system to:
receive a dataset of molecules comprising ground-truth information relating to the molecules;
use the dataset with an encoder to train a model of each molecule in the dataset, wherein the molecule model comprises every substructure in each molecule, and wherein each substructure is represented as an embedding;
use contrastive optimization across all the molecule models to form clusters of similar substructures; and
assign signatures to each embedding, wherein similar substructure embeddings have similar signatures and less-similar substructure embeddings have less-similar signatures;
a substructure processing module, comprising a second plurality of programming instructions stored in the memory and operating on the processor, wherein the second plurality of programming instructions, when operating on the processor, causes the computer system to:
receive a probability distribution of a molecule;
predict a set of molecular descriptors from the probability distribution, wherein the set of molecular descriptors comprises at least one of the following: substructure centroids, substructure dimensions, substructure directions, substructure embeddings, or some combination thereof;
wherein the substructure embeddings are determined by comparative signature analysis the substructure embeddings generated by the embeddings module; and
encode the set of molecular descriptors into a tensor, wherein the tensor fully describes the molecule; and
a junction tree connector module, comprising a third plurality of programming instructions stored in the memory and operating on the processor, wherein the third plurality of programming instructions, when operating on the processor, causes the computer system to:
receive the tensor of molecular predictions;
use the tensor to predict the junction tree node structure;
use the tensor to predict the atomic assignment of each atom in each substructure;
connect the substructures together to form a valid molecule using the predicted junction tree node structure and atomic assignments; and
produce a molecular string which is fully representative of the molecule from the molecular probability distribution.

2. The system of claim 1, wherein the substructure processing module is trained using an object-detection algorithm.

3. The system of claim 2, wherein the object-detection algorithm uses a template matching task rather than a classification task.

4. The system of claim 1, wherein the junction tree connector module uses a deep learning transformer.

5. The system of claim 1, wherein the molecular string is a SMILES string.

6. The system of claim 1, wherein the molecular string is a DeepSMILES string, preferable to deep learning applications.

7. The system of claim 1, wherein the probability distribution of a molecule is generated by a variational autoencoder.

8. The system of claim 1, wherein the embeddings generated can be recycled in structure-based generative modelling.

9. The system of claim 1, wherein the substructure processing module uses a Hungarian-matching algorithm to determine the ground-truth set of molecular properties.

10. The system of claim 1, wherein the prediction of the junction tree node structure is determined using a Hungarian-matching algorithm by pruning incorrect nodes.

11. A method for the reconstruction of molecular representations from molecular probability distributions, comprising the steps of:

training an encoder to model each molecule in a dataset, wherein the molecule model comprises every substructure in each molecule of the dataset, and wherein each substructure is represented as an embedding;

using contrastive optimization across all the molecule models to form clusters of similar substructures;

assigning signatures to each embedding, wherein similar substructure embeddings have similar signatures and less-similar substructure embeddings have less-similar signatures;

predicting a set of molecular descriptors from a molecular probability distribution, wherein the set of molecular descriptors comprises at least one of the following: substructure centroids, substructure dimensions, substructure directions, substructure embeddings, or some combination thereof;

determining the molecular descriptor substructure embedding by comparative signature analysis with the generated substructure embeddings;

encoding the set of molecular descriptors into a tensor, wherein the tensor fully describe the molecule;

using the tensor to predict the junction tree node structure of the molecular probability distribution and to predict the atomic assignment of each atom is each substructure;

connecting the substructures together to form a valid molecule using the predicted junction tree node structure and predicted atomic assignments; and producing a molecular string which is fully representative of the molecule from the molecular probability distribution.

12. The method of claim 11, wherein an object-detection algorithm is used for the prediction of a set of molecular properties.

13. The method of claim 12, wherein the object-detection algorithm uses a template matching task rather than a classification task.

14. The method of claim 11, wherein a deep learning transformer is used to connect the substructures together.

15. The method of claim 11, wherein the molecular string is a SMILES string.

16. The method of claim 11, wherein the molecular string is a DeepSMILES string, preferable to deep learning applications.

17. The method of claim 11, wherein the probability distribution of a molecule is generated by a variational autoencoder.

18. The method of claim 11, wherein the embeddings generated can be recycled in structure-based generative modelling.

19. The method of claim 11, wherein a Hungarian-matching algorithm is used to determine the ground-truth set of molecular properties.

20. The method of claim 11, wherein the prediction of the junction tree node structure is determined using a Hungarian-matching algorithm by pruning incorrect nodes.

* * * * *